(12) United States Patent
Dhankher et al.

(10) Patent No.: US 10,947,551 B2
(45) Date of Patent: Mar. 16, 2021

(54) COMPOSITIONS AND METHODS FOR ENGINEERING OIL CONTENT IN PLANTS

(71) Applicant: The University of Massachusetts, Boston, MA (US)

(72) Inventors: Om Parkash Dhankher, Amherst, MA (US); Sudesh Chhikara, Amherst, MA (US)

(73) Assignee: THE UNIVERSITY OF MASSACHUSETTS, Boston, MA (US)

( * ) Notice: Subject to any disclaimer, the term of this patent is extended or adjusted under 35 U.S.C. 154(b) by 105 days.

(21) Appl. No.: 15/902,697

(22) Filed: Feb. 22, 2018

(65) Prior Publication Data

US 2018/0237792 A1    Aug. 23, 2018

Related U.S. Application Data

(60) Provisional application No. 62/462,624, filed on Feb. 23, 2017.

(51) Int. Cl.

| | | |
|---|---|---|
| *C12N 15/82* | (2006.01) | |
| *C12N 9/10* | (2006.01) | |
| *C12N 9/12* | (2006.01) | |
| *C12N 9/04* | (2006.01) | |

(52) U.S. Cl.
CPC ....... *C12N 15/8247* (2013.01); *C12N 9/0006* (2013.01); *C12N 9/1029* (2013.01); *C12N 9/1288* (2013.01); *C12N 15/8218* (2013.01); *C12N 15/8261* (2013.01); *C12Y 101/01008* (2013.01); *C12Y 203/0102* (2013.01); *C12Y 203/01022* (2013.01); *C12Y 207/08002* (2013.01); *C12N 2830/65* (2013.01)

(58) Field of Classification Search
None
See application file for complete search history.

(56) References Cited

U.S. PATENT DOCUMENTS

| | | |
|---|---|---|
| 6,444,876 B1 | 9/2002 | Lassner et al. |
| 6,552,250 B1 | 4/2003 | Nykiforuk et al. |
| 7,511,189 B2 | 3/2009 | Zou et al. |
| 7,579,517 B2 | 8/2009 | Renz et al. |
| 2012/0004125 A1 | 1/2012 | Cahoon et al. |

OTHER PUBLICATIONS

Doerks et al., (TIG, 14:248-250, 1998).*
Smith et al. (Nature Biotechnology, 15:1222-1223, 1997).*
Bork et al. (TIG, 12:425-427, 1996).*
Graham et al. (PNAS, 116:3126-3135, 2019).*
Zhou et al. (Oncotarget., 8:101309-101324; 2017).*
Hanzawa et al. (PNAS, 102:7748-7753, 2005).*
Wishart et al. (JBC, 270:26782-26785, 1995).*
Nishimura et al. (Plant Cell Physiol., 41(5):583-590, 2000).*
Yang et al. (PNAS, 98:11438-11443, 2001).*
McConnell et al. (Nature, 411:709-713, 2001).*
Wells (Biochemistry 29:8509-8517, 1990).*
Guo et al. (PNAS, 101: 9205-9210, 2004 ).*
Ngo et al., (The Protein Folding Problem and Tertiary Structure Prediction, K. Merz., and S. Le Grand (eds.) pp. 492-495,1994).*
Thornton et al. (Nature structural Biology, structural genomics supplement, Nov. 2000).*
Keskin et al. (Protein Science, 13:1043-1055, 2004).*
Liu et al. (Gene, 557:163-171, 2015).*
Jako et al. (Plant Physiol., 126:861-874, 2001).*
Vigeolas et al. (Plant Biotechnology Journal, 5:431-441, 2007).*
Renooij et al. (Biochim. Biophys. Acta. 663 (2): 545-56).*
Zavareh et al. (PLoS One, 7 (9) e43721-e43721).*
Nobusawa et al. (Biochem Biophys Acta Mol Cell Biol Lipids, 1864(9):1185-1193, 2019).*
Gutterson (HortScience 30:964-966,1995).*
Bruening (Proc. Natl. Acad. Sci., 95:13349-13351, 1998).*
Elomaa et al. (Molecular Breeding, 2:41-50, 1996).*
Colliver et al. (Plant molecular Biology, 35:509-522, 1997).*
Emery et al. (Current Biology 13:1768-1774, 2003).*
Arziman et al. (Nucleic Acids Research, 33:582-588, 2005).*
Bonawitz et al.,(Annu. Rev. Genet. 44: 337-363, 2010).*
Paul et al., (Plant Cell Reports; 35:1417-1427; 2016).*
Petrie et al. (PLoS One, 7(4): e35214-e35214; Published Apr. 2012).*
Wickramarathna et al. (BMC Biotechnology, 15:63, 1-15; 2015).*
Kim et al. (Biotechnology for Biofuels, 7:36, 1-16; 2014).*
Genbank (NCBI, Sequence Accession No. XM_010489120.1; Published Dec. 1, 2014).*
Jako C., et al., "Seed-Specific Over-Expression of an Arabidopsis cDNA Encoding a Diacylglycerol Acyltransferase Enhances Seed Oil Content and Seed Weight", Plany Physiology, vol. 126, 2001; pp. 861-874.
Vigeolas, H. et al., "Increasing seed oil content in oil-seed rape (*Brassica napus* L.) by over-expression of a yeast glycerol-3-phosphate dehydrogenase under the control of a seed-specific promoter", Plant Biotechnology Journal (2007) 5, pp. 431-441.

(Continued)

*Primary Examiner* — Vinod Kumar
(74) *Attorney, Agent, or Firm* — Cantor Colburn LLP

(57) ABSTRACT

Compositions and methods for producing plants with enhanced oil content and higher seed yield are disclosed. The transgenic plant comprises a polynucleotide encoding a monoacylglycerol O-acyltransferase 1 (MGAT1) operatively linked to a plant-expressible promoter; a polynucleotide encoding a phosphatidylcholine diacylglycerol cholinephosphotransferase 1 (PDCT1) operatively linked to a plant-expressible promoter; a polynucleotide encoding a suppressor of expression of Sugar Dependent 1 (SPD1) operatively linked to a plant-expressible promoter; a polynucleotide encoding a diacylglyerol acyltransferase (DGAT1) operatively linked to a plant-expressible promoter and a polynucleotide encoding a glycerol-3-phosphate dehydrogenase (GPD1) operatively linked to a plant-expressible promoter; or a combination thereof.

20 Claims, 15 Drawing Sheets
Specification includes a Sequence Listing.

(56) References Cited

OTHER PUBLICATIONS

Xu, J. et al., "Cloning and characterization of an acyl-CoA-dependent diacylglycerol acyltransferase 1 (DGAT1) gene from Tropaeolum majus, and a study of the functional motifs of the DGAT protein using site-directed mutagenesis to modify enzyme activity and oil content", Plant Biotechnology Journal, (2008) 6, pp. 799-818.

Chhikara, Sudesh, et al., "Engineering *Camelina sativa* (L.) Crantz for enhanced oil and seed yields by combining diacylglycerol acyltransferase 1 and glycerol-3-phosphate dehydrogenase expression", Plant Biotechnology Journal (2018) 16, pp. 1034-1045.

* cited by examiner pCambiaRedSeed/BnBcNA1-pro::CsMGAT::Nos-t pCambiaRedSeed/Pv-pro::CsPDCT::Nos-t

SEQUENCE LISTING

```
<160> NUMBER OF SEQ ID NOS: 19

<210> SEQ ID NO 1
<211> LENGTH: 1593
<212> TYPE: DNA
<213> ORGANISM: Arabidopsis thaliana
<220> FEATURE:
<221> NAME/KEY: variation
<222> LOCATION: (613)..(614)
<223> OTHER INFORMATION: residues are AG (S205 protein) or GC (A205
      protein variant)

<400> SEQUENCE: 1
atggccatat tagactctgc aggggtcacc acggtcactg agaacggggg gggagaattt      60
gtcgatttgg ataggttacg tagaagaaag agtcgatcag actcatctaa cggacttctg     120
ttgtctggat ctgacaacaa cagcccttct gacgatgttg gtgcaccagc tgacgtacgc     180
gatagaattg atagtgttgt taacgacgat gctcagggga cggccaactt ggcaggtgac     240
aacaatgggg gaggagataa taatggggga ggccggggcg gaggtgaggg tagaggtaac     300
gctgatgcca cctttacata ccgtccttca gttcctgctc acagacgcgc gagggaatct     360
```

```
ccactcagtt cggacgctat atttaagcaa tcgcacgcag gtcttttttaa tctctgcgtg     420 gtcgtcctta tcgctgtaaa ttctcgcctc atcatcgaaa atttgatgaa atatggttgg     480
ctcattcgaa ctgattttg gttttcatcg cgatcactta gagattggcc gttattcatg      540
tgctgtatct ccctctctat tttcccacta gctgctttta cagttgagaa gctcgttttg     600
caaaagtata tcrstgaacc tgtcgtgatt tttctacata ttattattac gatgacagag     660
gtactatatc ccgtgtacgt gacactcaga tgcgattcag cctttctttc aggtgtaaca     720
ttgatgcttt tgacatgcat tgtttggctt aagctagttt cctatgccca tacttcatac     780
gacatcaggt ctttggctaa cgctgctgac aaggctaatc ctgaagttag ctactacgtt     840
agtctcaaaa gtttggctta tttcatggta gctcctactc tttgttacca gccaagttat     900
ccccggtccg catgtatacg aaaggggttgg gtggctcgtc agtttgcaaa actcgtgatc    960
ttcacaggtt tcatgggttt cattattgag cagtatatta atccaattgt acgaaattca    1020
aagcacccat tgaagggaga tctactgtac gctatcgagc gcgttcttaa attatcagtt    1080 ccaaatctttt atgtttggct ttgcatgttc tattgcttct ttcatttgtg gctaaacatc    1140
cttgcagagc ttctttgttt cggtgatcgc gaattttaca aggattggtg gaacgcaaaa    1200
tcagtcggag attactggag aatgtggaac atgcctgtgc ataaatggat ggtgagacat    1260
atttactttc cgtgtttaag atctaagatt ccaaagacat tagctattat tatagcgttt    1320
ctcgttagcg cggtctttca cgaactttgc atcgctgttc cgtgtcgact cttcaagctg    1380
tgggcgtttc tggggatcat gtttcaagtc ccattggttt ttattaccaa ttaccttcag    1440
gaacgctttg ggtctacagt cgggaatatg atcttctggt ttatttttttg tatcttcgga    1500 cagccgatgt gtgtattatt gtactaccat gatttaatga ataggaaggg tagcatgtca    1560
gaacagaaac tgatctctga agaagatctg tga                                 1593
```

<210> SEQ ID NO 2
<211> LENGTH: 1206
<212> TYPE: DNA
<213> ORGANISM: Saccharomyces cerevisiae

<400> SEQUENCE: 2

```
atgtctgcgg ctgcggatag attaaacttg acctccggtc atttgaatgc aggccgtaaa      60
agatcaagtt caagcgttag cttgaaggct gcagaaaagc catttaaggt tacagtcatt     120
ggttctggaa actggggtac cactattgca aaagttgtcg ctgaaaactg taaaggatac     180
ccagaggttt tcgctcctat agtgcagatg tgggtttttg aggaggagat taacggcgag    240
aaacttactg agattataaa cacgcgccat cagaacgtta agtacttacc tggtatcacc    300
ctacctgaca atcttgtggc caacccggat ctgattgact ccgtgaaaga gtgacatc      360 attgttttca acataccgca ccagttttta cctaggatat gttctcaact taagggtcat    420
gttgacagcc atgtgcgtgc tatctcttgt cttaagggat tgaggttgg agctaaggga    480 gttcagttac tgagttccta cataacggag gagctgggta ttcagtgcgg tgcattgtct    540
ggagctaata ttgctactga agttgctcaa gaacattggt ctgagacgac tgtagcatat    600
catattccta aggatttcag aggtgaggga aaagatgtag accacaaggt tttgaaagca    660
ttgttccata ggccctactt ccatgtttca gtgattgagg atgtcgctgg catttctata    720
tgtggtgcct taaaaaacgt ggtagctctc ggttgtggat tcgttgaagg tcttggatgg    780
ggaaacaacg catctgcagc aatccaaaga gttggattgg gtgaaatcat taggtttggg    840
```

```
caaatgtttt ttcctgaaag ccgtgaggag acctattatc aagaatcggc aggggttgct    900
gacctcataa cgacatgtgc tggaggccgt aacgtaaagg tggctaggtt gatggccacc    960
tcaggaaaag atgcttggga atgtgagaag gaactgctca acggacaatc cgcacaagga   1020
ctcatcactt gtaaagaagt tcatgagtgg ttagaaactt gtggaagcgt cgaggacttt   1080
ccactgttcg aggccgtcta tcaaattgtg tataataact atccgatgaa aaaccttcct   1140
gacatgatcg aagagcttga tctacatgaa gacgaacaga aactgatctc tgaagaagat   1200
ctgtga                                                              1206
```

<210> SEQ ID NO 3
<211> LENGTH: 1008
<212> TYPE: DNA
<213> ORGANISM: Camelina sativa

<400> SEQUENCE: 3

```
atgccgtcag aagcgacttc agctccggcg tctcctccgc caccaccacc gaacttttgg     60
ggagacatgc cggaggaaga atactacact tcacaaggat gcgtaacac caaatcatac    120 ttcgagacgc ccaacggcaa gctcttcact cagagctttt taccgttaga cggtgagatc    180
aaagggactg tgtacatgtc tcacggctac ggatctgatt ctagctggat gtttcagaag    240
atctgtatca gtttctctac ttggggttac gctgttttcg ccgccgatct tcttggtcac    300
ggccgttccg atgggatacg ctgctacatg ggtgatatgg agaaagttgc agcaacatca    360 ttagcttct tcaagcatgt gcgttttagt gatccgtata agaatcttcc tgcttttctc    420
tttggtgagt ctatgggagg tcttgtgacg cttctaatgt attttcaatc cgaacctgat    480
acttggactg gattgatctt tacggctcct ctctttgtta tccctgagga tatgaaacca    540
agcaagcctc accttttgc ttacggtctt ctctttggtt tggctgatac gtgggcggca    600
atgccggata taagattgt ggggaaggct attaaagatc cggtaaagct taagatcatc    660
gcatctaacc cgcaaagata cacagggaag cctagagtgg gaacaatgag agagttgcta    720
aggaagaccg agtacgttca ggagaacttc gggcgagtta ctattccggt atttacggcg    780
cacgggacag cggatggagt atcatgtcct acatcgtcga agctactata tgagagggca    840
tcgagcactg ataaaacgtt gaagatctat gaagggatgt accattcgct gattcaagga    900
gagcctgacg agaacgttga gattgtgttg aaggatatga gagagtggat cgacgaaagg    960
gtcaagaggt atgggatcta aaccgctcat catccacatc accattga              1008
```

<210> SEQ ID NO 4
<211> LENGTH: 921
<212> TYPE: DNA
<213> ORGANISM: Camelina sativa

<400> SEQUENCE: 4

```
atgtcagcca ccgcagctaa acccgccgtc tctcgccgtc acgtatctaa cggaaaccac     60
actaacaacg tcgccattga cgacgatcac aaccaccaac gccccgtaga cgtcggagat    120
acaaacactc gaatggagat cgctgctaag aacaacggct acgccaacgg tgtcatcgga    180
ggaggatgga ggagcaaggc gtcgttcatg acgtggacga cgcgtgacgt tgtctacgtg    240
gcgagacacc attggatacc gtgcatgttc gctgccgggc ttttgttctt catgggggtc    300
gagtacacgc tccagatgat acccgcgaga tctgagccgt tcgatcttgg gtttgtagcc    360
acgcgctctt tgaatcgcgt cttagcatct tccccgatc taaacactgt tctagccgca    420
ctaaacacgg tgttcgtatt gatgcaaaca acgtatattg tatggacatg gttagtggaa    480
```

```
ggacgagcac gagcaaccat ctcggcttta ttcatgttca cttgtcgcgg cattctcggc    540
tactctactc agcttcctct ccctcaggat tttttaggat caggagttga ttttccggtg    600
ggaaacgtct ctttcttcct cttcttctcg ggccacgttg ccggctcgat gatcgcatcg    660
ttggacatga ggagaatgca aaggtttaag ctggcgaggg ttttttgacat cctcaatgta    720 ttacaatcga tcaggctgct cggtacaaga ggacactaca ccatcgacct tgcggttgga    780
gttggcgctg ggattctttt tgactcactg gccggaaagt acgaagagat gagcagaaga    840
caccacctag gaactggttt tagtttgata tcgaaagact ctctagtcaa ttacccatac    900
gacgtcccag actacgctta a                                              921
```

```
<210> SEQ ID NO 5
<211> LENGTH: 2484
<212> TYPE: DNA
<213> ORGANISM: Camelina sativa

<400> SEQUENCE: 5
atggatataa gtaatgaagc cagtgttgat ccctttcga ttggaccaac atcgatcatg      60
ggtcgaacca ttgctttcag agtcttgttc tgtagatcta tggcacagct taggcgtgat    120
ctttttcgct ttttgctgca ttggttcctt aggtttaagc tgactgtatc accgttttg     180 tcgtggtttc atcctcggaa cccacaaggg atcttagcag tggttacaat cattgctttc    240
ttgttgaaac gttacaccaa tgtgaagata aaagcggaaa tggcttacag gaggaaattt    300
tggaggaaca tgatgcggac ggcttttgact tatgaggaat gggctcatgc tgctaagatg    360
ttggagaagg agacgccgaa gctgaatgaa tctgatcttt atgatgaaga gttggttaag    420
aacaagcttc aggagcttcg tcatcgtcgc caagaaggtt cgcttagaga catcatgttt    480
tgtatgagag ctgatctcgt gaggaatctt ggtaatatgt gtaactcgga gcttcataaa    540
ggtagacttc aggttcctag acatatcaaa gagtatatcg atgaggtctc tactcagttg    600
agaatggtct gtaactctga ctcagaggag ctttctttgg aagagaagct ttcctttatg    660
cacgaaacac ggcatgcctt tggtagaacg gctttgcttt tgagtggtgg ggcttctctt    720
ggtgcgtttc atgttggtgt ggttaggact ttggttgagc ataagctttt acctcggatc    780
attgctggtt ctagtgtcgg atccataatt tgtgctgttg tagcctcaag gtcttggccc    840
gagctacaaa gttctttga gaattctttg cattctttac agttctttga tcagcttgga    900
ggcgttttct caatcgtgaa acgagtaatg acacaaggcg ctctacatga tatcagacag    960
ttacagtgta tgcttagaaa cctcacaagc aatctcactt tccaagaagc ttatgacatg   1020
acaggaagga tacttgggat aaccgtttgt tccccaagaa agcatgaacc tcctcggtgt   1080
cttaactatt tgacttcgcc tcatgtggtt atatggagcg cagtgactgc ttcttgtgcc   1140
tttcctggtc tctttgaagc tcaagagcta atggctaaag atcgaagtgg agagatcgtg   1200
ccgtatcatc cacctttcaa tttggatcca gaagtaggca ctaaatcgtc tggacgccgg   1260
tggagagatg gtagtttgga ggttgattta ccaatgatgc agcttaagga actgttcaat   1320
gtgaatcatt ttattgtgag tcaagccaat cctcacattg ctcccttact ccgtctgaag   1380
gatttagttc gagcttatgg cggtagattc gcagctaagc tcgcgcatct agtggagatg   1440
gaggtcaaac atagatgcaa ccaggtatta gagcttggtt ttccacttgg tggacttgca   1500
aagctatttg ctcaggagtg ggaaggtgat gtaacagttg taatgcctgc tactcttgct   1560
cagtactcga agattataca aaacccgact catgtcgatc ttcagaaagc ggctaaccaa   1620
```

```
ggaagaaggt gcacttggga gaagctttca gccataaaat caaactgcgg gatcgagctt    1680
gctcttgatg attcagtggc tatacttaac catatgcgta ggctcaagaa aagcgccgag    1740
agagccgcca gtgccacgtc atcgtctcac cacggattag cttcaacaac cagattcaat    1800
gcttctagaa gaatcccatc ttggaacgtc attgccagag agaactcaac gggttcactc    1860
gatgatctag tcgctgacaa caacaatctc catgcttctt cgggcaggaa tctaagcgac    1920
agtgaaacag agagtgtgga actgagttct tggacacgaa ctggtggacc tttgatgaga    1980
acagcttctg ctaataagtt cattgacttt gttcagtctc ttgatatcga cattgcattg    2040
gcaagagggt tcagtagcag tcccaattct ccagcagttc ctcctggcgg cccatttagt    2100
ccaagcgcga gatccatgtc tgctcattcc gataacgaac caaacagcaa tagcaacaac    2160
aacactactt caagaataac agtgactgaa ggtgaccttc tacagcctga gagaacaagt    2220
aacgggtttg tgttaaatgt tgttaaaaga gagaacttgg gaatgtcatc tataggggg     2280 aatcaaaata cagagttacc ggagagtgta cagcttgata taccggagaa agagatggat    2340
aatagctctg tatccgaaca cgaagtagac gatgacgata acaagaaga taataacggt     2400 gcaacggtct cgagtccggt tactgaatct tcagaagatt ccggtttaca agaaccggtg    2460
tctggtagtg ttatagatgg ttag                                          2484

<210> SEQ ID NO 6
<211> LENGTH: 690
<212> TYPE: DNA
<213> ORGANISM: Glycine max

<400> SEQUENCE: 6
atagcctaag tacgtactca aaatgccaac aaataaaaaa aaagttgctt taataatgcc     60
aaaacaaatt aataaaacac ttacaacacc ggatttttt taattaaaat gtgccattta     120
ggataaatag ttaatatttt taataattat ttaaaaagcc gtatctacta aaatgatttt    180
tatttggttg aaaatattaa tatgtttaaa taacacaatc tatcaaaatt aaactaaaaa    240
aaaaataagt gtacgtggtt aacattagta cagtaatata agaggaaaat gagaaattaa    300
gaaattgaaa gcgagtctaa tttttaaatt atgaacctgc atatataaaa ggaaagaaag    360
aatccaggaa gaaagaaat gaaaccatgc atggtcccct cgtcatcacg agtttctgcc      420
atttgcaata gaaacactga aacacctttc tctttgtcac ttaattgaga tgccgaagcc    480
acctcacacc atgaacttca tgaggtgtag cacccaaggc ttccatagcc atgcatactg    540
aagaatgtct caagctcagc accctacttc tgtgacgttg tccctcattc accttcctct    600
cttccctata ataaccacg cctcaggttc tccgcttcac aactcaaaca ttctcctcca     660
ttggtcctta aacactcatc agtcatcacc                                    690

<210> SEQ ID NO 7
<211> LENGTH: 588
<212> TYPE: DNA
<213> ORGANISM: Glycine max

<400> SEQUENCE: 7
aggttgaagg tgaagtttag ggttttgcaa tgaagatgat gatgcaacag tgctgcaagt     60
gaaggaattg ttagtggggt gtgtgttaga gagggagagt gtgacggggg tgttgttata    120
tagcaaaagt ggagttgttg ggtgatgaca cgtacatgat acatggtgag taggggcttt    180
gcatgaggaa caggttcag tttgccctcg gtttagtaca tcagaaaaat taaagtgggg    240 tacataaaatt atgacagaca aatgagaata atatacttt taacattttt attaaggaca   300
```

```
gttgggatac agtttcgcag gtggtgttgg tggtattttt catcataatt ggagttttac    360
ttcacaaaat ctgcattagc atttaatgaa attagtttgt aatccgtgca tcgtttgtaa    420
atttttttgc atatatattt atttgttttg taaagtaaaa ataaaatgaa aatttatgtg    480
caaattaaaa tagattaaac attgataata tatttacata gtagataaat tgttcagaaa    540
agcaagaaag ataaacacta ttatcaagaa gtatcagttt aacattcc                 588

<210> SEQ ID NO 8
<211> LENGTH: 940
<212> TYPE: DNA
<213> ORGANISM: Brassica napus

<400> SEQUENCE: 8
tctagaactt tcgggataaa gcaatcacct ggcgattcaa cgtggtcgga tcatgacgtt     60
cccagaagac atcgagtaag ctctcgaagc tgacctcttg cggatcgtac tgaacccgaa    120
caatctcgtt atgtcccgtc gtctccgaac agacatcctc gtatctcgga ttatcgacta    180
atccatggct ataccccaacc tccgtcttcg tcacgcctgg aaccctctgg tacgccaatt    240
ccgctcccca gaaacaaccg gcgccgaatt gcgcgaattg ctgacctggg agacggaaca    300
tcgtcgtcgg gtccttgcgc gattgcggcg gaagccgggt cgggttgggg acgaaaccga    360
atccgagcct ggtgaatagg ttgttcatcg gagatttata gacggagatg gatctagcgt    420
tttgggaaag ggaagtggtt tggctctttt ggatagagag agtgcagctt tggagagaga    480
ctggagaggt ttagagagag acgcggcgga gattaccgga ggagaggcga cgagagatag    540
cattatcgaa gggaagggag aaagagtgac gtggagaaat aagaaaccgt taagagtcgg    600
atatttatta tattaaaagc ccaatgggcc taaacccatt taaacaagac aagataaatg    660
ggccgtgtgg taacagagtg ttacgttcgg cttcaaatgc caacgccata ggaacaaaac    720
aaacgtgtcc tcaagtaaac ccctgccgtt tacacctcaa tgactgcatg gtgaagccat    780
taacacgtgg cgtaggatgc atgacgacgc cattgacacc tgactttctt cccttctctt    840
catatatctc taatcaattc aactactcac agtcatagct attcggaaaa tacatacaca    900
tccttttctc ttcgatctct ctcaattcac aagaagcaaa                         940

<210> SEQ ID NO 9
<211> LENGTH: 252
<212> TYPE: DNA
<213> ORGANISM: Agrobacterium tumefaciens

<400> SEQUENCE: 9
atcgttcaaa catttggcaa taaagttcct taagattgaa tcctgttgcc ggtcttgcga     60
tgattatcat ataattcctg ttgaattacg ttaagcatgt aataattaac atgtaatgca    120
tgacgttatt tatgagatgg ttttttatga ttagagtccc gcaattatac atttaatacg    180
cgatagaaaa caaatatatag cgcgcaaact aggataaatt atcgcgcgcg gtgtcatcta    240
tgttactaga tc                                                        252

<210> SEQ ID NO 10
<211> LENGTH: 300
<212> TYPE: DNA
<213> ORGANISM: Phaseolus vulgaris

<400> SEQUENCE: 10
ggctcaccca tctcaaccca cacacaaaca cattgccttt tcttcatca tcaccacaac      60
```

```
cacctgtata tattcattct cttccgccac ctcaatttct tcacttcaac acacgtcaac    120
ctgcatatgc gtgtcatccc atgcccaaat ctccatgcat gttccaacca ccttctctct    180
tatataatac ctataaatac ctctaatatc actcacttct ttcatcatcc atccatccag    240
agtactacta ctctactact ataataccc aacccaactc atattcaata ctactctact    300

<210> SEQ ID NO 11
<211> LENGTH: 360
<212> TYPE: DNA
<213> ORGANISM: Brassica napus

<400> SEQUENCE: 11
gtgctgaatc tatcacacta gaaaaaaaca tttcttcaag gtaatgactt gtggactatg     60
ttctgaaatc tcattaagtt tttatttttt gaagtttaag ttttttacttc tgtttttcga   120 aatatatcgt tcataagatg tcacgccagg acatgagcta cacatcgcac atagcacgtc   180
agatcaggac gatttgtcac tcacttcaaa cacctaagag cttctctctc acagcgcaca   240
cacatatgca tgcaatattt acacgtgatc gccatgcaaa tctccattct cacctataaa   300
ttagagcctc ggcttcactc tttactcaaa ccaaaactca tcactacaga acatacacaa   360

<210> SEQ ID NO 12
<211> LENGTH: 688
<212> TYPE: DNA
<213> ORGANISM: Vicia faba

<400> SEQUENCE: 12
ctgcagcaaa tttacacatt gccactaaac gtctaaaccc ttgtaatttg tttttgtttt     60
actatgtgtg ttatgtattt gatttgcgat aaatttttat atttggtact aaatttataa   120 cacctttat gctaacgttt gccaacactt agcaatttgc aagttgatta attgattcta    180
aattattttt gtcttctaaa tacatatact aatcaactgg aaatgtaaat atttgctaat   240
atttctacta taggagaatt aaagtgagtg aatatggtac cacaaggttt ggagatttaa   300
ttgttgcaat gctgcatgga tggcatatac accaaacatt caataattct tgaggataat   360
aatggtacca cacaagattt gaggtgcatg aacgtcacgt ggacaaaagg tttagtaatt   420
tttcaagaca acaatgttac cacacacaag ttttgaggtg catgcatgga tgcccctgtg   480
gaaagtttaa aaatatttg gaaatgattt gcatggaagc catgtgtaaa accatgacat   540
ccacttggag gatgcaataa tgaagaaaac tacaaattta catgcaacta gttatgcatg   600
tagtctatat aatgaggatt ttgcaatact ttcattcata cacactcact aagttttaca   660
cgattataat ttcttcatag ccagtcaa                                      688

<210> SEQ ID NO 13
<211> LENGTH: 2356
<212> TYPE: DNA
<213> ORGANISM: Artificial Sequence
<220> FEATURE:
<223> OTHER INFORMATION: synthetic construct-SPD1 RNAi construct

<400> SEQUENCE: 13
gggggtcgac ctgcagcagc agcaaattta cacattgcca ctaaacgtct aaacccttgt     60
aatttgtttt tgttttacta tgtgtgttat gtatttgatt tgcgataaat ttttatattt    120
ggtactaaat ttataacacc ttttatgcta acgtttgcca acacttagca atttgcaagt    180
tgattaattg attctaaatt attttttgtct tctaaataca tatactaatc aactggaaat   240
gtaaatattt gctaatattt ctactatagg agaattaaag tgagtgaata tggtaccaca   300
```

```
aggtttggag atttaattgt tgcaatgctg catggatggc atatacacca aacattcaat      360
aattcttgag gataataatg gtaccacaca agatttgagg tgcatgaacg tcacgtggac      420
aaaaggttta gtaattttc aagacaacaa tgttaccaca cacaagtttt gaggtgcatg       480
catggatgcc cctgtggaaa gtttaaaaat attttggaaa tgatttgcat ggaagccatg      540
tgtaaaacca tgacatccac ttggaggatg caataatgaa gaaaactaca aatttacatg      600
caactagtta tgcatgtagt ctatataatg aggattttgc aatactttca ttcatacaca     660
ctcactaagt tttacacgat tataatttct tcatagccag tcaaccgaca ctagaaccag      720
caatgatccg aggtaaaagc ttatgctcaa ccaaagtcct aaccacacca acatgaaacg      780
caccaagaga agccccacca ctcaaaagca aagccgttct accaaaggca tgccgtgttt     840
cgtgcataaa ggaaagcttc tcttccaaag aaagctcctc tgagtcagag ttacagacca     900
ttctcaactg agtagagacc tcatcgatat actctttgat atgtctagga acctgaagtc     960
tacctttatg aagctccgag ttacacatat taccaagatt cctcccgacg aaaacggcaa    1020
gaaaagcag tcttacttcc atgatttctt taactatgcc ggaatccatc gcagcgtaat     1080
gctctacacc acgccgaaca cctgggtgga cgatatcacc gtggtgacgc atgtcgcgca    1140
agactgtaac cacgcgtctg ttgactggca ggtggtggcc aatggtgatg tcagcgttga    1200
actgcgtgat gcggatcaac aggtggttgc aactggacaa ggcactagcg ggactttgca    1260
agtggtgaat ccgcacctct ggcaaccggg tgaaggttat ctctatgaac tgtgcgtcac    1320
agccaaaagc cagacagagt gtgatatcta cccgcttcgc gtcggcatcc ggtcagtggc    1380
agtgaagggc caacagttcc tgattaacca caaaccgttc tactttactg ctttggtcg    1440
tcatgaagat gcggacttca cgtggcaaag gattcgataa cgtgctgatg gtgcacgacc    1500
acgcattaat ggactggatt ggggccaact cctaccgtac ctcgcattac ccttacgctg    1560
aagagatgct cgactgggca gatgaacatg gcatcgtggt gattgatgaa actgctgctg    1620
tcggctttaa cctctcttta ggcattggtt acgaagcggg caacaagccg aaagaactgt    1680
acagcgaaga ggcagtcaac ggggaaactc agcaagcgca cttacaggcg attaaagagc    1740
tgatagcgcg tgacaaaaac cacccaagcg tggtgatgtg gagtattgcc aacgaaccgg    1800
ataccccgtcg aggaatcttg gtaatatgtg taactcggag cttcataaag gtagacttca    1860
ggttcctaga catatcaaag agtatatcga tgaggtctct actcagttga gaatggtctg    1920
taactctgac tcagaggagc tttctttgga agagaagctt tcctttatgc acgaaacacg    1980
gcatgccttt ggtagaacgg ctttgctttt gagtggtggg gcttctcttg gtgcgtttca    2040
tgttggtgtg gttaggactt tggttgagca taagctttta cctcggatca ttgctggttc    2100
tagtgtcggg tttcttaaga ttgaatcctg ttgccggtct tgcgatgatt atcatataat    2160
ttctgttgaa ttacgttaag catgtaataa ttaacatgta atgcatgacg ttatttatga    2220
gatgggtttt tatgattaga gtcccgcaat tatacattta atacgcgata gaaaacaaaa    2280
tatagcgcgc aaactaggat aaattatcgc gcgcggtgtc atctatgtta ctagatcggg    2340
ttcgaatcta gagggg                                                     2356
```

<210> SEQ ID NO 14  
<211> LENGTH: 11429  
<212> TYPE: DNA  
<213> ORGANISM: Artificial Sequence  
<220> FEATURE:  
<223> OTHER INFORMATION: synthetic construct

<400> SEQUENCE: 14

```
aattcgagct cggtaccggt accgagctcg aattcgattc ggagctctct tcatcggtga      60
ttgattcctt taaagactta tgtttcttat cttgcttctg aggcaagtat tcagttacca     120
gttaccactt atattctgga ctttctgact gcatcctcat ttttccaaca ttttaaattt     180
cactattggc tgaatgcttc ttctttgagg aagaaacaat tcagatggca gaaatgtatc     240
aaccaatgca tatatacaaa tgtacctctt gttctcaaaa catctatcgg atggttccat     300
ttgctttgtc atccaattag tgactacttt atattattca ctcctcttta ttactatttt     360
catgcgaggt tgccatgtac attatatttg taaggattga cgctattgag cgttttttctt    420
caattttctt tattttagac atgggtatga aatgtgtgtt agagttgggt tgaatgagat     480
atacgttcaa gtgaagtggc ataccgttgt cgagtaagga tgacctaccc attcttgaga     540
caaatgttac attttagtat cagagtaaaa tgtgtaccta taactcaaat tcgattgaca     600
tgtatccatt caacataaaa ttaaaccagc ctgcacctgc atccacattt caagtatttt     660
caaaccgttc ggctcctatc caccgggtgt aacaagacgg attccgaatt tggaagattt     720
tgactcaaat tcccaattta tattgaccgt gactaaatca actttaactt ctataattct     780
gattaagctc ccaatttata ttcccaacgg cactacctcc aaaatttata gactctcatc     840
ccctttaaaa ccaacttagt aaacgttttt ttttttaatt ttatgaagtt aagttttttac    900
cttgttttta aaagaatcg ttcataagat gccatgccag aacattagct acacgttaca     960
catagcatgc agccgcggag aattgttttt cttcgccact tgtcactccc ttcaaacacc    1020
taagagcttc tctctcacag cacacacata caatcacatg cgtgcatgca ttattacacg    1080
tgatcgccat gcaaatctcc tttatagcct ataaattaac tcatccgctt cactctttac    1140
tcaaaccaaa actcatcaat acaaacaaga ttaaaaacat accccatgag gtcttccaag    1200
aatgttatca aggagttcat gaggtttaag gttcgcatgg aaggaacggt caatgggcac    1260
gagtttgaaa tagaaggcga aggagagggg aggccatacg aaggcacaa taccgtaaag     1320
cttaaggtaa ccaagggggg acctttgcca tttgcttggg atattttgtc accacaattt    1380
cagtatggaa gcaaggtata tgtcaagcac cctgccgaca taccagacta taaaaagctg    1440
tcatttcctg aaggatttaa atgggaaagg gtcatgaact ttgaagacgg tggcgtcgtt    1500
actgtaaccc aggattccag tttgcaggat ggctgtttca tctacaaggt caagttcatt    1560
ggcgtgaact ttccttccga tggacctgtt atgcaaaaga agacaatggg ctgggaagcc    1620
agcactgagc gtttgtatcc tcgtgatggc gtgttgaaag gagagattca taaggctctg    1680
aagctgaaag acggtggtca ttacctagtt gaattcaaaa gtatttacat ggcaaagaag    1740
cctgtgcagc taccagggta ctactatgtt gactccaaac tggatataac aagccacaac    1800
gaagactata caatcgttga gcagtatgaa agaaccgagg acgccacca tctgttcctt     1860
atgtacaagt aagaattcgg atccgggccc ggcgcgccgt cgacactagt gtttaaaccc    1920
atggctgcag ttcgaatcta gagcccgggc tcctcagcag gcctatttaa atgcgatcgc    1980
cacgtgggat ccctcggagg ctctcaagat caaaggctta aaaagctggg gttttatgaa    2040
tgggatcaaa gttctttttt ttcttttata tttgcttctc catttgtttg tttcatttcc    2100
cttttttgttt tcgtttctat gatgcacttg tgtgtgacaa actctctggg tttttactta    2160
cgtctgcgtt tcaaaaaaaa aaaccgcttt cgttttgcgt tttagtccca ttgttttgta    2220
gctctgagtg atcgaattga tgcctcttta ttccttttgt tccctataat ttcttttcaaa    2280
actcagaaga aaaaccttga aactctttgc aatgttaata taagtattgt ataagatttt    2340
```

```
tattgatttg gttattagtc ttacttttgc tacctccatc ttcacttgga actgatattc   2400
tgaatagtta aagcgttaca tgtcttccat tcacaaatga acttaaacta gcacaaagtc   2460
agatatttta agaccgcggg agctcaagct tggatcctct agagtcgacc tgcaggcatg   2520
caagcttggc actggccgtc gttttacaac gtcgtgactg ggaaaaccct ggcgttaccc   2580
aacttaatcg ccttgcagca catccccctt tcgccagctg gcgtaatagc gaagaggccc   2640
gcaccgatcg cccttcccaa cagttgcgca gcctgaatgg cgaatgctag agcagcttga   2700
gcttggatca gattgtcgtt tcccgccttc agtttaaact atcagtgttt gacaggatat   2760
attggcgggt aaacctaaga gaaaagagcg tttattagaa taacggatat ttaaaagggc   2820
gtgaaaaggt ttatccgttc gtccatttgt atgtgcatgc caaccacagg ttcccctcg    2880
ggatcaaagt actttgatcc aaccctccg ctgctatagt gcagtcggct tctgacgttc    2940
agtgcagccg tcttctgaaa cgacatgtc gcacaagtcc taagttacgc gacaggctgc    3000
cgccctgccc ttttcctggc gttttcttgt cgcgtgtttt agtcgcataa agtgaaatac   3060
ttgcgactag aaccggagac attacgccat gaacaagagc gccgccgctg gcctgctggg   3120
ctatgcccgc gtcagcaccg acgaccagga cttgaccaac caacgggccg aactgcacgc   3180
ggccggctgc accaagctgt tttccgagaa gatcaccggc accaggcgcg accgcccgga   3240
gctggccagg atgcttgacc acctacgccc tggcgacgtt gtgacagtga ccaggctaga   3300
ccgcctggcc cgcagcaccc gcgacctact ggacattgcc gagcgcatcc aggaggccgg   3360
cgcgggcctg cgtagcctgg cagagccgtg ggccgacacc accacgccgg ccggccgcat   3420
ggtgttgacc gtgttcgccg gcattgccga gttcgagcgt tccctaatca tcgaccgcac   3480
ccggagcggg cgcgaggccg ccaaggcccg aggcgtgaag tttggccccc gccctaccct   3540
caccccggca cagatcgcgc acgccgcgcga gctgatcgac caggaaggcc gcaccgtgaa   3600
agaggcggct gcactgcttg gcgtgcatcg ctcgaccctg taccgcgcac ttgagcgcag   3660
cgaggaagtg acgcccaccg aggccaggcg gcgcggtgcc ttccgtgagg acgcattgac   3720
cgaggccgac gccctggcgg ccgccagaaa tgaacgccaa gaggaacaag catgaaaccg   3780
caccaggacg gccaggacga accgtttttc attaccgaag agatcgaggc ggagatgatc   3840
gcggccgggt acgtgttcga gccgcccgcg cacgtctcaa ccgtgcggct gcatgaaatc   3900
ctggccggtt tgtctgatgc caagctggcg gcctggccgg ccagcttggc cgctgaagaa   3960
accgagcgcc gccgtctaaa aaggtgatgt gtatttgagt aaaacagctt gcgtcatgcg   4020
gtcgctgcgt atatgatgcg atgagtaaat aaacaaatac gcaaggggaa cgcatgaagg   4080
ttatcgctgt acttaaccag aaaggcgggt caggcaagac gaccatcgca acccatctag   4140
cccgcgccct gcaactcgcc ggggccgatg ttctgttagt cgattccgat ccccagggca   4200
gtgcccgcga ttgggcggcc gtgcgggaag atcaaccgct aaccgttgtc ggcatcgacc   4260
gcccgacgat tgaccgcgac gtgaaggcca tcggccggcg cgacttcgta gtgatcgacg   4320
gagcgcccca ggcggcggac ttggctgtgt ccgcgatcaa ggcagccgac ttcgtgctga   4380
ttccggtgca gccaagccct tacgacatat gggccaccgc cgacctggtg gagctggtta   4440
agcagcgcat tgaggtcacg gatggaaggc tacaagcggc ctttgtcgtg tcgcgggcga   4500
tcaaaggcac gcgcatcggc ggtgaggttg ccgaggcgct ggccgggtac gagctgccca   4560
ttcttgagtc ccgtatcacg cagcgcgtga gctaccagg cactgccgcc gccggacacaa   4620
ccgttcttga atcagaaccc gagggcgacg ctgcccgcga ggtccaggcg ctggccgctg   4680
```

```
aaattaaatc aaaactcatt tgagttaatg aggtaaagag aaaatgagca aaagcacaaa      4740
cacgctaagt gccggccgtc cgagcgcacg cagcagcaag gctgcaacgt tggccagcct      4800
ggcagacacg ccagccatga agcgggtcaa ctttcagttg ccggcggagg atcacaccaa      4860
gctgaagatg tacgcggtac gccaaggcaa gaccattacc gagctgctat ctgaatacat      4920
cgcgcagcta ccagagtaaa tgagcaaatg aataaatgag tagatgaatt ttagcggcta      4980
aaggaggcgg catggaaaat caagaacaac caggcaccga cgccgtggaa tgccccatgt      5040
gtggaggaac gggcggttgg ccaggcgtaa gcggctgggt tgtctgccgg ccctgcaatg      5100
gcactggaac ccccaagccc gaggaatcgg cgtgacggtc gcaaaccatc cggcccggta      5160
caaatcggcg cggcgctggg tgatgacctg gtggagaagt tgaaggccgc gcaggccgcc      5220
cagcggcaac gcatcgaggc agaagcacgc cccggtgaat cgtggcaagc ggccgctgat      5280
cgaatccgca aagaatcccg gcaaccgccg gcagccggtg cgccgtcgat taggaagccg      5340
cccaagggcg acgagcaacc agattttttc gttccgatgc tctatgacgt gggcacccgc      5400
gatagtcgca gcatcatgga cgtggccgtt ttccgtctgt cgaagcgtga ccgacgagct      5460
ggcgaggtga tccgctacga gcttccagac gggcacgtag aggtttccgc agggccggcc      5520
ggcatggcca gtgtgtggga ttacgacctg gtactgatgg cggtttccca tctaaccgaa      5580
tccatgaacc gataccggga agggaaggga gacaagcccg ccgcgtgtt ccgtccacac       5640 gttgcggacg tactcaagtt ctgccggcga gccgatggcg gaaagcagaa agacgacctg      5700
gtagaaacct gcattcggtt aaacaccacg cacgttgcca tgcagcgtac gaagaaggcc      5760
aagaacggcc gcctggtgac ggtatccgag ggtgaagcct tgattagccg ctacaagatc      5820
gtaaagagcg aaaccgggcg gccggagtac atcgagatcg agctagctga ttggatgtac      5880
cgcgagatca cagaaggcaa gaacccggac gtgctgacgg ttcaccccga ttactttttg      5940
atcgatcccg gcatcggccg ttttctctac cgcctggcac gccgcgccgc aggcaaggca      6000
gaagccagat ggttgttcaa gacgatctac gaacgcagtg gcagcgccgg agagttcaag      6060
aagttctgtt tcaccgtgcg caagctgatc gggtcaaatg acctgccgga gtacgatttg      6120
aaggaggagg cggggcaggc tggcccgatc ctagtcatgc gctaccgcaa cctgatcgag      6180
ggcgaagcat ccgccggttc ctaatgtacg gagcagatgc tagggcaaat tgccctagca      6240
ggggaaaaag gtcgaaaagg tctctttcct gtggatagca cgtacattgg aacccaaag       6300 ccgtacattg ggaaccggaa cccgtacatt gggaacccaa agccgtacat tgggaaccgg      6360
tcacacatgt aagtgactga tataaaagag aaaaaaggcg atttttccgc ctaaaactct      6420
ttaaaactta ttaaaactct taaaacccgc ctggcctgtg cataactgtc tggccagcgc      6480
acagccgaag agctgcaaaa agcgcctacc cttcggtcgc tgcgctccct acgccccgcc      6540
gcttcgcgtc ggcctatcgc ggccgctggc cgctcaaaaa tggctggcct acggccaggc      6600
aatctaccag ggcgcggaca agccgcgccg tcgccactcg accgccggcg cccacatcaa      6660
ggcaccctgc ctcgcgcgtt tcggtgatga cgtgaaaac ctctgacaca tgcagctccc       6720
ggagacggtc acagcttgtc tgtaagcgga tgccgggagc agacaagccc gtcagggcgc      6780
gtcagcgggt gttggcgggt gtcggggcgc agccatgacc cagtcacgta gcgatagcgg      6840
agtgtatact ggcttaacta tgcggcatca gagcagattg tactgagagt gcaccatatg      6900
cggtgtgaaa taccgcacag atgcgtaagg agaaaatacc gcatcaggcg ctcttccgct      6960
tcctcgctca ctgactcgct gcgctcggtc gttcggctgc ggcgagcggt atcagctcac      7020
tcaaaggcgg taatacggtt atccacagaa tcagggata acgcaggaaa gaacatgtga      7080
```

```
gcaaaaggcc agcaaaaggc caggaaccgt aaaaaggccg cgttgctggc gttttttccat    7140 aggctccgcc cccctgacga gcatcacaaa aatcgacgct caagtcagag gtggcgaaac    7200
ccgacaggac tataaagata ccaggcgttt ccccctggaa gctccctcgt gcgctctcct    7260
gttccgaccc tgccgcttac cggatacctg tccgcctttc tcccttcggg aagcgtggcg    7320
ctttctcata gctcacgctg taggtatctc agttcggtgt aggtcgttcg ctccaagctg    7380
ggctgtgtgc acgaaccccc cgttcagccc gaccgctgcg ccttatccgg taactatcgt    7440
cttgagtcca acccggtaag acacgactta tcgccactgg cagcagccac tggtaacagg    7500
attagcagag cgaggtatgt aggcggtgct acagagttct tgaagtggtg gcctaactac    7560
ggctacacta aaggacagt atttggtatc tgcgctctgc tgaagccagt taccttcgga    7620
aaaagagttg gtagctcttg atccggcaaa caaaccaccg ctggtagcgg tggtttttttt    7680 gtttgcaagc agcagattac gcgcagaaaa aaaggatctc aagaagatcc tttgatcttt    7740
tctacggggt ctgacgctca gtggaacgaa aactcacgtt aagggatttt ggtcatgcat    7800
tctaggtact aaaacaattc atccagtaaa atataatatt ttatttctc ccaatcaggc    7860 ttgatcccca gtaagtcaaa aaatagctcg acatactgtt cttccccgat atcctccctg    7920
atcgaccgga cgcagaaggc aatgtcatac ccttgtccg ccctgccgct tctcccaaga    7980
tcaataaagc cacttacttt gccatctttc acaaagatgt tgctgtctcc caggtcgccg    8040
tgggaaaaga caagttcctc ttcgggcttt tccgtcttta aaaaatcata cagctcgcgc    8100
ggatctttaa atggagtgtc ttcttcccag ttttcgcaat ccacatcggc cagatcgtta    8160
ttcagtaagt aatccaattc ggctaagcgg ctgtctaagc tattcgtata gggacaatcc    8220
gatatgtcga tggagtgaaa gagcctgatg cactccgcat acagctcgat aatcttttca    8280
gggctttgtt catcttcata ctcttccgag caaaggacgc catcggcctc actcatgagc    8340
agattgctcc agccatcatg ccgttcaaag tgcaggacct ttggaacagg cagctttcct    8400
tccagccata gcatcatgtc cttttcccgt tccacatcat aggtggtccc tttataccgg    8460
ctgtccgtca tttttaaata taggttttca ttttctccca ccagcttata taccttagca    8520
ggagacattc cttccgtatc ttttacgcag cggtattttt cgatcagttt tttcaattcc    8580
ggtgatattc tcattttagc catttattat ttccttcctc ttttctacag tatttaaaga    8640 tacccccaaga agctaattat aacaagacga actccaattc actgttcctt gcattctaaa    8700
accttaaata ccagaaaaca gctttttcaa agttgttttc aaagttggcg tataacatag    8760
tatcgacgga gccgattttg aaaccgcggt gatcacaggc agcaacgctc tgtcatcgtt    8820
acaatcaaca tgctaccctc cgcgagatca tccgtgtttc aaacccggca gcttagttgc    8880
cgttcttccg aatagcatcg gtaacatgag caaagtctgc cgccttacaa cggctctccc    8940
gctgacgccg tcccggactg atgggctgcc tgtatcgagt ggtgattttg tgccgagctg    9000
ccggtcgggg agctgttggc tggctggtgg caggatatat tgtggtgtaa acaaattgac    9060
gcttagacaa cttaataaca cattgcggac gttttaatg tactgaatta acgccgaatt    9120
aattcggggg atctggattt tagtactgga ttttggtttt aggaattaga aattttattg    9180
atagaagtat tttacaaata caaatacata ctaagggttt cttatatgct caacacatga    9240
gcgaaaccct ataggaaccc taattccctt atctgggaac tactcacaca ttattatgga    9300
gaaactcgag cttgtcgatc gacagatccg gtcggcatct actctatttc tttgccctcg    9360
gacgagtgct ggggcgtcgg tttccactat cggcgagtac ttctacacag ccatcggtcc    9420
```

-continued

```
agacggccgc gcttctgcgg gcgatttgtg tacgcccgac agtcccggct ccggatcgga    9480
cgattgcgtc gcatcgaccc tgcgcccaag ctgcatcatc gaaattgccg tcaaccaagc    9540
tctgatagag ttggtcaaga ccaatgcgga gcatatacgc ccggagtcgt ggcgatcctg    9600
caagctccgg atgcctccgc tcgaagtagc gcgtctgctg ctccatacaa gccaaccacg    9660
gcctccagaa gaagatgttg cgacctcgt attgggaatc cccgaacatc gcctcgctcc    9720
agtcaatgac cgctgttatg cggccattgt ccgtcaggac attgttggag ccgaaatccg    9780
cgtgcacgag gtgccggact tcggggcagt cctcggccca agcatcagc tcatcgagag    9840 cctgcgcgac ggacgcactg acggtgtcgt ccatcacagt ttgccagtga tacacatggg    9900
gatcagcaat cgcgcatatg aaatcacgcc atgtagtgta ttgaccgatt ccttgcggtc    9960
cgaatgggcc gaacccgctc gtctggctaa gatcggccgc agcgatcgca tccatagcct   10020
ccgcgaccgg ttgtagaaca gcgggcagtt cggtttcagg caggtcttgc aacgtgacac   10080
cctgtgcacg gcgggagatg caataggtca ggctctcgct aaactcccca atgtcaagca   10140
cttccggaat cgggagcgcg gccgatgcaa agtgccgata acataacga tctttgtaga   10200 aaccatcggc gcagctattt acccgcagga catatccacg ccctcctaca tcgaagctga   10260
aagcacgaga ttcttcgccc tccgagagct gcatcaggtc ggagacgctg tcgaactttt   10320
cgatcagaaa cttctcgaca gacgtcgcgg tgagttcagg cttttttcata tctcattgcc   10380 cccgggatc tgcgaaagct cgagagagat agatttgtag agagagactg gtgatttcag   10440
cgtgtcctct ccaaatgaaa tgaacttcct tatatagagg aaggtcttgc gaaggatagt   10500
gggattgtgc gtcatccctt acgtcagtgg agatatcaca tcaatccact tgctttgaag   10560
acgtggttgg aacgtcttct ttttccacga tgctcctcgt gggtgggggt ccatctttgg   10620
gaccactgtc ggcagaggca tcttgaacga tagccttttcc tttatcgcaa tgatggcatt   10680
tgtaggtgcc accttccttt tctactgtcc ttttgatgaa gtgacagata gctgggcaat   10740
ggaatccgag gaggtttccc gatattaccc tttgttgaaa agtctcaata gcccttggt   10800 cttctgagac tgtatctttg atattcttgg agtagacgag agtgtcgtgc tccaccatgt   10860
tatcacatca atccacttgc tttgaagacg tggttggaac gtcttctttt tccacgatgc   10920
tcctcgtggg tggggtgtcca tctttgggac cactgtcggc agaggcatct tgaacgatag   10980
cctttccttt atcgcaatga tggcatttgt aggtgccacc ttccttttct actgtccttt   11040
tgatgaagtg acagatagct gggcaatgga atccgaggag gtttcccgat attaccctt    11100 gttgaaaagt ctcaatagcc ctttggtctt ctgagactgt atctttgata ttcttggagt   11160
agacgagagt gtcgtgctcc accatgttgg caagctgctc tagccaatac gcaaaccgcc   11220 tctcccgcg cgttggccga ttcattaatg cagctggcac gacaggtttc ccgactggaa   11280
agcgggcagt gagcgcaacg caattaatgt gagttagctc actcattagg caccccaggc   11340
tttacacttt atgcttccgg ctcgtatgtt gtgtggaatt gtgagcggat aacaatttca   11400
cacaggaaac agctatgacc atgattacg                                     11429
```

<210> SEQ ID NO 15
<211> LENGTH: 1168
<212> TYPE: DNA
<213> ORGANISM: Brassica napus

<400> SEQUENCE: 15

```
ggtaccgagc tcgaattcga ttcggagctc tcttcatcgg tgattgattc ctttaaagac      60 ttatgttct tatcttgctt ctgaggcaag tattcagtta ccagttacca cttatattct     120
```

```
ggactttctg actgcatcct cattttttcca acatttttaaa tttcactatt ggctgaatgc      180
ttcttctttg aggaagaaac aattcagatg gcagaaatgt atcaaccaat gcatatatac      240
aaatgtacct cttgttctca aaacatctat cggatggttc catttgcttt gtcatccaat      300
tagtgactac tttatattat tcactcctct ttattactat tttcatgcga ggttgccatg      360
tacattatat ttgtaaggat tgacgctatt gagcgttttt cttcaatttt ctttatttta      420
gacatgggta tgaaatgtgt gttagagttg ggttgaatga gatatacgtt caagtgaagt      480
ggcataccgt tgtcgagtaa ggatgaccta cccattcttg agacaaatgt tacatttttag     540 tatcagagta aaatgtgtac ctataactca aattcgattg acatgtatcc attcaacata      600
aaattaaacc agcctgcacc tgcatccaca tttcaagtat tttcaaaccg ttcggctcct      660
atccaccggg tgtaacaaga cggattccga atttggaaga ttttgactca aattcccaat      720
ttatattgac cgtgactaaa tcaactttaa cttctataat tctgattaag ctcccaattt      780
atattcccaa cggcactacc tccaaaattt atagactctc atccccttt aaaccaactt      840 agtaaacgtt tttttttttta attttatgaa gttaagtttt taccttgttt ttaaaaagaa     900
tcgttcataa gatgccatgc cagaacatta gctacgtt acacatagca tgcagccgcg       960
gagaattgtt tttcttcgcc acttgtcact cccttcaaac acctaagagc ttctctctca    1020
cagcacacac atacaatcac atgcgtgcat gcattattac acgtgatcgc catgcaaatc    1080
tcctttatag cctataaatt aactcatccg cttcactctt tactcaaacc aaaactcatc   1140
aatacaaaca agattaaaaa catacccc                                       1168
```

<210> SEQ ID NO 16
<211> LENGTH: 687
<212> TYPE: DNA
<213> ORGANISM: artificial sequence
<220> FEATURE:
<223> OTHER INFORMATION: synthetic construct

<400> SEQUENCE: 16

```
atgaggtctt ccaagaatgt tatcaaggag ttcatgaggt ttaaggttcg catggaagga       60
acggtcaatg ggcacgagtt tgaaatagaa ggcgaaggag aggggaggcc atacgaaggc      120
cacaataccg taaagcttaa ggtaaccaag gggggacctt tgccatttgc ttgggatatt      180
ttgtcaccac aatttcagta tggaagcaag gtatatgtca agcaccctgc cgacatacca      240
gactataaaa agctgtcatt tcctgaagga tttaaatggg aaagggtcat gaactttgaa      300
gacggtggcg tcgttactgt aacccaggat tccagtttgc aggatggctg tttcatctac      360
aaggtcaagt tcattggcgt gaactttcct tccgatggac ctgttatgca aaagaagaca      420
atgggctggg aagccagcac tgagcgtttg tatcctcgtg atggcgtgtt gaaggagag       480 attcataagg ctctgaagct gaaagacggt ggtcattacc tagttgaatt caaaagtatt      540
tacatggcaa agaagcctgt gcagctacca gggtactact atgttgactc caaactggat      600
ataacaagcc acaacgaaga ctatacaatc gttgagcagt atgaaagaac cgagggacgc     660
caccatctgt tccttatgta caagtaa                                          687
```

<210> SEQ ID NO 17
<211> LENGTH: 138
<212> TYPE: DNA
<213> ORGANISM: Artificial Sequence
<220> FEATURE:
<223> OTHER INFORMATION: synthetic construct

<400> SEQUENCE: 17

```
gaattcggat ccgggcccgg cgcgccgtcg acactagtgt ttaaacccat ggctgcagtt      60
cgaatctaga gcccgggctc ctcagcaggc ctatttaaat gcgatcgcca cgtgggatcc     120
ctcggaggct ctcaagat                                                   138
```

<210> SEQ ID NO 18
<211> LENGTH: 481
<212> TYPE: DNA
<213> ORGANISM: Arabidopsis thaliana

<400> SEQUENCE: 18

```
caaaggctta aaaagctggg gttttatgaa tgggatcaaa gtttcttttt ttcttttata     60
tttgcttctc catttgtttg tttcatttcc cttttttgttt tcgtttctat gatgcacttg    120
tgtgtgacaa actctctggg ttttttactta cgtctgcgtt tcaaaaaaaa aaaccgcttt    180
cgttttgcgt tttagtccca ttgttttgta gctctgagtg atcgaattga tgcctcttta    240
ttccttttgt tccctataat ttcttcaaa actcagaaga aaaaccttga aactctttgc     300
aatgttaata taagtattgt ataagatttt tattgatttg gttattagtc ttacttttgc    360
tacctccatc ttcacttgga actgatattc tgaatagtta aagcgttaca tgtcttccat    420
tcacaaatga acttaaacta gcacaaagtc agatatttta agaccgcggg agctcaagct    480
t                                                                    481
```

<210> SEQ ID NO 19
<211> LENGTH: 2474
<212> TYPE: DNA
<213> ORGANISM: Artificial Sequence
<220> FEATURE:
<223> OTHER INFORMATION: Synthetic construct

<400> SEQUENCE: 19

```
ggtaccgagc tcgaattcga ttcggagctc tcttcatcgg tgattgattc ctttaaagac      60
ttatgttttct tatcttgctt ctgaggcaag tattcagtta ccagttacca cttatattct    120
ggactttctg actgcatcct catttttcca acattttaaa tttcactatt ggctgaatgc    180
ttcttctttg aggaagaaac aattcagatg gcagaaatgt atcaaccaat gcatatatac    240
aaatgtacct cttgttctca aaacatctat cggatggttc catttgcttt gtcatccaat    300
tagtgactac tttatattat tcactcctct ttattactat tttcatgcga ggttgccatg    360
tacattatat ttgtaaggat tgacgctatt gagcgttttt cttcaatttt ctttattta    420
gacatgggta tgaaatgtgt gttagagttg ggttgaatga gatatacgtt caagtgaagt    480
ggcataccgt tgtcgagtaa ggatgaccta cccattcttg agacaaatgt tacattttag    540
tatcagagta aaatgtgtac ctataactca aattcgattg acatgtatcc attcaacata    600
aaattaaacc agcctgcacc tgcatccaca tttcaagtat tttcaaaccg ttcggctcct    660
atccaccggg tgtaacaaga cggattccga atttggaaga ttttgactca aattcccaat    720
ttatattgac cgtgactaaa tcaactttaa cttctataat tctgattaag ctcccaattt    780
atattcccaa cggcactacc tccaaaattt atagactctc atccccttttt aaaccaactt    840
agtaaacgtt ttttttttta attttatgaa gttaagttttt taccttgttt ttaaaaagaa    900
tcgttcataa gatgccatgc cagaacatta gctacacgtt acacatagca tgcagccgcg    960
gagaattgtt tttcttcgcc acttgtcact cccttcaaac acctaagagc ttctctctca   1020
cagcacacac atacaatcac atgcgtgcat gcattattac acgtgatcgc catgcaaatc   1080
```

```
tcctttatag cctataaatt aactcatccg cttcactctt tactcaaacc aaaactcatc    1140
aatacaaaca agattaaaaa catacccat gaggtcttcc aagaatgtta tcaaggagtt    1200
catgaggttt aaggttcgca tggaaggaac ggtcaatggg cacgagtttg aaatagaagg    1260
cgaaggagag gggaggccat acgaaggcca caataccgta aagcttaagg taaccaaggg    1320
gggacctttg ccatttgctt gggatatttt gtcaccacaa tttcagtatg gaagcaaggt    1380
atatgtcaag caccctgccg acataccaga ctataaaaag ctgtcatttc ctgaaggatt    1440
taaatgggaa agggtcatga actttgaaga cggtggcgtc gttactgtaa cccaggattc    1500
cagtttgcag gatggctgtt tcatctacaa ggtcaagttc attggcgtga actttccttc    1560
cgatggacct gttatgcaaa agaagacaat gggctgggaa gccagcactg agcgtttgta    1620
tcctcgtgat ggcgtgttga aaggagagat tcataaggct ctgaagctga agacggtgg    1680 tcattaccta gttgaattca aaagtattta catggcaaag aagcctgtgc agctaccagg    1740
gtactactat gttgactcca aactggatat aacaagccac aacgaagact atacaatcgt    1800
tgagcagtat gaaagaaccg agggacgcca ccatctgttc cttatgtaca agtaagaatt    1860
cggatccggg cccggcgcgc cgtcgacact agtgtttaaa cccatggctg cagttcgaat    1920
ctagagcccg ggctcctcag caggcctatt taaatgcgat cgccacgtgg gatccctcgg    1980
aggctctcaa gatcaaaggc ttaaaaagct ggggttttat gaatgggatc aaagtttctt    2040
tttttctttt atatttgctt ctccatttgt ttgtttcatt tcccttttg ttttcgtttc    2100 tatgatgcac ttgtgtgtga caaactctct gggtttttac ttacgtctgc gtttcaaaaa    2160
aaaaaaccgc tttcgttttg cgttttagtc ccattgtttt gtagctctga gtgatcgaat    2220
tgatgcctct ttattccttt tgttccctat aatttcttttc aaaactcaga agaaaaacct    2280
tgaaactctt tgcaatgtta atataagtat tgtataagat ttttattgat ttggttatta    2340
gtcttacttt tgctacctcc atcttcactt ggaactgata ttctgaatag ttaaagcgtt    2400
acatgtcttc cattcacaaa tgaacttaaa ctagcacaaa gtcagatatt ttaagaccgc    2460
gggagctcaa gctt                                                       2474
```

COMPOSITIONS AND METHODS FOR ENGINEERING OIL CONTENT IN PLANTS

CROSS REFERENCE TO RELATED APPLICATIONS

This application claims the benefit of U.S. Provisional Application No. 62/462,624, filed Feb. 23, 2017, incorporated by reference herein in its entirety.

STATEMENT REGARDING FEDERALLY SPONSORED RESEARCH

This invention was made in part with government support from the United States Department of Energy award No. DE-000020. The government has certain rights in this invention.

SEQUENCE LISTING

A Sequence Listing, incorporated herein by reference, is submitted in electronic form as an ASCII text file, created Feb. 23, 2017, of size 40 KB, and named "7RV834302.TXT".

BACKGROUND

Plant seed oils have tremendous potential as environmentally, economically and technologically feasible replacements for petroleum, but the relatively low oil yields from existing crops limits the commercial viability of seed oil based biofuels. Therefore, a primary issue of concern with biofuels and bioproducts is the ability to produce enough feedstock oils without displacing food crops. *Camelina sativa* is a cool season, non-food oilseed crop with 30-35% oil contents in seeds. In the USA and Europe, there are serious efforts to develop Camelina as a dedicated oilseed crop, as an alternative to food oilseed crops, for production of renewable biofuels and bioproducts. Camelina oil has ideal properties for conversion into biodiesel and jet fuels. Recently, the US Navy has successfully tested its fleet, including Supersonic Fighter jets, with a 50/50 blend of Camelina-derived biofuel and conventional jet fuels.

Other oil seed crops including canola (*Brassica napus*), Indian mustard (*Brassica juncea*), *Brassica carinata*, soybean (*Glycine max*), groundnut (*Arachis hypogea*), flax, cuphea, sesame (*Sesamum indicum*), sunflower, coconut, palm, cotton (*Gossypium* sp.), safflower etc. are used for edible oils, biofuels and industrial byproducts.

Thus, there is a need to increase oil and seed yield in Camelina and other oilseed plants and to develop generally applicable methods to increase oil and seed yield in plants, particularly oilseed plants.

SUMMARY

Disclosed, in various embodiments, are compositions and methods for producing plants with enhanced oil content and higher seed yield.

A method of increasing total oil content or seed yield in a plant or in a part, cell, or propagation material thereof, comprises: expressing a first transgenic expression cassette and a second transgenic expression cassette in a plant or in a tissue, organ, part, cell or propagation material thereof, wherein the first transgenic expression cassette comprises a nucleic acid sequence encoding a diacylglyerol acyltransferase (DGAT1) operatively linked to a plant-expressible promoter and the second transgenic expression cassette comprises a nucleic acid sequence encoding a glycerol-3-phosphate dehydrogenase (GPD1) operatively linked to a plant-expressible promoter; and selecting the plant or the tissue, organ, part, cell or propagation material thereof in which the total oil content or seed yield of the plant or the total oil content in the tissue, organ, part, cell or propagation material thereof is increased in comparison with a corresponding plant or a tissue organ part, cell or propagation material thereof that is not expressing the first transgenic expression cassette and the second transgenic expression cassette.

A method of increasing total oil content or seed yield in a plant or in a tissue, organ, part, cell or propagation material thereof, comprises: expressing a transgenic expression cassette in a plant or in a tissue, organ, part, cell or propagation material thereof, wherein the transgenic expression cassette comprises a nucleic acid sequence encoding a monoacylglycerol O-acyltransferase 1 (MGAT1) operably linked to a plant-expressible promoter, a nucleic acid sequence encoding a phosphatidylcholine diacylglycerol cholinephosphotransferase 1 (PDCT1) operably linked to a plant-expressible promoter, a nucleic acid sequence encoding a suppressor of expression of endogenous Sugar Dependent 1 (SDP1) operably linked to a plant-expressible promoter or a combination thereof; and selecting the plant or the tissue, organ, part, cell or propagation material thereof in which the total oil content or seed yield of the plant or the total oil content in the tissue, organ, part, cell or propagation material thereof is increased in comparison with a corresponding plant or a tissue organ part, cell or propagation material thereof that is not expressing the transgenic expression cassette.

A method of producing a transgenic plant having increased oil content or seed yield comprises transforming a plant cell with a first transgenic expression cassette and a second transgenic expression cassette, wherein the first transgenic expression cassette comprises a nucleic acid sequence encoding a diacylglyerol acyltransferase (DGAT1) operatively linked to a plant-expressible promoter and the second transgenic expression cassette comprises a nucleic acid sequence encoding a glycerol-3-phosphate dehydrogenase (GPD1) operatively linked to a plant-expressible promoter; growing a plant from the transformed plant cell until the plant produces seed; and selecting a seed from a plant in which the oil content or the seed yield is higher than a plant of the same species not comprising the first and second expression cassettes.

A method of producing a transgenic plant having increased oil content or seed yield, comprises: transforming a plant cell with a transgenic expression cassette, wherein the transgenic expression cassette expresses a monoacylglycerol O-acyltransferase 1 (MGAT1), expresses a phosphatidylcholine diacylglycerol cholinephosphotransferase 1 (PDCT1), inhibits expression of Sugar Dependent 1 (SDP1), or a combination thereof; and growing a plant from the transformed plant cell until the plant produces seed; and selecting seeds from a plant in which the oil content or the seed yield is higher than a plant of the same species not comprising the transgenic expression cassette.

Also disclosed is a trangenic plant or a tissue, organ, part, cell, or propagation material thereof made by any of the disclosed methods.

A transgenic plant comprises a polynucleotide encoding a diacylglyerol acyltransferase (DGAT1) operatively linked to a plant-expressible promoter and a polynucleotide encoding a glycerol-3-phosphate dehydrogenase (GPD1) operatively linked to a plant-expressible promoter.

A transgenic plant comprises a polynucleotide encoding a monoacylglycerol O-acyltransferase 1 (MGAT1) operatively linked to a plant-expressible promoter; a polynucleotide encoding a phosphatidylcholine diacylglycerol cholinephosphotransferase 1 (PDCT1) operatively linked to a plant-expressible promoter; a polynucleotide encoding a suppressor of expression of Sugar Dependent 1 (SDP1) operatively linked to a plant-expressible promoter; or a combination thereof.

A transgenic expression cassette comprises a polynucleotide encoding a diacylglyerol acyltransferase (DGAT1) operatively linked to a plant-expressible promoter; a polynucleotide encoding a glycerol-3-phosphate dehydrogenase (GPD1) operatively linked to a plant-expressible promoter; a polynucleotide encoding a monoacylglycerol O-acyltransferase 1 (MGAT1) operatively linked to a plant-expressible promoter; a polynucleotide encoding a phosphatidylcholine diacylglycerol cholinephosphotransferase 1 (PDCT1) operatively linked to a plant-expressible promoter; a polynucleotide encoding a suppressor of expression of Sugar Dependent 1 (SDP1) operatively linked to a plant-expressible promoter; or a combination thereof.

A binary vector comprises SEQ ID NO:19 or SEQ ID NO:14.

These and other features and characteristics are more particularly described below.

BRIEF DESCRIPTION OF THE DRAWINGS

The following is a brief description of the drawings wherein like elements are numbered alike and which are presented for the purposes of illustrating the exemplary embodiments disclosed herein and not for the purposes of limiting the same.

DETAILED DESCRIPTION

Figure 1:
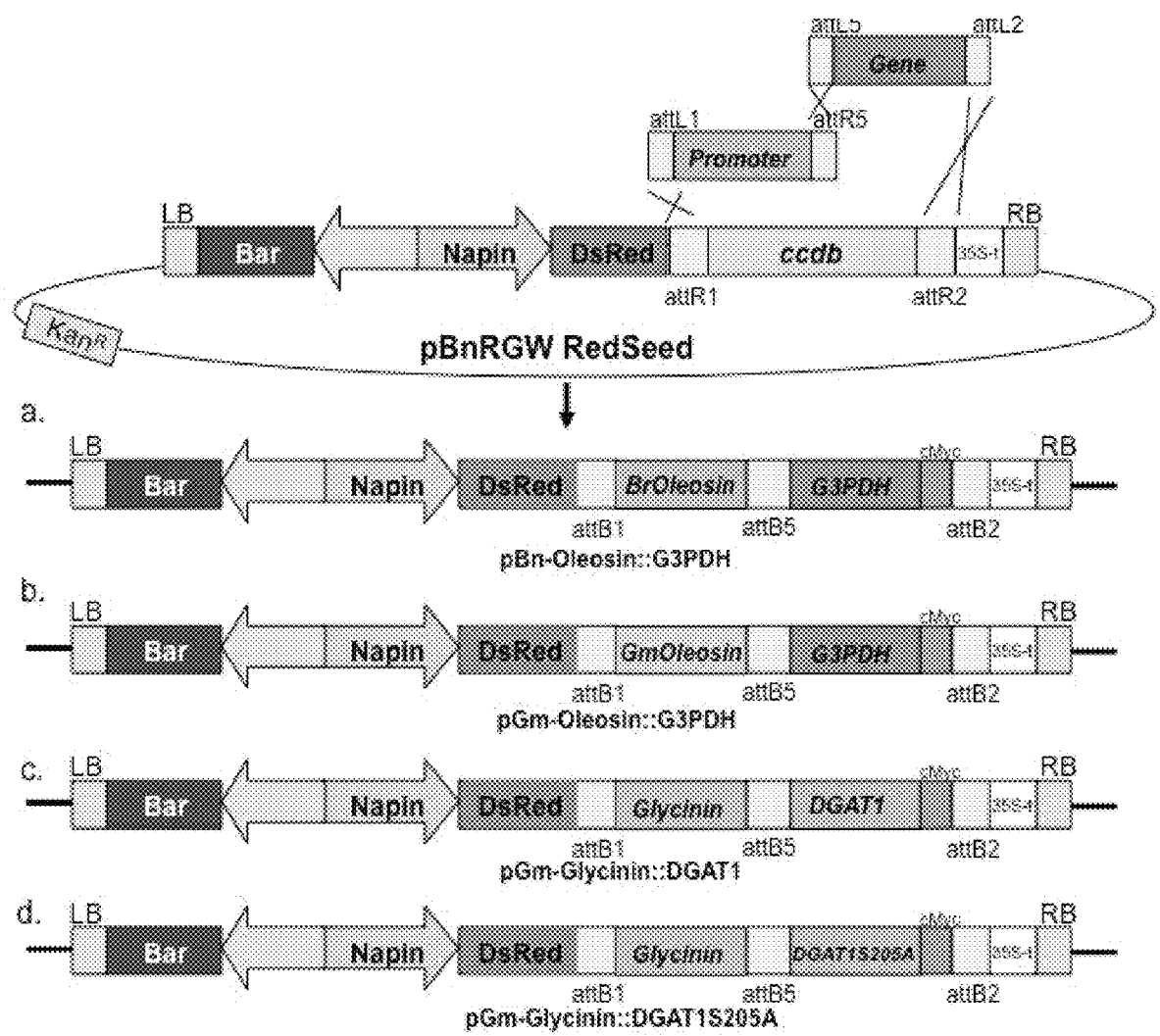
FIG. 1 presents schematic diagrams of the various binary vectors constructed from pBnRGWRedSeed containing single gene constructs encoding Br-oleosin:G3PDH (a), Gm-Oleosin:G3PDH (b), Gm-glycinin:DGAT1 (c), and Gm-glycinin:DGAT1m (d) used for nuclear transformation of Camelina. LB—Left boarder T-DNA, BAR—Basta resistance marker, DsRed—Red Fluorescence marker, attR1 and attR2 recombinase site 1 and site 2, ccdb, 35S-t 35S-terminator, RB-right border T-DNA; BrOleosin—*Brassica rapa* Oleosin promoter, Gm oleosin—*Glycine max* Glycinin promoter.

Disclosed herein are transgenic plants having increased oil content and seed yield, and methods and expression cassettes for producing such transgenic plants. The improvements in oil content and seed weight/plant are achieved by engineering the plants to have tissue-specific increases in expression of proteins which are rate limiting in the triacylglycerol (TAG) biosynthesis pathway or tissue-specific suppression of expression of certain genes affecting fatty acid (FA) availability for TAG synthesis. The tissue is preferably the seed. The disclosed methods and compositions use novel combinations of seed-specific promoter, terminator, and gene coding sequence to increase the oil content and seed weight in plants, preferably oilseed plants, for example Camelina plants. The disclosed recombinant constructs for tissue-specific alteration of expression can include a single gene coding sequence or a combination of gene coding sequences ("stacked genes").

The proteins diacylglycerol acyltransferase (DGAT1) and glycerol-3-phosphate dehydrogenase (GPD1) are each individually known to be involved in the TAG biosynthesis pathway. Enhancing expression of DGAT1 and/or GPD1 results in increased oil content and/or seed yield. The monoacylglycerol O-acyltransferase 1 (MGAT1) and phosphatidylcholine diacylglycerol cholinephosphotransferase 1 (PDCT1) genes have been identified by the inventors as genes involved in TAG biosynthesis. Engineered overexpression of MGAT1 or PDCT1 increases oil content and/or seed yield. The sugar dependent 1 (SDP1) gene is involved in fatty acid turnover. Suppression of SDP1 expression results in an increase in oil content and/or seed yield.

The disclosed transgenic plants, methods of making the plants, and transgenic expression cassettes for use in the methods are highly useful for enhancing the oil content and seed yield per acre basis in plants used for production of biofuels as well as in plants used for production of edible oils. For example, Camelina is a non-food oilseed crop which is often proposed as a dedicated crop for biofuel production. Camelina engineered as disclosed herein can grow on marginal land, and can produce enhanced levels of oil for biofuel production. Advantageously, the disclosed expression cassettes and methods for producing a transgenic plant with enhanced oil content and seed yield are applicable to a wide variety of plants, including other oil seed crops, such as those mentioned elsewhere herein, for increasing production of both biofuel as well as edible oils.

Accordingly, methods of increasing total oil content or seed yield in a plant or in a tissue, organ, part, cell, or propagation material thereof are disclosed.

In an embodiment, the method comprises expressing a first transgenic expression cassette and a second transgenic expression cassette in a plant or in a tissue, organ, part, cell, or propagation material thereof, wherein the first transgenic expression cassette comprises a nucleic acid sequence encoding a diacylglycerol acyltransferase (DGAT1) operatively linked to a plant-expressible promoter and the second transgenic expression cassette comprises a nucleic acid sequence encoding a glycerol-3-phosphate dehydrogenase (GPD1) operatively linked to a plant-expressible promoter; and selecting the plant or the tissue, organ, part, cell or propagation material thereof in which the total oil content or seed yield of the plant or the total oil content in the tissue, organ, part, cell or propagation material thereof is increased in comparison with a corresponding plant or a tissue organ part, cell or propagation material thereof that is not expressing the first transgenic expression cassette and the second transgenic expression cassette. The method can further comprise expressing a third transgenic expression cassette in the plant or in the tissue, organ, part, cell or propagation material thereof, wherein the third transgenic expression cassette comprises a nucleic acid sequence encoding a monoacylglycerol O-acyltransferase 1 (MGAT1) operably linked to a plant-expressible promoter, a nucleic acid sequence encoding a phosphatidylcholine diacylglycerol cholinephosphotransferase 1 (PDCT1) operably linked to a plant-expressible promoter, a nucleic acid sequence encoding a suppressor of expression of endogenous Sugar Dependent 1 (SDP1) operably linked to a plant-expressible promoter, or a combination thereof.

In an embodiment, the method comprises expressing a transgenic expression cassette in the plant or in the tissue, organ, part, cell or propagation material thereof, wherein the transgenic expression cassette comprises a nucleic acid sequence encoding a monoacylglycerol O-acyltransferase 1 (MGAT1) operably linked to a plant-expressible promoter, a nucleic acid sequence encoding a phosphatidylcholine diacylglycerol cholinephosphotransferase 1 (PDCT1) operably linked to a plant-expressible promoter, a nucleic acid sequence encoding a suppressor of expression of endogenous Sugar Dependent 1 (SDP1) operably linked to a plant-expressible promoter, or a combination thereof; and selecting the plant or the tissue, organ, part, cell or propagation material thereof in which the total oil content or seed yield of the plant or the total oil content in the tissue, organ, part, cell or propagation material thereof is increased in comparison with a corresponding plant or a tissue organ part, cell or propagation material thereof that is not expressing the transgenic expression cassette. The method can further comprise expressing a second transgenic expression cassette and a third transgenic expression cassette in a plant or in a tissue, organ, part, cell or propagation material thereof, wherein the second transgenic expression cassette comprises a nucleic acid sequence encoding a diacylglycerol acyltransferase (DGAT1) operatively linked to a plant-expressible promoter and the third transgenic expression cassette comprises a nucleic acid sequence encoding a glycerol-3-phosphate dehydrogenase (GPD1) operatively linked to a plant-expressible promoter.

In another aspect, methods of producing a transgenic plant having increased oil content or seed yield are also disclosed.

In an embodiment, the method comprises transforming a plant cell with a first transgenic expression cassette and a second transgenic expression cassette, wherein the first transgenic expression cassette comprises a nucleic acid sequence encoding a diacylglycerol acyltransferase (DGAT1) operatively linked to a plant-expressible promoter and the second transgenic expression cassette comprises a nucleic acid sequence encoding a glycerol-3-phosphate dehydrogenase (GPD1) operatively linked to a plant-expressible promoter; growing a plant from the transformed plant cell until the plant produces seed; and selecting a seed from a plant in which the oil content or the seed yield is higher than a plant of the same species not comprising the first and second expression cassettes. The method can further comprise transforming the plant cell with a third transgenic expression cassette. The third transgenic expression cassette can comprise a nucleic acid sequence encoding a monoacylglycerol O-acyltransferase 1 (MGAT1) operably linked to a plant-expressible promoter, a nucleic acid sequence encoding a phosphatidylcholine diacylglycerol cholinephosphotransferase 1 (PDCT1) operably linked to a plant-expressible promoter, a nucleic acid sequence encoding a suppressor of expression of endogenous Sugar Dependent 1 (SDP1) operably linked to a plant-expressible promoter, or a combination thereof.

In an embodiment, the method comprises transforming a plant cell with a first transgenic expression cassette and a second transgenic expression cassette; growing a plant from the transformed plant cell until the plant produces seed; and selecting a seed from a plant in which the oil content or the seed yield is higher than a plant of the same species not comprising the first and second expression cassettes. The first transgenic expression cassette comprises a nucleic acid sequence encoding a diacylglyerol acyltransferase (DGAT1) operatively linked to a plant-expressible promoter and the second transgenic expression cassette comprises a nucleic acid sequence encoding a glycerol-3-phosphate dehydrogenase (GPD1) operatively linked to a plant-expressible promoter. The method can further comprise transforming the plant cell with a third transgenic expression cassette. The third transgenic expression cassette can comprise a nucleic acid sequence encoding a monoacylglycerol O-acyltransferase 1 (MGAT1) operably linked to a plant-expressible promoter, a nucleic acid sequence encoding a phosphatidylcholine diacylglycerol cholinephosphotransferase 1 (PDCT1) operably linked to a plant-expressible promoter, a nucleic acid sequence encoding a suppressor of expression of endogenous Sugar Dependent 1 (SDP1) operably linked to a plant-expressible promoter, or a combination thereof.

In an embodiment, the method comprises transforming a plant cell with a transgenic expression cassette; growing a plant from the transformed plant cell until the plant produces seed; and selecting a seed from a plant in which the oil content or the seed yield is higher than a plant of the same species not comprising the transgenic expression cassette. The transgenic expression cassette can comprise a nucleic acid sequence encoding a monoacylglycerol O-acyltransferase 1 (MGAT1) operably linked to a plant-expressible promoter, a nucleic acid sequence encoding a phosphatidylcholine diacylglycerol cholinephosphotransferase 1 (PDCT1) operably linked to a plant-expressible promoter, a nucleic acid sequence encoding a suppressor of expression of endogenous Sugar Dependent 1 (SDP1) operably linked to a plant-expressible promoter, or a combination thereof. The method can further comprise transforming the plant cell with a second transgenic expression cassette and a third transgenic expression cassette. The second transgenic expression cassette comprises a nucleic acid sequence encoding a diacylglyerol acyltransferase (DGAT1) operatively linked to a plant-expressible promoter and the third transgenic expression cassette comprises a nucleic acid sequence encoding a glycerol-3-phosphate dehydrogenase (GPD1) operatively linked to a plant-expressible promoter.

In another aspect, a transgenic expression cassette is disclosed.

The transgenic expression cassette can comprise a polynucleotide encoding a diacylglyerol acyltransferase (DGAT1) operatively linked to a plant-expressible promoter; a polynucleotide encoding a glycerol-3-phosphate dehydrogenase (GPD1) operatively linked to a plant-expressible promoter; a polynucleotide encoding a monoacylglycerol O-acyltransferase 1 (MGAT1) operatively linked to a plant-expressible promoter; a polynucleotide encoding a phosphatidylcholine diacylglycerol cholinephosphotransferase 1 (PDCT1) operatively linked to a plant-expressible promoter; a polynucleotide encoding a suppressor of expression of Sugar Dependent 1 (SDP1) operatively linked to a plant-expressible promoter; or a combination thereof. The plant-expressible promoter in any of these expression cassettes can be, for example, a glycinin promoter, an oleosin promoter, a phaseolin promoter, a napin promoter, or a USP (Unknown seed protein) promoter. In certain embodiments, the glycinin promoter or the oleosin promoter can be from soybean or a Brassica organism; the phaseolin promoter can be from Phaseolus vulgaris; the napin promoter can be from a Brassica organism, such as Brassica napus; and the USP (Unknown seed protein) promoter can be from Vicia faba. Preferably the glycinin promoter comprises SEQ ID NO:6.r the oleosin promoter comprises SEQ ID NO:7 or 8, the phaseolin promoter comprises SEQ ID NO: 10,the napin promoter SEQ ID NO:11, and the USP promoter comprises SEQ ID NO:12. Any polynucleotide of the expression cassettes can be further operably linked to a transcription terminator. Preferably the transcription terminator comprises the termination sequence of the nopaline synthase (NOS) gene, isolated from Agrobacterium tumefaciens (NOS terminator), and comprises SEQ ID NOS:9.

In another aspect, a binary expression vector is disclosed. The binary expression vector can advantageously be used for recombinational cloning and expression of up to 13 genes (39 individual fragments of promoter, coding region, and terminator for 13 genes). Herein, such a vector that can be used to clone and express multiple genes simultaneously is referred to as a "gen-stacking" vector.

In an embodiment, the gene-stacking vector comprises a pCAMBIA-1300 background vector into which a fragment comprising multiple cloning sites has been cloned. An example of a fragment comprising multiple cloning sites is SEQ ID NO:17. The gene-stacking vector further comprises the red fluorescent protein DsRed under control of a Brassica Napin promoter within the T-DNA borders for screening seeds for transformants. An example of a Brassica Napin promoter fragment is SEQ ID NO:15 and an example of a DsRed fragment is SEQ ID NO:16. In certain embodiments, the gene-stacking vector comprises SEQ ID NO:19, preferably the gene-stacking vector is pSC101 having the sequence of SEQ ID NO:14 and schematically depicted in FIG. 2A.

In another aspect, a transgenic plant is disclosed. The transgenic plant has increased oil content and/or seed yield.

In an embodiment, the transgenic plant comprises a polynucleotide encoding a diacylglyerol acyltransferase (DGAT1) operatively linked to a plant-expressible promoter and a polynucleotide encoding a glycerol-3-phosphate dehydrogenase (GPD1) operatively linked to a plant-expressible promoter. The transgenic plant can further comprise a polynucleotide encoding a monoacylglycerol O-acyltransferase 1 (MGAT1) operatively linked to a plant-expressible promoter; a polynucleotide encoding a phosphatidylcholine diacylglycerol cholinephosphotransferase 1 (PDCT1) operatively linked to a plant-expressible promoter; a polynucleotide encoding a suppressor of expression of Sugar Dependent 1 (SDP1) operatively linked to a plant-expressible promoter; or a combination thereof.

In an embodiment, the transgenic plant comprises a polynucleotide encoding a monoacylglycerol O-acyltransferase 1 (MGAT1) operatively linked to a plant-expressible promoter; a polynucleotide encoding a phosphatidylcholine diacylglycerol cholinephosphotransferase 1 (PDCT1) operatively linked to a plant-expressible promoter; a polynucleotide encoding a suppressor of expression of Sugar Dependent 1 (SDP1) operatively linked to a plant-expressible promoter; or a combination thereof. The transgenic plant can further comprise a polynucleotide encoding a diacylglycerol acyltransferase (DGAT1) operatively linked to a plant-expressible promoter and a polynucleotide encoding a glycerol-3-phosphate dehydrogenase (GPD1) operatively linked to a plant-expressible promoter.

The glycerol-3-phosphate dehydrogenase (GPD1) can be from a yeast selected from a genus consisting of *Cryptococcus, Torulopsis, Pityrosporum, Brettanomyces, Candida, Kloeckera, Trigonopsis, Trichosporon, Rhodotorula, Sporobolomyces, Bullera, Saccharomyces, Debaromyces, Lipomyces, Hansenula, Endomycopsis, Pichia* and *Hanseniaspora*. The glycerol-3-phosphate dehydrogenase can be from a yeast selected from the species consisting of *Saccharomyces cerevisiae, Pichia pastoris, Hansenula polymorpha, Schizosaccharomyces pombe, Kluyveromyces lactis, Zygosaccharomyces rouxii, Yarrowia lipolitica, Emericella nidulans, Aspergillus nidulans, Debaryomyces hansenii* and *Torulaspora hansenii*.

The diacylglyerol acyltransferase (DGAT1) can be from an organism of a genus selected from *Arabidopsis, Tropaeolum, Brassicca, Glycine, Linum, Helianthus, Camelina, Arachis, Ricinus, Cuphea, Crambe, Avocado (Persea americana),* and *Gossipium*.

The MGAT1, PDCT1, or SDP1 can be from a yeast or an organism of a genus selected from *Arabidopsis, Tropaeolum, Brassicca, Glycine, Linum, Helianthus, Camelina, Arachis, Ricinus, Cuphea, Crambe, Avacado,* and *Gossipium*.

In the disclosed methods and compositions, the sequence of DGAT1 can comprise SEQ ID NO:1; the sequence of GPD1 can comprise SEQ ID NO:2; the sequence of MGAT1 can comprise SEQ ID NO:3; the sequence of PDCT1 can comprise SEQ ID NO:4; or the sequence of SDP1 can comprise SEQ ID NO:5.

Reduced expression of SDP1 activity in a tissue can be achieved by suppressing expression of endogenous SDP1 activity by transforming the plant with a polynucleotide encoding a suppressor of an endogenous SDP1 operably linked to a promoter specific for the tissue and/or by genome editing or mutation of the endogenous SDP1 gene such that the modified endogenous SDP1 gene has reduced expression of SDP1 activity compared to the unmodified endogenous SDP1 gene. The suppressor introduced into the plant can be an RNA interference (RNAi) nucleic acid or an antisense RNA.

Increased expression of protein, for example DGAT1, GPD1, MGAT1, or PDCT1, in the transgenic plant can be achieved by genome editing or mutation of the endogenous gene such that the edited or mutated endogenous gene has increased expression of the protein's activity compared to the unmodified endogenous gene, by increasing copy number of the endogenous gene, or by introducing a polynucleotide encoding at least one copy of a heterologous gene operably linked to a promoter expressible in the plant.

Herein, "oil content" of a plant refers to the total weight of the oil produced by the plant. The "oil content" of a seed refers to the total weight of the oil produced by an individual seed, and can be expressed as the weight oil per single seed or 100 seeds, or alternatively as weight of the oil per unit weight of seed.

An increase in oil content of a transgenic plant made using the methods and constructs disclosed herein can be at least about, e.g. 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 55%, 60%, 65%, 70%, 75%, 80%, 85%, 90%, 95%, 100%, 105%, 110%, 120%, 125%, 130%, 135%, 140%, 145%, 150%, 155%, 160%, 165%, 170%, 175%, 180%, 185%, 190%, 195%, 200%, 205%, 210%, 215%, 220%, 225%, 230%, 235%, 240%, 245%, 250%, 255%, 260%, 265%, 270%, 275%, 280%, 285%, 290%, 296%, 300%, 310%, 320%, 330%, 340%, 350%, 375%, 400%, 450%, 500% or more, higher than the oil content of a control plant, i.e., a plant of the same species as the transgenic plant but that does not comprise the transgenic expression construct(s) disclosed herein. In particular embodiments, an increase in increase in oil content of a transgenic plant disclosed herein can be an increase of at least about, e.g., 2% to about 60%, 5% to about 55%, about 5% to about 50%, about 5% to about 60%, about 10% to about 50%, about 10% to about 55%, about 10% to about 60%, about 15% to about 45%, about 15% to about 50%, about 15% to about 55%, about 15% to about 60%, about 20% to about 40%, about 20% to about 45%, about 20% to about 50%, about 20% to about 55%, about 20% to about 60%, and the like compared to the oil content of a control plant.

An increase in oil content of a seed of a transgenic plant made using the methods and constructs disclosed herein can similarly be at least about, e.g. 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 55%, 60%, 65%, 70%, 75%, 80%, 85%, 90%, 95%, 100%, 105%, 110%, 120%, 125%, 130%, 135%, 140%, 145%, 150%, 155%, 160%, 165%, 170%, 175%, 180%, 185%, 190%, 195%, 200%, 205%, 210%, 215%, 220%, 225%, 230%, 235%, 240%, 245%, 250%, 255%, 260%, 265%, 270%, 275%, 280%, 285%, 290%, 296%, 300%, 310%, 320%, 330%, 340%, 350%, 375%, 400%, 450%, 500% or more, higher than the oil content of a seed of a control plant, i.e., a plant of the same species as the transgenic plant but that does not comprise the transgenic expression construct(s) disclosed herein. In particular embodiments, an increase in increase in oil content of seeds and fruits (or other plant parts) of a transgenic plant disclosed herein can be an increase of at least about, e.g., 2% to about 60%, 5% to about 55%, about 5% to about 50%, about 5% to about 60%, about 10% to about 50%, about 10% to about 55%, about 10% to about 60%, about 15% to about 45%, about 15% to about 50%, about 15% to about 55%, about 15% to about 60%, about 20% to about 40%, about 20% to about 45%, about 20% to about 50%, about 20% to about 55%, about 20% to about 60%, and the like compared to the oil content of seeds of a control plant.

Herein, "seed yield" refers to total weight of the seed produced by a plant. An increase in seed yield produced by a transgenic plant disclosed herein can be at least about, e.g., 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 55%, 60%, 65%, 70%, 75%, 80%, 85%, 90%, 95%, 100%, 105%, 110%, 120%, 125%, 130%, 135%, 140%, 145%, 150%, 155%, 160%, 165%, 170%, 175%, 180%, 185%, 190%, 195%, 200%, 205%, 210%, 215%, 220%, 225%, 230%, 235%, 240%, 245%, 250%, 255%, 260%, 265%, 270%, 275%, 280%, 285%, 290%, 296%, 300%, 310%, 320%, 330%, 340%, 350%, 375%, 400%, 450%, 500% or more, or any range therein, as compared to a control plant, i.e., a plant of the same species not comprising the transgenic expression cassette(s) present in the transgenic plant. In other embodiments, an increase in seed yield can be an increase of about 20% to about 200%, about 20% to about 250%, about 20% to about 300%, about 20% to about 350%, about 30% to about 200%, about 30% to about 250%, about 30% to about 300%, about 30% to about 350%, about 40% to about 200%, about 40% to about 250%, about 40% to about 300%, about 40% to about 350%, about 50% to about 200%, about 50% to about 250%, about 50% to about 300%, about 50% to about 350%, about 75% to about 200%, about 75% to about 250%, about 75% to about 300%, about 75% to about 350%, about 100% to about 200%, about 100% to about 250%, about 100% to about 300%, about 100% to about 350%, and the like, as compared to a control plant. In some particular embodiments, the increase in seed yield can be about 120% to about 320%, about 150% to about 200%, about 150% to about 250%, about 150% to about 300%, about 150% to about 350%, and the like, as compared to a control plant.

Herein, "plant" refers to all genera and species of higher and lower plants of the Plant Kingdom. The term includes the mature plants, seeds, shoots and seedlings, and parts, propagation material, plant organ tissue, protoplasts, callus and other cultures, for example cell cultures, derived from them, and all other species of groups of plant cells giving functional or structural units. Mature plants refers to plants at any developmental stage beyond the seedling. Seedling refers to a young, immature-plant at an early developmental stage.

The term "plant part," as used herein, includes but is not limited to reproductive tissues (e.g., petals, sepals, stamens, pistils, receptacles, anthers, pollen, flowers, fruits, flower bud, ovules, seeds, embryos, nuts, kernels, ears, cobs and husks); vegetative tissues (e.g., petioles, stems, roots, root hairs, root tips, pith, coleoptiles, stalks, shoots, branches, bark, apical meristem, axillary bud, cotyledon, hypocotyls, and leaves); vascular tissues (e.g., phloem and xylem); specialized cells such as epidermal cells, parenchyma cells, chollenchyma cells, schlerenchyma cells, stomates, guard cells, cuticle, mesophyll cells; callus tissue; and cuttings. The term "plant part" also includes plant cells, including plant cells that are intact in plants and/or parts of plants, plant protoplasts, plant tissues, plant organs, plant cell tissue cultures, plant calli, plant clumps, and the like. As used herein, "shoot" refers to the above ground parts including the leaves and stems. As used herein, the term "tissue culture" encompasses cultures of tissue, cells, protoplasts and callus.

As used herein, "plant cell" refers to a structural and physiological unit of the plant, which typically comprise a cell wall but also includes protoplasts. A plant cell of the present invention can be in the form of an isolated single cell or can be a cultured cell or can be a part of a higher-organized unit such as, for example, a plant tissue (including callus) or a plant organ. In some embodiments, a plant cell can be an algal cell.

"Plant" encompasses all annual and perennial monocotyldedonous or dicotyledonous plants and includes by way of example, but not by limitation, those of the genera *Cucurbita*, *Rosa*, *Vitis*, *Juglans*, *Fragaria*, *Lotus*, *Medicago*, *Onobrychis*, *Trifolium*, *Trigonella*, *Vigna*, *Citrus*, *Linum*, *Geranium*, *Manihot*, *Daucus*, *Arabidopsis*, *Brassica*, *Raphanus*, *Sinapis*, *Atropa*, *Capsicum*, *Datura*, *Hyoscyamus*, *Lycopersicon*, *Nicotiana*, *Solarium*, *Petunia*, *Digitalis*, *Majorana*, *Cichorium*, *Helianthus*, *Lactuca*, *Bromus*, *Asparagus*, *Antirrhinum*, *Heterocallis*, *Nemesis*, *Pelargonium*, *Panieum*, *Pennisetum*, *Ranunculus*, *Senecio*, *Salpiglossis*, *Cucumis*, *Browaalia*, *Glycine*, *Pisum*, *Phaseolus*, *Lolium*, *Oryza*, *Zea*, *Avena*, *Hordeum*, *Secale*, *Triticum*, *Sorghum*, *Picea* and *Populus*.

Preferred plants are those from the following plant families: Amaranthaceae, Asteraceae, Brassicaceae, Carophyllaceae, Chenopodiaceae, Compositae, Cruciferae, Cucurbitaceae, Labiatae, Leguminosae, Papilionoideae, Liliaceae, Linaceae, Malvaceae, Rosaceae, Rubiaceae, Saxifragaceae, Scrophulariaceae, Solanaceae, Sterculiaceae, Tetragoniaceae, Theaceae, Umbelliferae.

The invention can particularly be applied advantageously to dicotyledonous plant organisms. Preferred dicotyledonous plants are selected in particular from the dicotyledonous crop plants such as, for example, Asteraceae such as sunflower, tagetes or calendula and others; Compositae, especially the genus *Lactuca*, very particularly the species *sativa* (lettuce) and others; Cruciferae, particularly the genus *Brassica*, very particularly the specis *napus* (oilseed rape), *campestris* (beet), *oleracea* cv Tastie (cabbage), *oleracea* cv Snowball Y (cauliflower) and *oleracea* cv Emperor (broccoli) and other cabbages; and the genus *Arabidopsis*, very particularly the species *thaliana*, and cress or canola and others; Cucurbitaceae such as melon, pumpkin/squash or zucchini and others; Leguminosae, particularly the genus *Glycine*, very particularly the species max (soybean), soya, and alfalfa, pea, beans or peanut and others; Rubiaceae, preferably the subclass Lamiidae such as, for example *Coffea arabica* or *Coffea liberica* (coffee bush) and others; Solanaceae, particularly the genus *Lycopersicon*, very particularly the species *esculentum* (tomato), the genus *Solanum*, very particularly the species *tuberosum* (potato) and *melongena* (aubergine) and the genus *Capsicum*, very particularly the genus *annuum* (pepper) and tobacco or paprika and others; Sterculiaceae, preferably the subclass Dilleniidae such as, for example, *Theobroma cacao* (cacao bush) and others; Theaceae, preferably the subclass Dilleniidae such as, for example, *Camellia sinensis* or *Thea sinensis* (tea shrub) and others; Umbelliferae, particularly the genus *Daucus* (very particularly the species *carota* (carrot)) and *Apium* (very particularly the species *graveolens* dulce (celery)) and others; and linseed, cotton, hemp, flax, cucumber, spinach, carrot, sugar beet and the various tree, nut and grapevine species, in particular banana and kiwi fruit.

Of particular interest for transformation are plants which are oil crop plants, also referred to as "oilseed plants" herein. Oil crop plants are understood as being plants whose oil content is already naturally high and/or which can be used for the industrial production of oils. These plants can have a high oil content and/or else a particular fatty acid composition which is of interest industrially. Preferred plants are those with a lipid content of at least 1% by weight. Oil crops encompass by way of example: *Borago officinalis* (borage); Camelina (false flax); *Brassica* species such as *B. campestris*, *B. napus*, *B. rapa*, *B. carinata* (mustard, oilseed rape or turnip rape); *Cannabis sativa* (hemp); *Carthamus tinctorius* (safflower); *Cocos nucifera* (coconut); *Crambe abyssinica* (crambe); *Cuphea* species (*Cuphea* species yield fatty acids of medium chain length, in particular for industrial applications); *Elaeis guinensis* (African oil palm); *Elaeis oleifera* (American oil palm); *Glycine max* (soybean); *Gossypium hirsutum* (American cotton); *Gossypium barbadense* (Egyptian cotton); *Gossypium herbaceum* (Asian cotton); *Arachis hypogea* (groundnut); *Helianthus annuus* (sunflower); *Linum usitatissimum* (linseed or flax); *Oenothera biennis* (evening primrose); *Olea europaea* (olive); *Oryza sativa* (rice); *Ricinus communis* (castor); *Sesamum indicum* (sesame); *Triticum* species (wheat); *Zea mays* (maize), and various nut species such as, for example, walnut or almond.

Camelina species, commonly known as false flax, are native to Mediterranean regions of Europe and Asia and seem to be particularly adapted to cold semiarid climate zones (steppes and prairies). The species *Camelina sativa* was historically cultivated as an oilseed crop to produce vegetable oil and animal feed. It has been introduced to the high plain regions of Canada and parts of the United States as an industrial oilseed crop. As a result of its high oil content (~35%) of its seeds, its frost tolerance, short production cycle (85-100 days), and insect resistance, it is an interesting target for enhancing photosynthesis and increasing assimilate partitioning to improve its potential as a source for production of biofuels.

The terms "polypeptide," "peptide" and "protein" are used interchangeably herein to refer to a molecule formed from the linking, in a defined order, of at least two amino acids. The link between one amino acid residue and the next is an amide bond and is sometimes referred to as a peptide bond. A polypeptide can be obtained by a suitable method known in the art, including isolation from natural sources, expression in a recombinant expression system, chemical synthesis, or enzymatic synthesis.

The term "nucleic acid", "polynucleotide", or "oligonucleotide" includes DNA molecules and RNA molecules. A polynucleotide may be single-stranded or double-stranded. A polynucleotide can be obtained by a suitable method known in the art, including isolation from natural sources, chemical synthesis, or enzymatic synthesis. Nucleotides may be referred to by their commonly accepted single-letter codes.

As used herein, the term "gene" refers to a nucleic acid molecule capable of being used to produce mRNA, antisense RNA, miRNA, and the like. Genes may or may not be capable of being used to produce a functional protein. Genes can include both coding and non-coding regions (e.g., introns, regulatory elements, promoters, enhancers, termination sequences and 5' and 3' untranslated regions). In some embodiments, gene refers to a coding sequence operably linked to a promoter.

"Homolog" is a term used in the art to indicate a polynucleotide or polypeptide sequence possessing a high degree of sequence relatedness to a subject sequence. Such relatedness may be quantified by determining the degree of identity and/or similarity between the sequences being compared. Falling within this generic term are the terms "ortholog" meaning a polynucleotide or polypeptide that is the functional equivalent of a polynucleotide or polypeptide in another species, and "paralog" meaning a functionally similar sequence when considered within the same species. Paralogs present in the same species or orthologs of a gene in other species can readily be identified without undue experimentation, by molecular biological techniques well known in the art. As used herein, DGAT1, GPD1, MGAT1, PDCT1, or SDP1 refers to DGAT1, GPD1, MGAT1, PDCT1, or SDP1, respectively, as well as its homologs and orthologs.

Related polypeptides to a reference polypeptide (for example, DGAT1, GPD1, MGAT1, PDCT1, or SDP1) are aligned with the reference polypeptide by assigning degrees of homology to various deletions, substitutions and other modifications. Homology can be determined along the entire polypeptide or polynucleotide, or along subsets of contiguous residues. The percent identity is the percentage of amino acids or nucleotides that are identical when the two sequences are compared. The percent similarity is the percentage of amino acids or nucleotides that are chemically similar when the two sequences are compared. A reference polypeptide (e.g., DGAT1, GPD1, MGAT1, PDCT1, or SDP1) and homologous polypeptides of the reference polypeptide are preferably greater than or equal to about 75%, preferably greater than or equal to about 80%, more preferably greater than or equal to about 90% or most preferably greater than or equal to about 95% identical.

As used herein, "percent homology" of two amino acid sequences or of two nucleic acid sequences is determined using the algorithm of Karlin and Altschul (1990) Proc. Natl. Acad. Sci., U.S.A. 87: 2264-2268. Such an algorithm is incorporated into the NBLAST and XBLAST programs of Altschul et al. (1990) J. Mol. Biol. 215: 403-410. BLAST nucleotide searches are performed with the NBLAST program, score=100, word length 12, to obtain nucleotide sequences homologous to a nucleic acid molecule of the invention. BLAST protein searches are performed with the XBLAST program, score=50, word length=3, to obtain amino acid sequences homologous to a reference polypeptide. To obtain gapped alignments for comparison purposes, Gapped BLAST is utilized as described in Altschul et al. (1997) Nucleic Acids Res. 25: 3389-3402. When utilizing BLAST and Gapped BLAST programs, the default parameters are typically used. (See the BLAST web-based tools or downloadable software available from the U.S. National Center for Biotechnology Information.)

In addition, polynucleotides that are substantially identical to a polynucleotide encoding a DGAT1, GPD1, MGAT1, PDCT1, or SDP1 polypeptide are included. By "substantially identical" is meant a polypeptide or polynucleotide having a sequence that is at least about 85%, specifically about 90%, and more specifically about 95% or more identical to the sequence of the reference amino acid or nucleic acid sequence. For polypeptides, the length of the reference polypeptide sequence will generally be at least about 16 amino acids, or specifically at least about 20 amino acids, more specifically at least about 25 amino acids, and most specifically at least about 35 amino acids. For nucleic acids, the length of the reference nucleic acid sequence will generally be at least about 50 nucleotides, specifically at least about 60 nucleotides, more specifically at least about 75 nucleotides, and most specifically at least about 110 nucleotides.

Reference herein to either the nucleotide or amino acid sequence of DGAT1, GPD1, MGAT1, PDCT1, or SDP1, respectively, also includes reference to naturally occurring variants of these sequences. Non-naturally occurring variants that differ from the nucleotide or amino acid sequence of DGAT1, GPD1, MGAT1, PDCT1, or SDP1, respectively and retain biological function are also included herein. For example, non-naturally occurring polypeptide variants that differ from the polypeptide encoded by any one of SEQ ID NOs:1-5 and retain biological function are also included herein. Preferably the variants comprise those polypeptides having conservative amino acid changes, i.e., changes of similarly charged or uncharged amino acids. Genetically encoded amino acids are generally divided into four families: (1) acidic (aspartate, glutamate); (2) basic (lysine, arginine, histidine); (3) non-polar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. As each member of a family has similar physical and chemical properties as the other members of the same family, it is reasonable to expect that an isolated replacement of a leucine with an isoleucine or valine, an aspartate with a glutamate, a threonine with a serine, or a similar replacement of an amino acid with a structurally related amino acid will not have a major effect on the binding properties of the resulting molecule. Variants of polypeptidescan be made by methods known in the art, for example, site-directed mutagenesis of polynucleotides, by random mutation, by chemical synthesis, or by chemical or enzymatic cleavage of the polypeptides. Whether an amino acid change results in a functional polypeptide can be determined by assaying the properties of transgenic plants containing the variant of DGAT1, GPD1, MGAT1, PDCT1, or SDP1.

In one embodiment, the DGAT1, GPD1, MGAT1, or PDCT1 gene or a suppressor of SDP1 gene is expressed in an expression vector suitable for in vivo expression such as, for example, plant expression systems. The expression cassette for the DGAT1, GPD1, MGAT1, or PDCT1 gene or a suppressor of SDP1 gene is inserted into a recombinant expression vector or vectors.

The term "expression vector" or "vector" refers to a plasmid, virus, or other means known in the art that has been manipulated by insertion or incorporation of a genetic sequence of interest. The term "plasmids" generally is designated herein by a lower case p preceded and/or followed by capital letters and/or numbers, in accordance with standard naming conventions that are familiar to those of skill in the art. Plasmids disclosed herein are either commercially available, publicly available on an unrestricted basis, or can be constructed from available plasmids by routine application of well-known, published procedures. Many plasmids and other cloning and expression vectors are well known and readily available, or those of ordinary skill in the art may readily construct any number of other plasmids suitable for use. These vectors are transformed into a suitable host cell to form a host cell vector system for the production of a polypeptide.

As used herein, "expression cassette" or "transgenic expression cassette" means a recombinant nucleic acid molecule comprising at least one coding sequence of interest operably linked with at least a control sequence (e.g., a promoter). The term "recombinant polynucleotide" refers to a polynucleotide that is made by the combination of two otherwise separated segments of sequence accomplished by the artificial manipulation of isolated segments of polynucleotides by genetic engineering techniques or by chemical synthesis. The coding sequence of interest can be, e.g., a polynucleotide encoding a diacylglycerol acyltransferase (DGAT1), a glycerol-3-phosphate dehydrogenase (GPD1), a monoacylglycerol O-acyltransferase 1 (MGAT1), a phosphatidylcholine diacylglycerol cholinephosphotransferase 1 (PDCT1), and/or a suppressor of expression of a sugar dependent 1 (SDP1) gene. Thus, transgenic expression cassettes designed to express a polynucleotide encoding a diacylglycerol acyltransferase, a polynucleotide encoding a glycerol-3-phosphate dehydrogenase, a polynucleotide encoding a monoacylglycerol O-acyltransferase 1, a polynucleotide encoding a phosphatidylcholine diacylglycerol cholinephosphotransferase 1, and/or a polynucleotide encoding a suppressor of expression of a sugar dependent 1 (SDP1) gene are disclosed herein.

An expression cassette comprising a recombinant nucleic acid molecule may be chimeric, meaning that at least one of its components is heterologous with respect to at least one of its other components. In some embodiments, the expression cassettes comprising the heterologous polynucleotides can comprise one or more regulatory elements in addition to a promoter as described herein (e.g., enhancers, introns, translation leader sequences, translation termination sequences, and polyadenylation signal sequences). However, a transgenic expression cassette is also understood as meaning those constructs where a nucleic acid sequence encoding a nonendogenous polypeptide is placed behind an endogenous plant promoter in such a way that the latter brings about the expression of the nonendogenous polypeptide.

Operable linkage and a transgenic expression cassette can both be effected by means of conventional recombination and cloning techniques as they are described, for example, in Maniatis T, Fritsch E F and Sambrook J (1989) Molecular Cloning: A Laboratory Manual, Cold Spring Harbor Laboratory, Cold Spring Harbor (N.Y.), in Silhavy T J, Berman M L and Enquist L W (1984) Experiments with Gene Fusions, Cold Spring Harbor Laboratory, Cold Spring Harbor (N.Y.), in Ausubel F M et al. (1987) Current Protocols in Molecular Biology, Greene Publishing Assoc. and Wiley Interscience and in Gelvin et al. (1990) In: Plant Molecular Biology Manual. However, further sequences which, for example, act as a linker with specific cleavage sites for restriction enzymes, or of a signal peptide, may also be positioned between the two sequences. Also, the insertion of sequences may lead to the expression of fusion proteins. Preferably, the expression cassette composed of a promoter linked to a nucleic acid sequence to be expressed can be in a vector-integrated form and can be inserted into a plant genome, for example by transformation.

Furthermore, such polynucleotides can be stacked with any combination of nucleotide sequences to create plants, plant parts, and/or plant cells having the desired phenotype. Stacked combinations can be created by any method including, but not limited to, any conventional methodology (e.g., cross breeding for plants), or by genetic transformation. If stacked by genetic transformation, nucleotide sequences encoding additional desired traits can be combined at any time and in any order. For example, a transgenic plant comprising one or more desired traits can be used as the target to introduce further traits by subsequent transformation. The additional nucleotide sequences can be introduced simultaneously in a co-transformation protocol with a nucleotide sequence, nucleic acid molecule, nucleic acid construct, and/or other composition of the invention, provided by any combination of expression cassettes. For example, if two nucleotide sequences will be introduced, they can be incorporated in separate cassettes (trans) or can be incorporated on the same cassette (cis). Expression of the nucleotide sequences can be driven by a single promoter or by separate promoters, which can be the same or different, or a combination thereof. It is further recognized that nucleotide sequences can be stacked at a desired genomic location using a site-specific recombination system. See, e.g., Int'l Patent Application Publication Nos. WO 99/25821; WO 99/25854; WO 99/25840; WO 99/25855 and WO 99/25853.

The term "transgene" refers to a recombinant polynucleotide or nucleic acid that comprises a coding sequence encoding a protein or RNA molecule.

The transgenic expression cassettes are inserted into a vector adapted for expression in a plant, bacterial, yeast, insect, amphibian, or mammalian cell that further comprises the regulatory elements necessary for expression of the nucleic acid molecule in the plant, bacterial, yeast, insect, amphibian, or mammalian cell operatively linked to the nucleic acid molecule encoding a sequence of interest for expression.

"Operatively linked" or "operably linked" refers to a juxtaposition wherein the components so described are in a relationship permitting them to function in their intended manner. An expression control sequence operatively linked to a coding sequence is ligated such that expression of the coding sequence is achieved under conditions compatible with the expression control sequences. For instance, a promoter is operatively linked with a nucleotide sequence if the promoter effects the transcription or expression of the nucleotide sequence. Those skilled in the art will appreciate that the control sequences (e.g., promoter) need not be contiguous with the nucleotide sequence to which it is operably linked, as long as the control sequences function to direct the expression thereof. Thus, for example, intervening untranslated, yet transcribed, sequences can be present between a promoter and a nucleotide sequence, and the promoter can still be considered "operatively linked" to the nucleotide sequence. Expression control sequences such as, for example, enhancer sequences can also exert their function on the target sequence from positions which are further removed or indeed from other DNA molecules.

As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signals for introns (if introns are present), translation leader sequences, translation termination sequences, polyadenylation signal sequences, and stop codons. The term "control sequences" is intended to include, at a minimum, components whose presence can influence expression, and can also include additional components whose presence is advantageous, for example, leader sequences and fusion partner sequences. Expression control sequences can include a promoter. By "promoter" is meant minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included. If a promoter is inducible, there are sequences present that mediate regulation of expression so that the associated sequence is transcribed only when an inducer (e.g., light or an exogenous chemical regulator) is available to the plant or plant tissue. An exemplary promoter to provide basal expression and avoid overexpression in transgenic plants is the 35S cauliflower mosaic virus (CaMV) promoter.

Any promoter useful for initiation of transcription in a cell of a plant can be used in the expression cassettes of the present invention. Promoters can include, for example, constitutive, inducible, temporally regulated, developmentally regulated, chemically regulated, and/or tissue-specific promoters for use in the preparation of recombinant nucleic acid molecules, for example transgenic expression cassettes or recombinant polynucleotides. These various types of promoters are known in the art. Promoters can be identified in and isolated from the plant to be transformed and then inserted into the expression cassette to be used in transformation of the plant. Alternatively, nonendogenous promoters isolated from other plants, but functional in the plant to be transformed, can be inserted into the expression cassettes.

Promoters which are preferably introduced into the transgenic expression cassettes are those which are operable in a plant or a tissue, organ, part, cell or propagation material of the plant. A promoter which is operable in plants is understood as meaning any promoter which is capable of governing the expression of genes, in particular nonendogenous genes, in plants or plant parts, plant cells, plant tissues or plant cultures.

A "constitutive" promoter refers to a-promoter which ensures expression in a large number of, preferably all, tissues over a substantial period of plant development, preferably at all times during plant development (Benfey et al. (1989) EMBO J 8:2195-2202). A plant promoter or promoter originating from a plant virus is preferably used. The promoter of the CaMV (cauliflower mosaic virus) 35S transcript (Franck et al. (1980) Cell 21:285-294; Odell et al. (1985) Nature 313:810-812; Shewmaker et al. (1985) Virology 140:281-288; Gardner et al. (1986) Plant Mol Biol 6:221-228) or the 19S CaMV promoter (U.S. Pat. No. 5,352,605; WO 84/02913; Benfey et al. (1989) EMBO J 8:2195-2202) are preferred. Another suitable constitutive promoter is the Rubisco small subunit (SSU) promoter (U.S. Pat. No. 4,962,028), the leguminB promoter (GenBank Acc. No. X03677), the promoter of the nopalin synthase from Agrobacterium, the TR dual promoter, the OCS (octopine synthase) promoter from Agrobacterium, the ubiquitin promoter (Holtorf S et al. (1995) Plant Mol Biol 29:637-649), the ubiquitin 1 promoter (Christensen et al. (1992) Plant Mol Biol 18:675-689; Bruce et al. (1989) Proc Natl Acad Sci USA 86:9692-9696), the Smas promoter, the cinnamyl alcohol dehydrogenase promoter (U.S. Pat. No. 5,683,439), the promoters of the vacuolar ATPase subunits, and the promoter of the *Arabidopsis thaliana* nitrilase-1 gene (GenBank Acc. No.: U38846, nucleotides 3862 to 5325 or else 5342), and further promoters of genes whose constitutive expression in plants is known to the skilled worker. Additional examples include cestrum virus promoter (cmp) (U.S. Pat. No. 7,166,770), nos promoter (Ebert et al. (1987) Proc. Natl. Acad. Sci USA 84:5745-5749), Adh promoter (Walker et al. (1987) Proc. Natl. Acad, Sci. USA 84:6624-6629), sucrose synthase promoter (Yang & Russell (1990) Proc. Natl. Acad. Sci. USA 87:4144-4148), and the ubiquitin promoter. The constitutive promoter derived from ubiquitin accumulates in many cell types. Ubiquitin promoters have been cloned from several plant species for use in transgenic plants, for example, sunflower (Binet et al., 1991. Plant Science 79: 87-94) and arabidopsis (Norris et al. 1993. Plant Molec. Biol. 21:895-906).

A "tissue-specific promoter" refers to a-promoter which ensures expression in a specific tissue over a substantial period of plant development. A preferred tissue for localization of expression is a seed. Examples of seed-specific promoters include the phaseolin promoter (U.S. Pat. No. 5,504,200; Bustos M M et al. (1989) Plant Cell 1.(9):839-53), the promoter of the 2S albumin gene (Joseffson L G et al. (1987) J Biol Chem 262:12196-12201), the legumine promoter (Shirsat A et al. (1989) Mol Gen Genet 215(2):326-331), the USP (unknown seed protein) promoter (Bäumlein H et al. (1991) Mol Gen Genet 225(3):459-67), the napin gene promoter (U.S. Pat. No. 5,608,152; Stalberg K et al. (1996) L Planta 199:515-519), the promoter of the sucrose binding proteins (WO 00/26388) or the legumin B4 promoter (LeB4; Bäumlein H et al. (1991) Mol Gen Genet 225: 121-128; Bäumlein et al. (1992) Plant Journal 2(2): 233-9; Fiedler U et al. (1995) Biotechnology (NY) 13(10): 1090f), the *Arabidopsis* oleosin promoter (WO 98/45461), and the *Brassica* Bce4 promoter (Wo 91/13980). Further suitable seed-specific promoters are those of the gene encoding high-molecular weight glutenin (HMWG), gliadin, branching enyzme, ADP glucose pyrophosphatase (AGPase), starch synthase, or glycinin. Yet other examples include promoters associated with genes encoding the seed storage proteins (such as β-conglycinin, cruciferin, napin and phaseolin), zein or oil body proteins (such as oleosin), or proteins involved in fatty acid biosynthesis (including acyl carrier protein, stearoyl-ACP desaturase and fatty acid desaturases (fad 2-1). Also useful for seed-specific expression is the pea vicilin promoter (Czako et al. (1992) Mol. Gen. Genet. 235:33-40; as well as the seed-specific promoters disclosed in U.S. Pat. No. 5,625,136.

The expression cassettes may also contain a "chemically-inducible promoter" (review article: Gatz et al. (1997) Annu Rev Plant Physiol Plant Mol Biol 48:89-108), by means of which the expression of an exogenous gene in the plant can be controlled at a particular point in time. Such promoters include, for example, the PRP1 promoter (Ward et al. (1993) Plant Mol Biol 22:361-366), a salicylic acid-inducible promoter (WO 95/19443), a benzenesulfonamide-inducible promoter (EP 0 388 186), a tetracyclin-inducible promoter (Gatz et al. (1992) Plant J 2:397-404), an abscisic acid-inducible promoter EP 0 335 528), and an ethanol-cyclohexanone-inducible promoter (WO 93/21334). Also suitable is the promoter of the glutathione-S transferase isoform II gene (GST-II-27), which can be activated by exogenously applied safeners such as, for example, N,N-diallyl-2,2-dichloroacetamide (WO 93/01294) and which is operable in a large number of tissues of both monocots and dicots.

Particularly preferred are seed-specific promoters, in particular the glycinin promoter and the oleosin promoter.

In addition, further promoters which make possible expression in further plant tissues or in other organisms such as, for example, *E. coli* or yeast, may be linked operably with the nucleic acid sequence-to be expressed.

"Plant-expressible transcriptional and translational regulatory sequences" are those that can function in plants, plant tissue and/or plant cells to effect the transcriptional and translational expression of the nucleotide sequences with that they are associated. Included are 5' sequences that qualitatively control gene expression (turn on or off gene expression in response to environmental signals such as light, or in a tissue-specific manner) and quantitative regulatory sequences that advantageously increase the level of downstream gene expression. An example of a sequence motif that serves as a translational control sequence is that of the ribosome binding site sequence. Polyadenylation signals are examples of transcription regulatory sequences positioned downstream of a target sequence. Exemplary flanking sequences include the 3' flanking sequences of the nos gene of the *Agrobacterium tumefaciens* Ti plasmid. The upstream nontranslated sequence of a bacterial merA coding sequence can be utilized to improve expression of other sequences in plants as well.

The plant-expressible transcription regulatory sequence optionally comprises an inducible promoter to drive gene expression in response to selected stimuli. Suitable inducible promoters include a light inducible promoter such as the SRS1 promoter, and the chlorophyll A/13 binding protein light-inducible transcription regulator sequences.

Chemical-regulated promoters can be used to modulate the expression of a gene in an organism through the application of an exogenous chemical regulator. Regulation of the expression of nucleotide sequences of the invention via promoters that are chemically regulated enables the polypeptides of the invention to be synthesized only when, for example, a crop of plants are treated with the inducing chemicals. Depending upon the objective, the promoter may be a chemical-inducible promoter, where application of a chemical induces gene expression, or a chemical-repressible promoter, where application of the chemical represses gene expression An expression cassette, or recombinant polynucleotide, encoding a suppressor of SDP1 expression operably linked to a promoter and/or encoding a DGAT1, GPD1, MGAT1, and/or PDCT1 polypeptide operably linked to a promoter can be introduced (in any order) into a plant in any combination with one or more additional polynucleotides to increase the number or weight of seeds and/or increase the total oil content in a plant.

The expression cassettes disclosed herein can be on a single expression vector or cassette or on multiple expression vectors or cassettes, and can be introduced into plants singly or introduced more than one at a time using co-transformation methods as known in the art.

In some embodiments of the invention, an expression vector or cassette can comprise an enhancer sequence. Enhancer sequences can be derived from, for example, any intron from any highly expressed gene. In particular embodiments, an enhancer sequence usable in an expression vector or cassette disclosed herein includes, but is not limited to, the nucleotide sequence of ggagg (e.g., ribosome binding site).

An expression cassette or vector also can optionally include a transcriptional and/or translational termination region (i.e., termination region) that is functional in plants, yeast, or bacteria. A variety of transcriptional terminators is available for use in expression cassettes or vectors disclosed herein. The termination region may be native to the transcriptional initiation region, may be native to the operably linked nucleotide sequence of interest, may be native to the host cell, or may be derived from another source (i.e., foreign or heterologous to the promoter, the nucleotide sequence of interest, the host cell, or any combination thereof). Non-limiting examples of transcriptional terminators useful for plants can be a CAW 35S terminator, a tml terminator, a nopaline synthase terminator and/or a pea rbcs E9 terminator, a RubisCo small subunit gene 1 (TrbcSl) terminator, an actin gene (Tactin) terminator, a nitrate reductase gene (Tnr) terminator, and/or aa duplicated carbonic anhydrase gene 1 (Tdcal) terminator.

The choice of vector used for constructing a recombinant DNA molecule depends on the functional properties desired, e.g., replication, protein expression, and the host cell to be transformed. In one embodiment, the vector comprises a prokaryotic replicon, i.e., a DNA sequence having the ability to direct autonomous replication and maintenance of the recombinant DNA molecule extra-chromosomally when introduced into a prokaryotic host cell, such as a bacterial host cell. In addition, the vector may also comprise a gene whose expression confers a selective advantage, such as a drug resistance, to the bacterial host cell when introduced into those transformed cells. Suitable bacterial drug resistance genes are those that confer resistance to ampicillin or tetracycline, among other selective agents. The neomycin phosphotransferase gene has the advantage that it is expressed in eukaryotic as well as prokaryotic cells.

Vectors typically include convenient restriction sites for insertion of a recombinant DNA molecule. Suitable vector plasmids include pUC8, pUC9, pBR322, and pBR329 available from BioRad Laboratories (Richmond, Calif.) and pPL, pK and K223 available from Pharmacia (Piscataway, N.J.), and pBLUESCRIPT® and pBS available from Stratagene (La Jolla, Calif.). Other exemplary vectors include pCMU. Other appropriate vectors may also be synthesized, according to known methods; for example, vectors pCMU/Kb and pCMUII which are modifications of pCMUIV.

Suitable expression vectors capable of expressing a recombinant nucleic acid sequence in plant cells and capable of directing stable integration within the host plant cell include vectors derived from the tumor-inducing (Ti) plasmid of *Agrobacterium tumefaciens*, and several other expression vector systems known to function in plants. See for example, Verma et al., No. WO87/00551, incorporated herein by reference Other suitable expression vectors include gateway cloning-compatible plant destination vectors for expression of proteins in transgenic plants, e.g., the pEarleygate series (Earley et al. The Plant Journal Volume 45, Issue 4, pages 616-629, February 2006) or gateway pDONR entry vectors.

Expression cassettes and expression vectors optionally contain a selectable marker, which can be used to select a transformed plant, plant part, and/or host cell. As used herein, "selectable marker" means a nucleotide sequence that when expressed imparts a distinct phenotype to a plant, plant part and/or cell expressing the marker and thus allows such a transformed plant, plant part, and/or cell to be distinguished from that which does not have the marker. Such a nucleotide sequence may encode either a selectable or screenable marker, depending on whether the marker confers a trait that can be selected for by chemical means, such as by using a selective agent (e.g., an antibiotic, herbicide, or the like), or whether the marker is simply a trait that one can identify through observation or testing, such as by screening (e.g., the R-locus trait). Of course, many examples of suitable selectable markers are known in the an and can be used in the expression cassettes described herein. Although such a marker gene may be carried on another polynucleotide sequence co-introduced into the host cell, it is most often contained on the cloning vector. Only those host cells into which the marker gene has been introduced will survive and/or grow under selective conditions. Suitable selection genes encode proteins that (a) confer resistance to antibiotics or other toxic substances, e.g., ampicillin, neomycin, methotrexate, etc.; (b) complement auxotrophic deficiencies; or (c) supply critical nutrients not available from complex media. The choice of the proper selectable marker will depend, in part, on the host cell.

Examples of selectable markers include, but are not limited to, a nucleotide sequence encoding aadA (i.e., spectinomycin and streptomycin resistance), a nucleotide sequence encoding neo (i.e., kanamycin resistance), a nucleotide sequence encoding aphA6 (i.e., kanamycin resistance), a nucleotide sequence encoding nptll (i.e., kanamycin resistance), a nucleotide sequence encoding bar (i.e., phosphinotricin resistance), a nucleotide sequence encoding cat (i.e., chloramphenicol resistance), a nucleotide sequence encoding badh (i.e., betaine aldehyde resistance), a nucleotide sequence encoding egfp, (i.e., enhanced green fluorescence protein), a nucleotide sequence encoding gfp (i.e., green fluorescent protein), a nucleotide sequence encoding a red fluorescent protein (e.g., mCherry or DsRed) a nucleotide sequence encoding luc (i.e., luciferase), a nucleotide sequence encoding ble (bleomycin resistance), a nucleotide sequence encoding ereA (erythromycin resistance), and any combination thereof.

Further examples of selectable markers useful with the invention include, but are not limited to, a nucleotide sequence encoding an altered 5-enolpyruvylshikimate-3-phosphate (EPSP) synthase, which confers resistance to glyphosate (Hinchee et al. (1988) Biotech. 6:915-922), a nucleotide sequence encoding a nitrilase such as bxn from *Klebsiella ozaenae* that confers resistance to bromoxynil (Stalker et al. (1988) Science 242.419-423); a nucleotide sequence encoding an altered acetolactate synthase (ALS) that confers resistance to imidazolinone, sulfonylurea or other ALS-inhibiting chemicals (EP Patent Application No 154204); a nucleotide sequence encoding a methotrexate-resistant dihydrofolate reductase (DHFR) (Thillet et al (1988) J Biol. Chem. 263:12500-12508); a nucleotide sequence encoding a dalapon dehalogenase that confers resistance to dalapon; a nucleotide sequence encoding a mannose-6-phosphate isomerase (also referred to as phosphomannose isomerase (PMI)) that confers an ability to metabolize mannose (U.S. Pat. Nos. 5,767,378 and 5,994,629); a nucleotide sequence encoding an altered anthranilate synthase that confers resistance to 5-methyl tryptophan; and/or a nucleotide sequence encoding hph that confers resistance to hygromycin.

Additional selectable markers include, but are not limited to, a nucleotide sequence encoding β-glucuronidase or uidA (GUS) that encodes an enzyme for which various chromogenic substrates are known, an R-locus nucleotide sequence that encodes a product that regulates the production of anthocyanin pigments (red color) in plant tissues (Dellaporta et al, "Molecular cloning of the maize R-nj allele by transposon-tagging with Ac" 263-282 In: Chromosome Structure and Function: Impact of New Concepts, 18th Stadler Genetics Symposium (Gustafson & Appels eds, Plenum Press 1988)); a nucleotide sequence encoding β-lactamase, an enzyme for which various chromogenic substrates are known {e.g., PAD AC, a chromogenic cephalosporin) (Sutcliffe (1978) Proc Natl Acad, Sci. USA 75:737-3741); a nucleotide sequence encoding xylE that encodes a catechol dioxygenase (Zukowsky et al (1983) Proc Natl. Acad Sex. USA 80:1101-1105); a nucleotide sequence encoding tyrosinase, an enzyme capable of oxidizing tyrosine to DOPA and dopaquinone, which in turn condenses to form melanin (Katz et al. (1983) J Gen. Microbiol. 129:2"/'03-21 ! 4); a nucleotide sequence encoding β-galactosidase, an enzyme for which there are chromogenic substrates; a nucleotide sequence encoding luciferase (lux) that allows for bioluminescence detection (Ow et al. (1986) Science 234:856-859); a nucleotide sequence encoding Bla that confers ampicillin resistance; or a nucleotide sequence encoding aequorin which may be employed in calcium-sensitive bioluminescence detection (Prasher et al. (1985) Biochem. Biophys. Res. Comm. 126:1259-1268), and/or any combination thereof. One of skill in the art is capable of choosing a suitable selectable marker for use in an expression cassette of this invention.

One of the most commonly used markers for the selection of transgenic plants is resistance to glufosinate ammonium, an herbicide that is sold under a variety of trade names including Basta and Finale. Resistance to glufosinate ammonium is conferred by the bacterial bialophos resistance gene (BAR) encoding the enzyme phosphinotricin acetyl transferase (PAT) The major advantage of glufosinate ammonium selection is that it can be performed on plants growing in soil and does not require the use of sterile techniques.

Transformation of a host cell with an expression vector or other DNA is carried out by conventional techniques known in the art. By "transformation" is meant a permanent or transient genetic change induced in a cell following incorporation of new DNA (i.e., DNA exogenous to the cell). Where the cell is a plant cell, a permanent genetic change is generally achieved by introduction of the DNA into the genome of the cell. By "transformed cell" or "host cell" is meant a cell (e.g., prokaryotic or eukaryotic) into which (or into an ancestor of which) has been introduced, by means of recombinant DNA techniques, a DNA molecule encoding a DGAT1, GPD1, MGAT1, and/or PDCT1 polypeptide or a suppressor of SDP1 expression, or fragment thereof.

The method of transformation in obtaining such transgenic plants is not critical, and various methods of plant transformation are currently available. Furthermore, as newer methods become available to transform crops, they may also be directly applied hereunder. For example, many plant species naturally susceptible to Agrobacterium infection may be successfully transformed via tripartite or binary vector methods of Agrobacterium mediated transformation. In many instances, it will be desirable to have the construct bordered on one or both sides by T-DNA, particularly having the left and right borders, more particularly the right border. This is particularly useful when the construct uses *A. tumefaciens* or *A. rhizogenes* as a mode for transformation, although the T-DNA borders may find use with other modes of transformation. In addition, techniques of microinjection, DNA particle bombardment, and electroporation have been developed which allow for the transformation of various monocot and dicot plant species.

In addition to transformation technology, traditional breeding methods as known in the art (e.g., crossing) can be used to assist in introducing into a single plant each of the expression cassettes described herein o produce a plant, plant part, and/or plant cell comprising and expressing each of the recombinant polynucleotides as described herein.

Recombinant host cells, in the present context, are those that have been genetically modified to contain a heterologous DNA molecule. The DNA can be introduced by a means that is appropriate for the particular type of cell, including without limitation, transfection, transformation, lipofection, or electroporation.

A "transgenic plant" is one that has been genetically modified to contain and express recombinant DNA sequences, either as regulatory RNA molecules or as proteins. As specifically exemplified herein, a transgenic plant is genetically modified to contain and express a recombinant DNA sequence operatively linked to and under the regulatory control of transcriptional control sequences that function in plant cells or tissue or in whole plants. As used herein, a transgenic plant also encompasses progeny of the initial transgenic plant where those progeny contain and are capable of expressing the recombinant coding sequence under the regulatory control of the plant-expressible transcription control sequences described herein. Seeds containing transgenic embryos are encompassed within this definition.

Individual plants within a population of transgenic plants that express a recombinant gene may have different levels of gene expression. The variable gene expression is due to multiple factors including multiple copies of the recombinant gene, chromatin effects, and gene suppression. Accordingly, a phenotype of the transgenic plant may be measured as a percentage of individual plants within a population. In one embodiment, greater than or equal to about 25% of the transgenic plants express the phenotype. Specifically, greater than or equal to about 50% of the transgenic plants express the phenotype More specifically, greater than or equal to about 75% of the transgenic plants express the phenotype. The phenotype is preferably increased oil content of the plant or seeds of the plant or increased seed yield of the plant.

The transgenic plant has been transformed with an expression cassette comprising a protein or functional nucleic acid coding sequence operatively linked to a plant-expressible transcription regulatory sequence.

A recombinant DNA construct including a plant-expressible gene or other DNA of interest is inserted into the genome of a plant by a suitable method. Suitable methods include, for example, *Agrobacterium tumefaciens*-mediated DNA transfer, direct DNA transfer, liposome-mediated DNA transfer, electroporation, co-cultivation, diffusion, particle bombardment, microinjection, gene gun, calcium phosphate coprecipitation, viral vectors, and other techniques. Suitable plant transformation vectors include those derived from a Ti plasmid of *Agrobacterium tumefaciens*. In addition to plant transformation vectors derived from the Ti or root-inducing (Ri) plasmids of Agrobacterium, alternative methods can be used to insert DNA constructs into plant cells A transgenic plant can be produced by selection of transformed seeds or by selection of transformed plant cells and subsequent regeneration.

In one embodiment, the coding sequence of interest, for example a coding sequence for a DGAT1, GPD1, MGAT1, and/or PDCT1 polypeptide and/or a suppressor of SDP1 expression, is subcloned under the control of a seed-specific promoter, such as the glycinin promoter, and the 3' OCS terminator into the plant expression binary vector pBnRGW RedSeed, which has a Bar gene for BASTA resistance selection in plants, a gene for spectinomycin resistance in bacterial selection, and expresses the DsRed fluorescent protein under a napin promoter for identification of transformants by red fluorescence in seeds. *Camelina sativa* is transformed using vacuum infiltration technology, and the T1 generation seeds are screened for BASTA resistance and/or red fluorescence. Transgenic plants transformed with the heterologous polynucleotide are produced. In one embodiment, the plant also expresses one or more additional heterologous coding sequences.

The transgenic plants are grown (e.g., on soil) and harvested. In one embodiment, above ground tissue is harvested separately from below ground tissue. Suitable above ground tissues include shoots, stems, leaves, flowers, grain, and seed. Exemplary below ground tissues include roots and root hairs. In one embodiment, whole plants are harvested and the above ground tissue is subsequently separated from the below ground tissue.

The terms "increase," "increasing," "increased," "enhance," "enhanced," "enhancing," and "enhancement" (and grammatical variations thereof), as used herein, describe an elevation in gene expression or a phenotypic trait in a plant, plant cell and/or plant part as compared to a control as described herein. This increase can be observed by comparing the increase in expression or the phenotypic trait in the plant, plant part or plant cell transformed with, for example, one or more expression cassettes disclosed herein to the appropriate control (e.g., the same plant, plant part, and/or plant cell lacking (i.e., not transformed with) the one or more heterologous polynucleotides).

As used herein, the terms "reduce." "reduced," "reducing," "reduction," "diminish," "suppress," and "decrease" (and grammatical variations thereof), describe, for example, a decrease in gene expression or a phenotypic trait in a plant, plant cell and/or plant part as compared to a control as described herein.

The term "suppressor" as used herein, means a molecule (e.g., a polynucleotide or polypeptide) that when incorporated into a plant, plant part, or plant cell can "reduce," "diminish," "suppress," and "decrease" the activity of another molecule (e.g., a polynucleotide or polypeptide) as compared to a control (e.g., a plant, plant part and/or plant cell that does not comprise said suppressor). Thus, a heterologous polynucleotide encoding a suppressor of SDP1 can comprise a polypeptide that suppresses SDP1 or it can encode a functional nucleic acid (e.g., RNAi) that suppresses SDP1.

As used herein, the terms "express," "expression," and the like, with respect to a nucleotide sequence (e.g., RNA or DNA) indicates that the nucleotide sequence is transcribed and, optionally, translated. Thus, a nucleotide sequence may express a polypeptide of interest or a functional untranslated RNA. A "functional" RNA includes any untranslated RNA that has a biological function in a cell, e.g., regulation of gene expression Such functional RNAs include but are not limited to RNAi (e.g., siRNA, shRNA, antisense RNA), miRNA, ribozymes, RNA aptamers, and the like.

As used herein, the term "overexpression" means increased expression over that in the control. In some embodiments, "overexpression" can include expression of a heterologous polynucleotide not normally expressed in an organism. In other embodiments, overexpression can include expression of an endogenous polynucleotide in a transgenic expression cassette such that the amount of the endogenous polypeptide produced as a result of the endogenous polynucleotide in the transgenic expression cassette is greater than is produced in the organism not transformed with the expression cassette.

As used herein, "modifying" or "engineering" the plant's endogenous SDP1 gene to reduce the SDP1 activity of the modified or engineered gene includes not only the production of a SDP1 polypeptide having reduced activity but also includes modification or engineering of the SDP1 gene such that expression of the SDP1 polypeptide is reduced. An exemplary *Camelina sativa* SDP1 gene sequence for modification or engineering includes SEQ II) No:5.

The suppressor can be an antisense RNA complementary to the messenger RNA (mRNA) of the endogenous SDP1. The suppressor can be an RNAi nucleic acid that reduces expression of the SDP1 mRNA When the transgenic plant is a *Camelina sativa*, the suppressor preferably comprises SEQ ID NO:13.

Methods for developing antisense silencing constructs or inhibitors generally are well known in the art. Based on the nucleotide sequence encoding SDP1, antisense nucleotide sequences can be prepared. Thus, for example, a SDP1 coding sequence from *Camelina sativa* can be used to prepare RNAi for silencing the SDP1 gene. An exemplary RNAi suppressor of SDP1 can be a sequence-specific inverted repeat (sense-intron-antisense).

In other embodiments, the activity of SDP1 can be repressed by knocking out the endogenous SDP1 gene using methods known in the art. Thus, as an alternative to silencing endogenous SDP1 through the introduction of a heterologous nucleotide sequence encoding a functional nucleic acid (e.g., RNAi, antisense, amiRNA), endogenous SDP1 of a plant can be modified to be non-functional (i.e., knocked-out) or to have reduced activity using known methods, for example, Zinc finger nuclease (ZFN) technology (see, e.g., Umov et al. Genome editing with engineered zinc finger nucleases. Nature Reviews 11:636-646 (2010)); Transcription Activator-Like Effector Nuclease (TALEN) technology (see, e.g., Miller, J C. et al A TALE nuclease architecture for efficient genome editing. Nat. Biotechnol 29, 143-148 (2011); and Christian, M. et al. Targeting DNA double-strand breaks with TAL effector nucleases. Genetics 186, 757-761 (2010)); the CRJSPR/Cas system (see, e.g., Jiang, W., Bikard, D., Cox, D., Zhang, F. & Marraffini, L. A. RNA-guided editing of bacterial genomes using CRISPR-Cas systems Nat. Biotechnol 31, 233-239 (2013)); and engineered meganucleases technology (see, e.g., Antunes et al. Targeted DNA excision in Arabidopsis by a re-engineered homing endonuclease. BMC Biotechnology 12:86 (2012)).

Accordingly, in some embodiments methods are provided for producing a transgenic plant by suppressing the plant's endogenous SDP1 using, for example, RNAi technology, or by modifying or engineering an endogenous SDP1 gene by, for example, genome editing or mutation, so that the activity of the endogenous SDP1 is reduced, or eliminated.

Any method of modifying an endogenous nucleotide sequence or gene in a cell can be used to modify an endogenous SDP1 gene in a plant cell to produce a plant cell having an endogenous SDP1 gene encoding a polypeptide having reduced or no SDP1 activity. In representative embodiments, the endogenous SDP1 is modified using the CRISPR-Cas system. The plant cell can be a seed cell. In some embodiments, the activity of the modified endogenous SDP1 in a plant cell is reduced by at least about 10% to about 100%. Thus, in some embodiments, the activity of the modified endogenous SDP1 in a plant cell is reduced by about 10%, 11%. 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 36%, 39%, 40%, 41%, 42%, 43%, 44%, 45%, 46%, 47%, 48%, 49%, 50%, 55%, 60%, 65%, 70%, 75%, 80%, 85%, 90%, 95%, 100%, and the like, and any value or range therein.

The compositions and methods disclosed herein are further illustrated by the following non-limiting examples, which are merely illustrative and are not intended to limit the scope hereof. Any variations in the exemplified compositions and methods that occur to the skilled artisan are intended to fall within the scope of the present invention.

EXAMPLES

Example 1. Engineering Camelina Lines Co-Expressing a Modified Diacylglycerol Acyltransferase 1 (DGAT1m) and Glycerol-3-Phosphate Dehydrogenase (GDP1)

In this example, we have developed Camelina lines co-expressing a modified diacylglycerol acyltransferase 1 (DGAT1m) and glycerol-3-phosphate dehydrogenase (GDP1), with various combinations of seed-specific promoters and terminators, which are considered to be the rate limiting steps in the Kennedy pathway for enhanced triacylglycerol (TAG) yields in seeds. We have developed Camelina lines that show more than 50% increase in seed yield and an approximately 15% increase in oil contents in greenhouse conditions. Further, we have validated the results in the field trials. The field grown Camelina transgenic lines expressing DGA1 and GPD1 individually and stacked DGAT1m+GPD1, showed almost double seed yield and 14-15% increase in oil contents.

1. Cloning of GPD1, DGAT1, and Modified DGAT1 (DGAT1m) Genes

These three genes (gpd1 or G3PDH from *Sachharomyces cerevisae*; AY598968.1, and DGAT1 and modified DGAT1 (DGAT1m in with an amino acid substitution-S205A; genes from *Arabidopsis thaliana*; AT2G19450; NP_179535.1) were synthesized commercially and cloned into Gateway pDONR entry vectors using B5 and B2 recombinase sites with BP clonase reaction to create Entry clones for Gateway cloning. Gene sequences were confirmed by sequencing and PCR amplification.

2. Cloning of Glycinin and Oleosin Promoter Sequences

Glycinin promoter sequences from Soybean (*Glycin max*; X15121.1) and oleosin promoter sequences from both soybean (AC185960.11) and *Brassica rapa* (M63985.1) were amplified using synthetic oligos and cloned into Gateway pDONR entry vectors using B1 and B5r recombinase sites with BP clonase reaction. Promoter sequences were confirmed by sequencing and PCR amplification.

3. Generation of Plant Transformation Vectors

Plant transformation vectors for three genes (G3PDH, DGAT1 and DGAT1m were generated by recombining the individual entry clones containing glycinin promoter from soybean and oleosin promoter from *B. rapa* and soybean and individual entry clones containing three genes into a destination vector, pBnRGW RedSeed (FIGS. 1*a, b, c, & d*). Vector pBnRGW Redseed has a Bar gene for BASTA tolerance selection in plants and spectinomycin for bacterial selection. This vector also expresses DsRed under napin promoter for red fluorescence in seeds to identify the transformants. Cloning of the promoter and gene fragments in the destination vector was carried out using the MultiSite Gateway Pro 2-Fragment Recombination system from Invitrogen. Cloning of promoter and gene sequences into destination vectors were confirmed by restriction digestion of destination vector, sequencing, and PCR amplification of individual genes.

4. Generation of Gene Stacking Vectors

Expression of each gene in the stacking vector requires promoter, coding region, and a terminator fragment. Therefore, combining the two genes with two promoters and two terminator fragments requires 6 individual fragments to be cloned into a single vector. There is no Gateway vector system available for 6 fragment recombination. Therefore, to achieve this goal to combine the expression of GPD1 and DGAT1 or GPD1 and DGAT1m in a single construct, we modified pCAMBIA1300 binary vector by cloning a multiple cloning sites fragment to accommodate these genes along with promoter and terminator fragments. Further, in order to identify the transformants, we have also cloned Napin::DsRed fragment into this gene stacking vector within the T-DNA borders for screening the transgenic Camelina seeds. This gene-stacking vector is designated as pCAMBIA-DsRed-MCS (pSC101). This unique gene stacking vector can be used to stack up to 13 genes (39 individual fragments of promoter, coding region and terminator). Coding region of GDP1, DGAT1, and DGAT1m along with promoter and terminator fragments were synthesized commercially from GeneScript, Inc. GDP was cloned under soybean Oleosin promoter and DGAT1 and DGAT1m were cloned under soybean Glycinin promoter in the gene stacking vector (FIG. 2). These stacked gene constructs were transformed into plants.

5. Plant Transformation:

*Camelina sativa* cv Suneson plants were transformed with following vectors using *Agrobacterium*-mediated vacuum infiltration flower dip method following the method described in Lu and Kang (Plant Cell Rep, 2008, 27:273-278). Plants were transformed using these single gene constructs or in combination.

Figure 3:
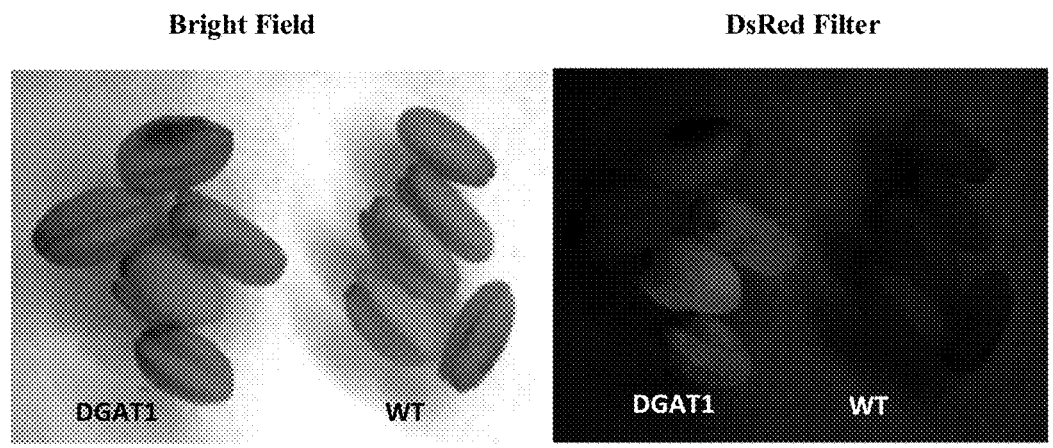
FIG. 3 shows images screening transgenic Camelina T1 seeds for those expressing DsRed under seed-specific Napin promoter. A. DGAT1 and wild type seeds under bright light. B. DGAT1 and wild type seeds with DsRed filter.
Figure 4:
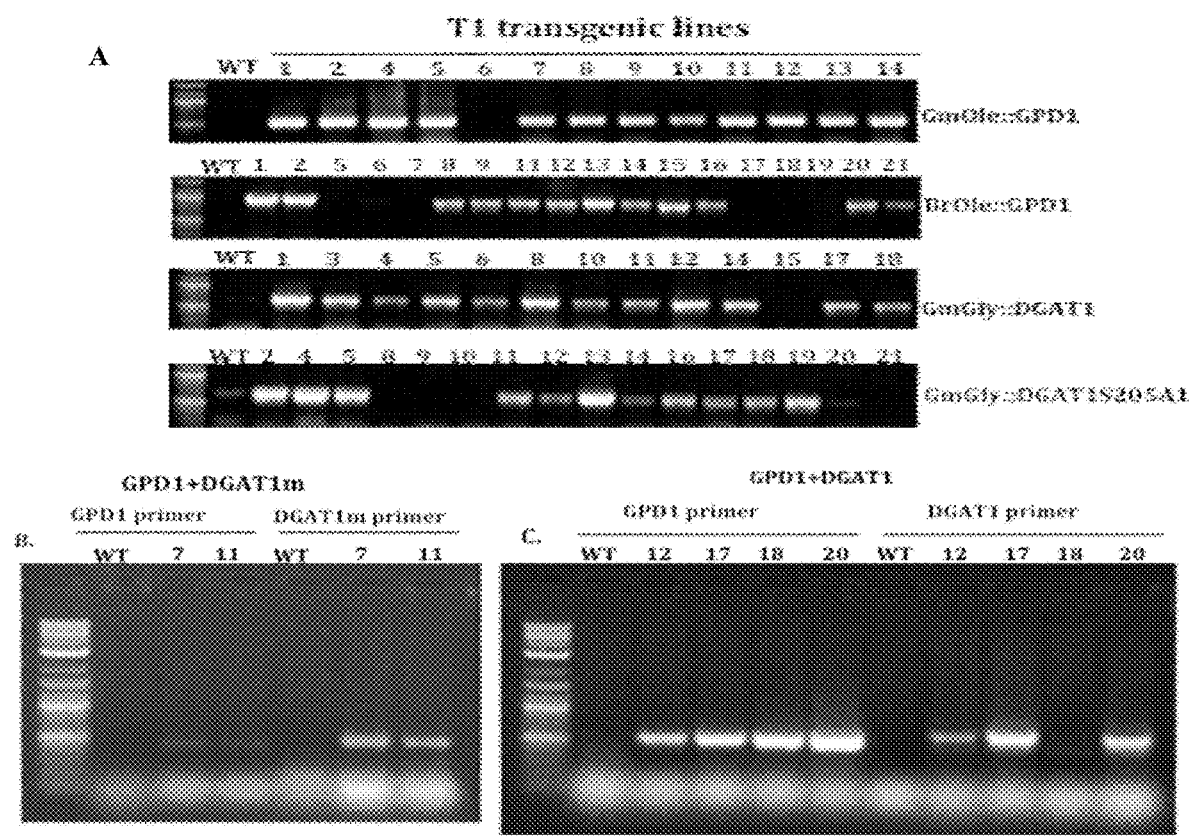
FIG. 4 shows images of electrophoresis data to genotype T1 lines. A. Genomic DNA PCR of representative T1 lines of transgenic Camelina plants expressing four gene constructs: Gm-Oleosin::G3PDH; Br-oleosin::G3PDH, Gm-glycinin::DGAT1, and Gm-glycinin::DGAT1S205A. B & C. Genomic DNA PCR of representative T1 lines of transgenic Camelina plants co-expressing GPD1+DGAT1m (B) and GPD1+DGAT1 (C).

Single Gene Constructs Transformed into Plant
i) Gm-Oleosin::G3PDH
ii) Br-oleosin::G3PDH
iii) Gm-glycinin::DGAT1
iv) Gm-glycinin::DGAT1m
Combined Gene Expression in Plants
GmOle::GPD1+GmGly::DGAT1
GmOle::GPD1+GmGly::DGAT1m Results Generating Transgenic Camelina and preliminary analysis of transgenic lines: Mature T1 seed from *Agrobacterium* transformed plants were collected and dried on the bench. A transformation efficiency ranging from 0.5-1% was obtained using the flower dip method. The Gateway binary vector (pBnRGW RedSeed) used for expression of transgenes contains DsRed expressed under a napin promoter for red fluorescence in seeds to identify the transformants. Therefore, transgenic seeds showing red fluorescence were selected from the T1 generation seeds for each construct (FIG. 3). Interestingly, for all constructs transgenic T1 seeds showing red fluorescence were significantly larger in size as compared to the non-transgenic wild type seeds (FIG. 3). Genotyping of the individual or stacked T1 transgenic lines by PCR of genomic DNA confirmed the presence of the transgenes (FIGS. 4 A, B & C). T1 seeds showing the DsRed expression for four gene constructs (Gm-Oleosin::G3PDH; Br-oleosin::G3PDH, Gm-glycinin::DGAT1, and Gm-glycinin::DGAT1m and stacked gene constructs were grown in soil to obtain the T2 seeds. For each constructs, we selected more than 20 independent T1 lines. Seeds of these T2 lines showing 3:1 Mendelian segregation ratio for DsRed fluorescence were selected for growing in to soil to obtain T3 homozygous lines. On average 16 seeds of each T2 line showing DsRed fluorescence were grown in soil.

Figure 5:
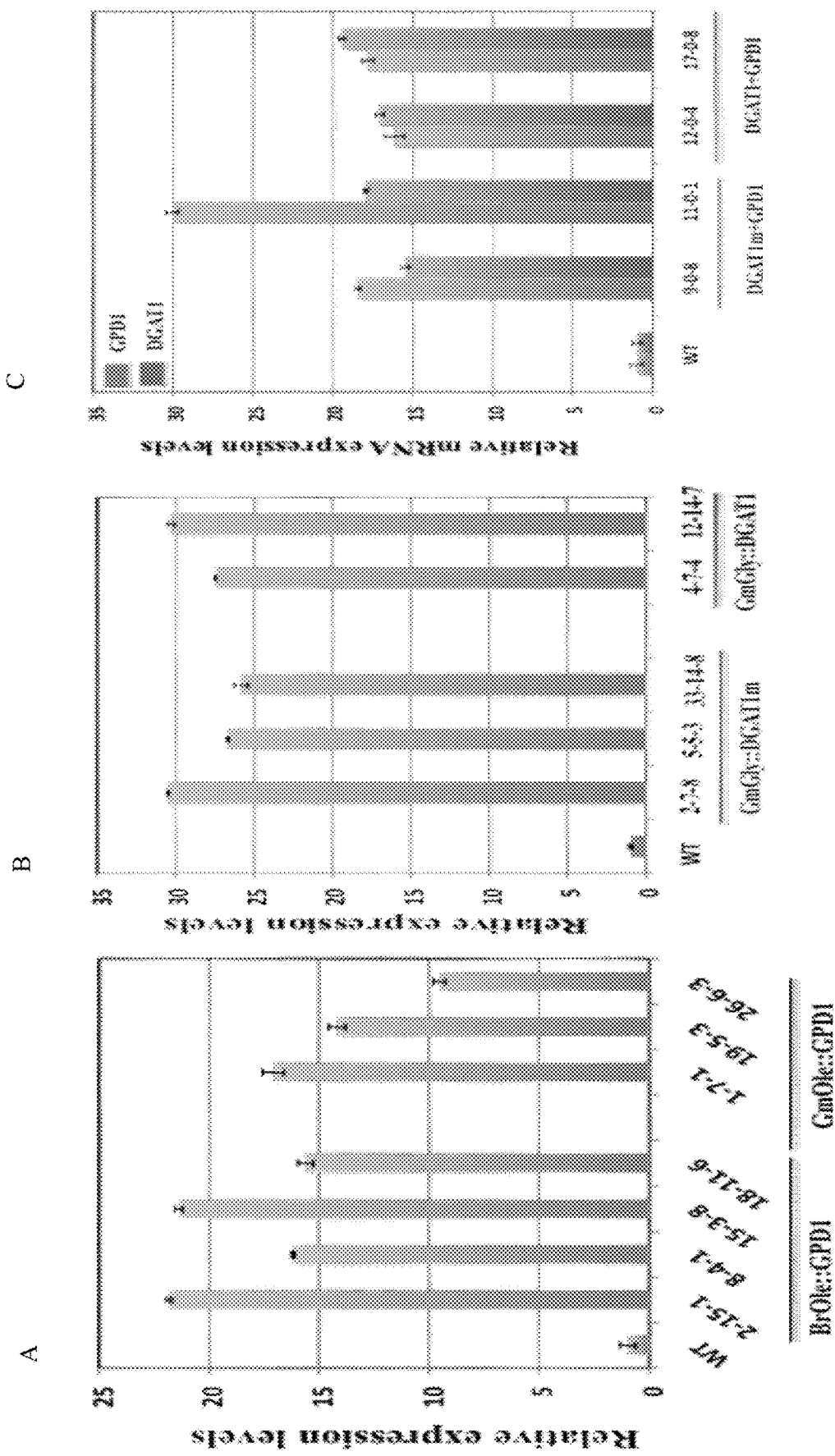
FIG. 5 is a bar chart of results of qRT-PCR analysis for expression of GPD1 (A), DGAT1 or DGAT1m (B), and GPD1+DGAT1 or GPD1+DGAT1m in stacked transgenic lines (C).

Confirmation of Gene expression: The expression of GPD1, DGTA1 and DGAT1m mRNA transcripts were confirmed using quantitative real-time PCR. RNA was extracted from the 10- to 21 days after flowering (DAF) developing seeds, converted to cDNA using cDNA synthesis kits and the resulting cDNA was used to carry out the qPCR. Our results showed the transgenic lines expressing these transgenes under seed-specific promoters showed more than 10-fold increase in transcripts in transgenic lines (FIG. 5).

Figure 6:
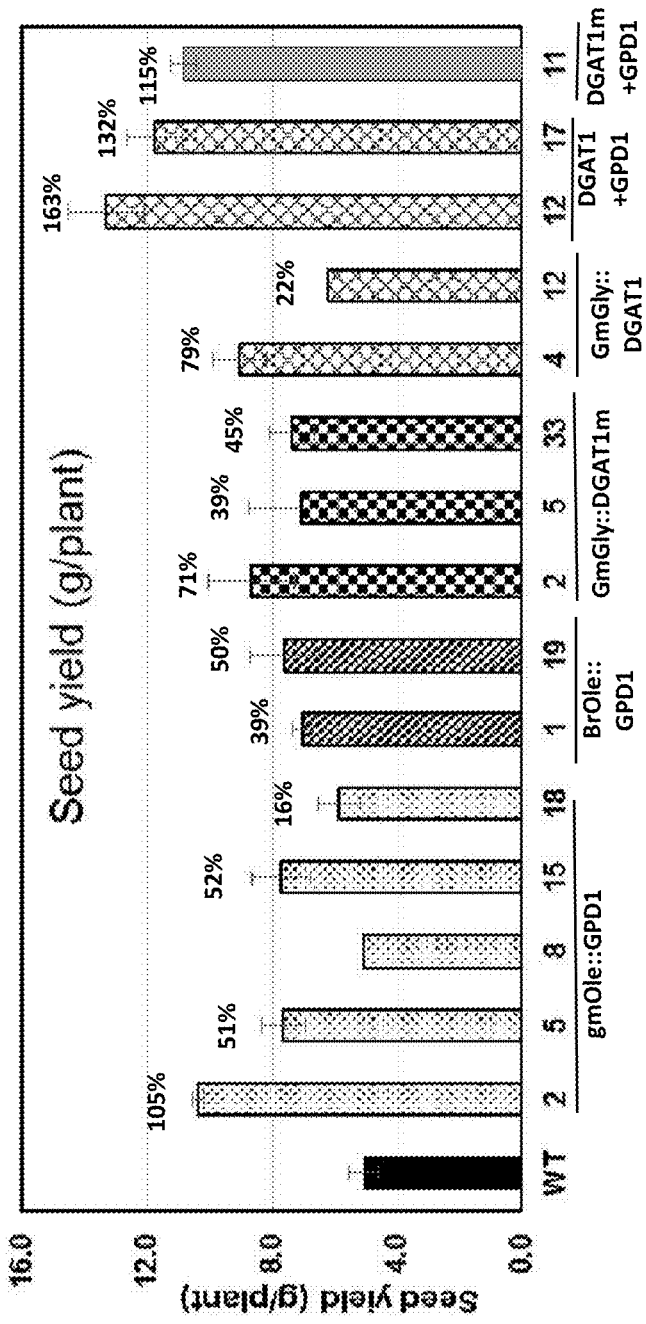
FIG. 6 is a bar chart of results of per plant seed yield analysis for GmOle::GPD1, BrOle::GPD1, GmGly::DGAT1, GmGly::DGAT1m, GPD1+DGAT1 and GPD1+DGAT1m in stacked transgenic lines.
Figure 7:
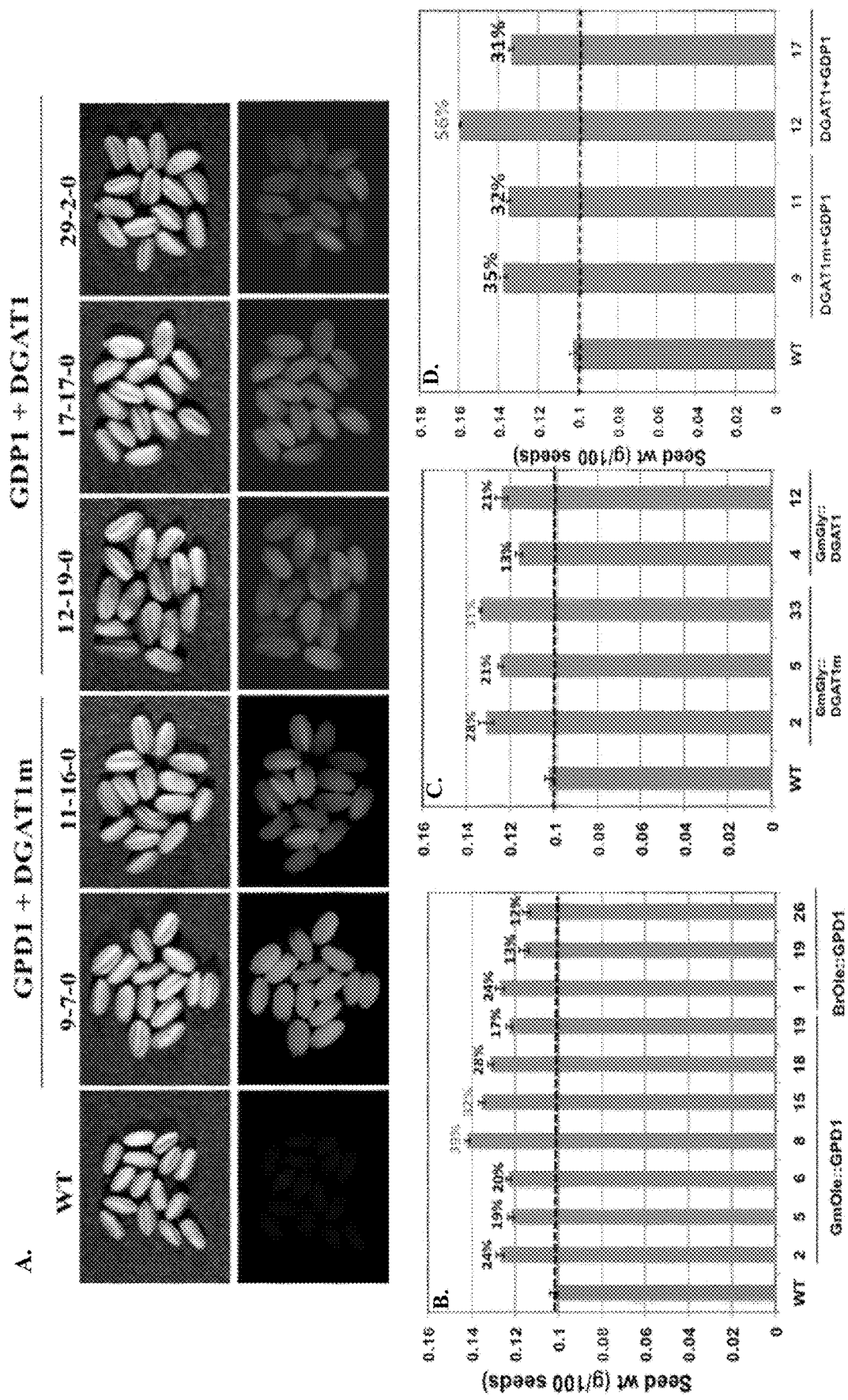
FIG. 7 shows results of analysis of seeds from T3 homozygous lines and Wild type plants. Panel A provides images of WT and Camelina$^{TAG}$ co-transformed T3 homozygous line seeds under bright field (upper row) and DsRed fluorescence (lower row). Panel B is a bar chart of average weight of 100 seeds from transgenic plants expressing GmOle::GPD1 or BrOle::GPD1 constructs. Panel C is a bar chart of average weight of 100 seeds from transgenic plants expressing GmGly::DGAT1 or GmGly::DGAT1m constructs. Panel D is a bar chart of average weight of 100 seeds from transgenic plants expressing stacked GPD1+DGAT1m or GPD1+DGAT1 constructs.

Analysis of T3 Homozygous Lines Seeds for Seed Yield, Seed Mass and Oil Contents Measure seed yield in T3 homozygous Camelina$^{TAG}$ lines: We analyzed per plant dry seeds weight of T3 homozygous lines. Analysis of total per plant seed yield showed that transgenic lines expressing GDP1, DGAT1, DGAT1m and stacked lines (GDP1+DGAT1 and GDP1+DGAT1m) had significantly higher seed yield and some lines showed more than double seed yield (FIG. 6). Seed of transgenic lines were also significantly bigger in size compared to wild type lines (FIG. 7). For individual constructs, our results showed that transgenic seeds attained 13-39% more weight as compared to wild type seeds (FIGS. 7 B and C). Homozygous lines for construct GmOleosin::GPD1 showed highest (39%) gain in seed weight, whereas, weight gain for GmGlycinin::DGAT1 and GmGlycinin::DGAT1m lines were ranging from 13-28%. The T3 homozygous lines for the gene stacked (co-transformed) showed the higher gain in seed weight than the lines for individual construct. Co-transformed lines for DGAT1+GPD1 showed up to 35% weight gain, whereas, lines for DGAT1m+GPD1 showed up to 56% weight gain in transgenic seeds (FIG. 7D). This increase in seed weight in T3 homozygous lines is consistent with seed weight increase in T1 and T2 lines.

Figure 8:
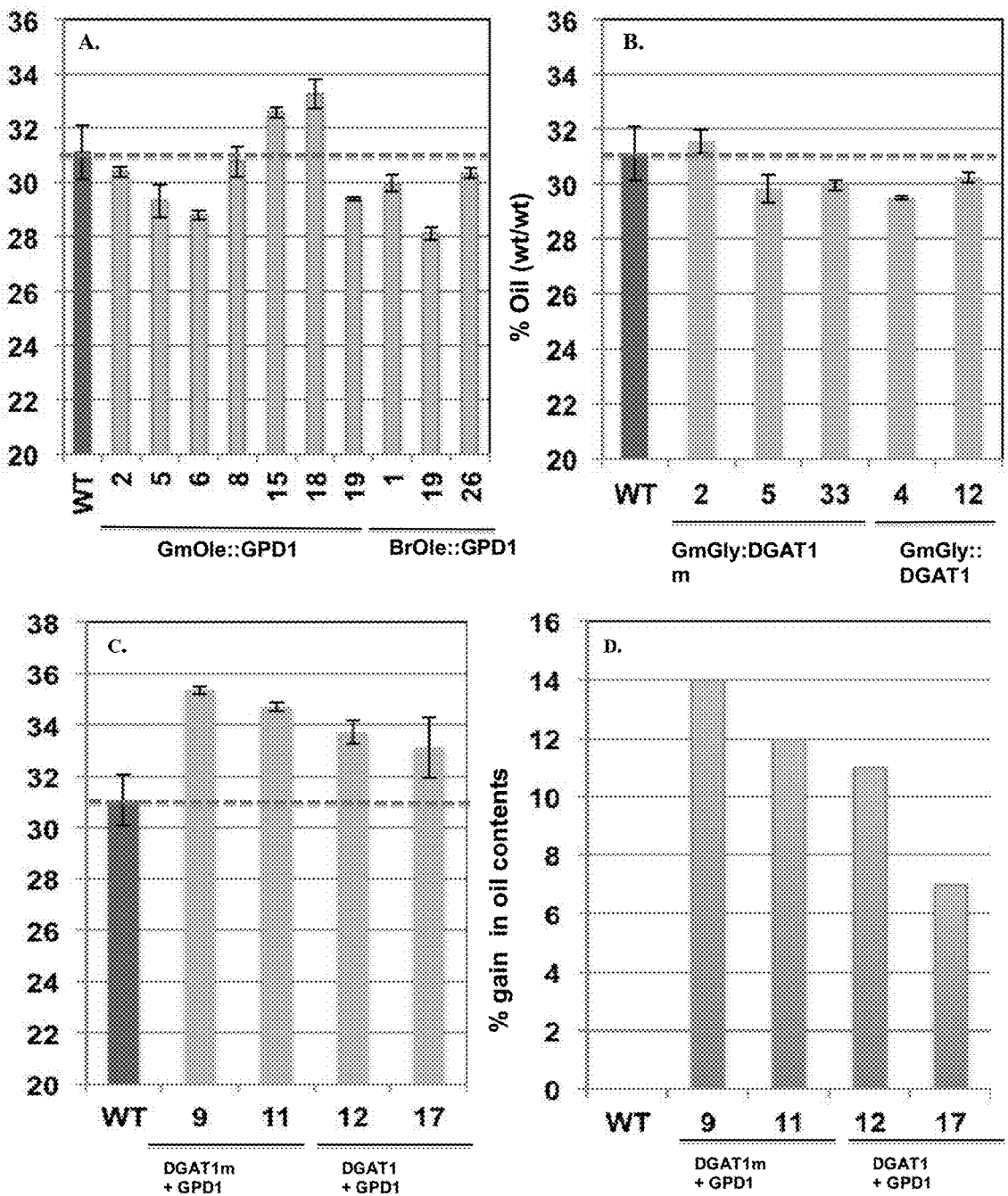
FIG. 8 presents bar charts showing the analysis of % Oil in seeds from T3 homozygous lines or Wild type plants. A. % oil contents in transgenic seeds from transgenic plants expressing GmOle::GPD or BrOle::GPD1 constructs. B. % oil in transgenic seeds from transgenic plants expressing GmGly::DGAT1 or GmGly::DGAT1S205A (DGAT1m) constructs. C. % oil in seeds from transgenic plants expressing stacked DGAT1m+GPD1 or DGAT1+GPD1 constructs. D. % oil gain in seeds from transgenic plants expressing stacked DGAT1m+GPD1 or DGAT1+GPD1 constructs compared to wild type plants.

Measurement of oil yield in T3 homozygous Camelina$^{TAG}$ lines: Total oil yield analysis of T3 homozygous Camelina-$^{TAG}$ lines was performed using Minispec mq-20 20 MHz NMR to quantify the levels (wt./wt.). Three replicate of 500 mg seeds for each line and wild type seeds was analyzed for total oil yield. Average oil content in wild type was 31%. Oil contents in seeds of individual gene contracts were almost similar to wild type except T3 homozygous lines 15 and 18 for GmOleosin::G3PDH which had 6 and 8% increase in oil, respectively, compared to wild type seeds (FIG. 8). For stacked lines, along with increase in seed yield, there is a significant increase in oil contents. Transgenic lines expressing DGAT1m+GPD1 showed 14% increase in oil contents and lines expressing DGAT1+GPD1 showed 11% increase in oil contents (FIG. 8C).

Figure 9:
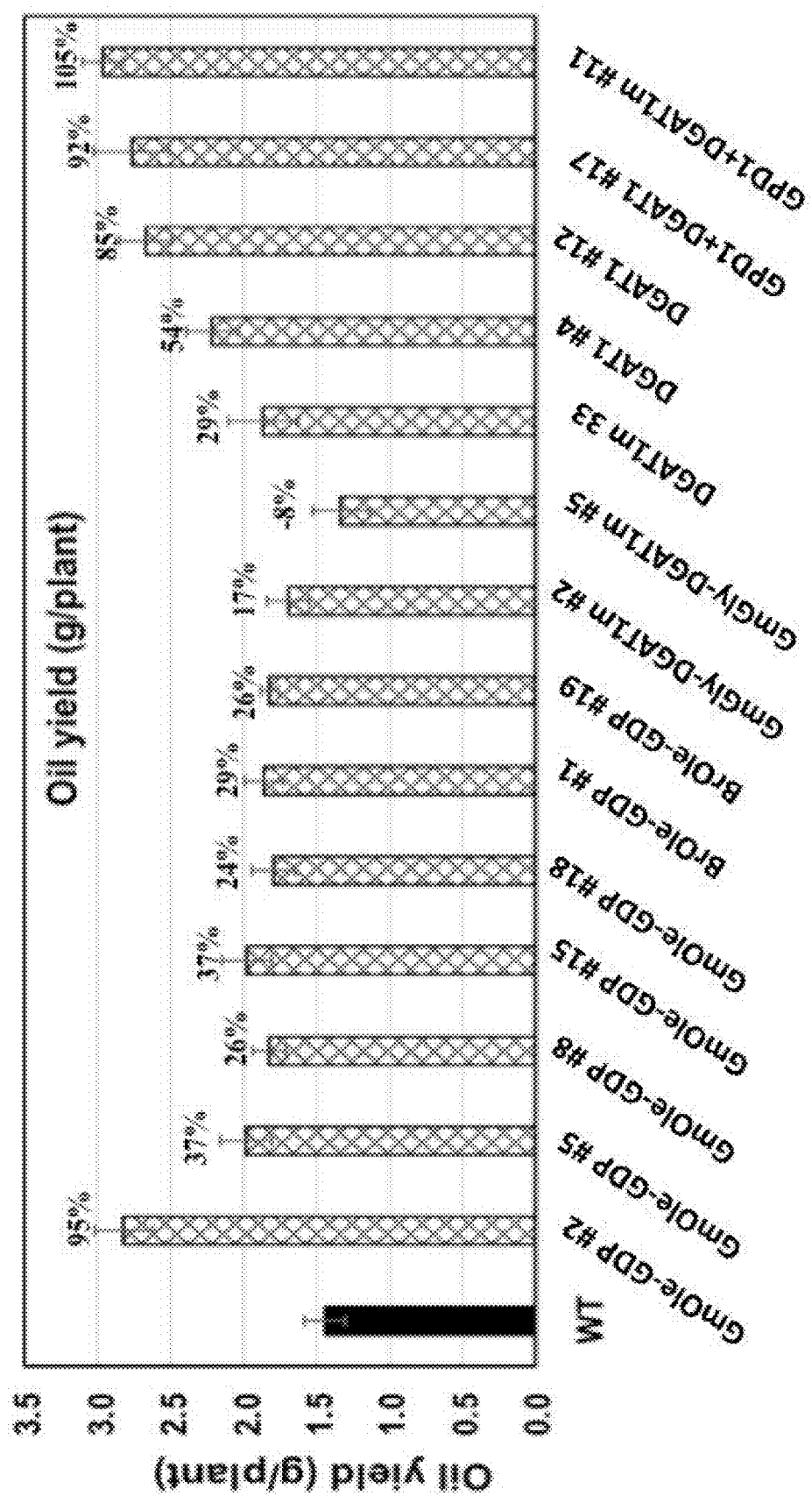
FIG. 9 is a bar graph showing per plant total oil yield (g/plant) in Wild type, T3 homozygous lines of GmOle:: GPD, BrOle::GPD1, GmGly::DGAT1 or GmGly::DGAT1m and T3 homozygous DGAT1m+GPD1 or DGAT1+GPD1 stacked gene lines.

We expressed the per plant total oil yield based on the % oil contents and total seed weight for all T3 homozygous lines for individual constructs as well as co-transformed T3 lines. As shown in FIG. 9, except DGP1 line 2, most of the single gene lines showed only an increase in a range from −8 to 37%, whereas the stacked lines (DHGAT1m+GPD1 and DGAT1+GPD1) showed almost double oil yield per plant basis as compared to wild type controls.

Validating the Greenhouse Results in Field Trials:

1. Field trials of Camelina$^{TAG}$ transgenic lines: We grew the best TAG lines in the field in the beginning of May, 2014. Each line was grown in 5 replicates along with wild type plants in a random plot design. The mature lines were harvested by Aug. 25, 2014. The analysis for seed mass, per plant seed weight, oil contents, oil yield per acre were carried out for these lines. These field trial results confirmed the results that were obtained in the greenhouse conditions for increased seed mass, per plant seed wt and oil yield. All these TAG lines in field trials showed a significant, even better than greenhouse conditions, increased in seed mass, seed weight and seed and oil yield.

Figure 10:
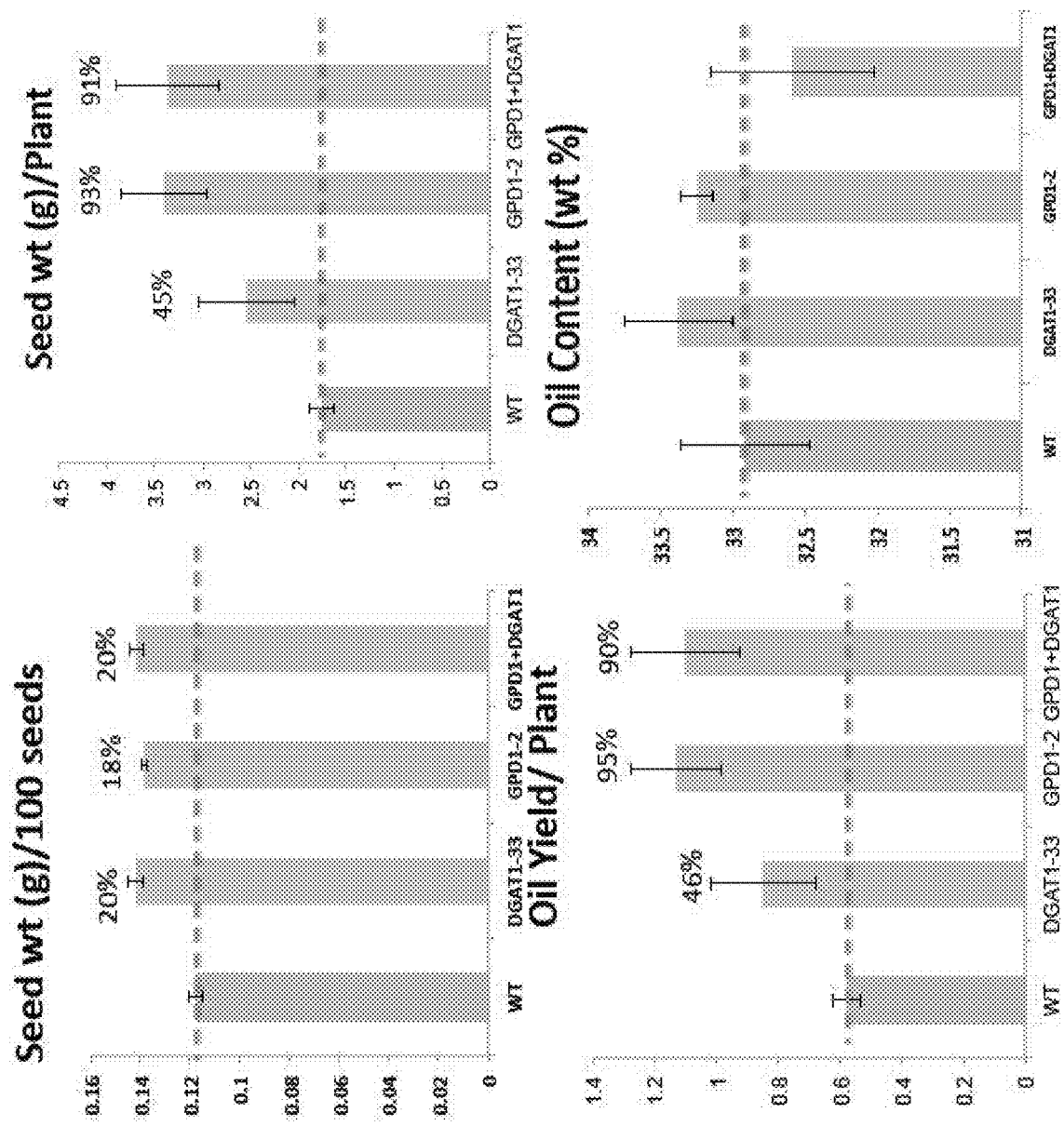
FIG. 10 is a series of bar charts showing the analysis of GPD1, DGAT1, and GPD1+DGAT1 TAG lines in comparison with wild type plants under field conditions. A. Seed wt (g)/100 seeds. B. Seed wt (g)/plant. C. Total oil contents. D. Per plant Oil yield (total Oil contents X total seeds wt per plant).

GPD1, DGAT1 and GPD1+DGAT1 lines showed more than 20% increase in seed mass and more than 90% increase in seed yield per plant basis (FIGS. 10 A & B). However, there was only marginal (approximately 3%) increase in oil contents (FIG. 10C). The seed yield per plant basis was lower in line DGAT1 #33 compared to GDP1 #2 and GPD1+DGAT1 lines, which showed almost double oil yield/per plant compared to wild type controls (FIG. 10 D). Therefore, analysis of GPD1, DGAT1 and GPD1+DGAT1 lines grown in field confirmed the increase in seed and oil yields.

Example 2. Effects of MGAT1, PDCT1, and SDP1 Expression on Seed and Oil Yield

To further increase the oil contents seeds yield in Camelina, we performed a comprehensive transcriptomics and metabolomics of DGAT1m and GPD1 transgenic lines and identified the key genes and gene networks.

We identified three additional genes, MGAT1, PDCT1, and SDP1, whose expression level affected seed yield and oil content in Camelina.

Figure 2A:
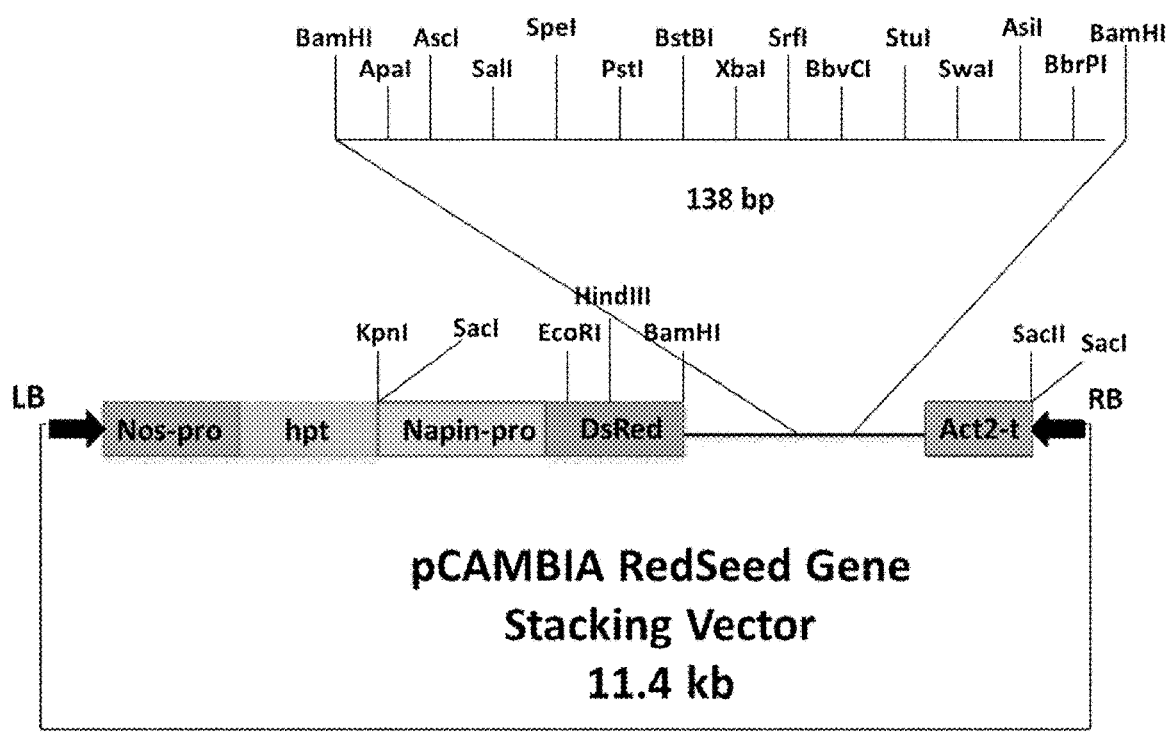
FIG. 2A is a schematic diagram of the pCambia RedSeed gene stacking vector (pSC101) with the 108 bp region containing multiple restriction sites for stacking multiple genes expanded. Additionally, for selection of transgenic seeds, a DsRed fluorescent gene under expression control by a Napin promoter (Napin-pro) from *Brassica* is also present.
Figure 2B:
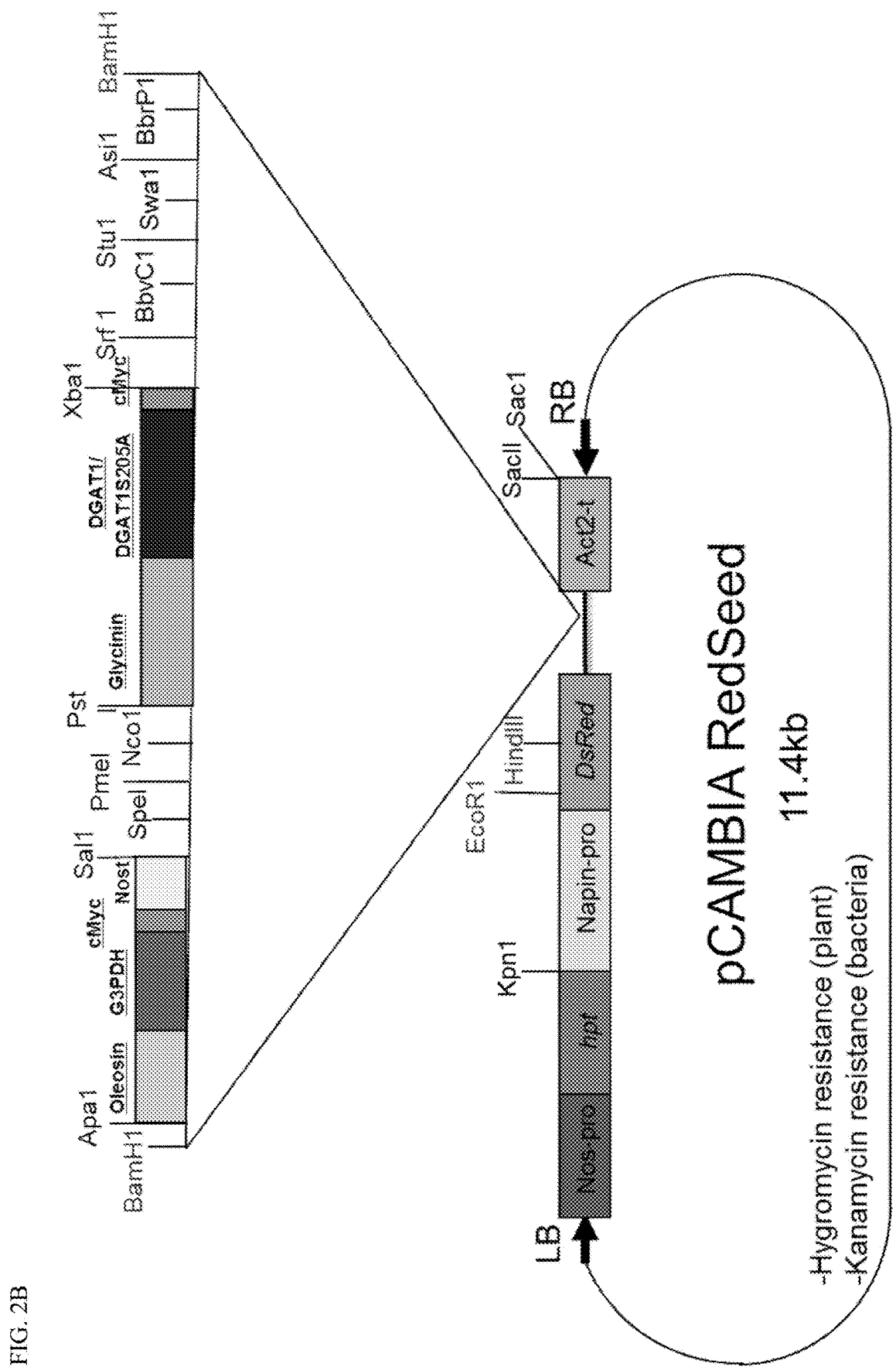
FIG. 2B is a representation of the gene stacking vector pCAMBIA-DsRed-MCS (pSC101) expressing yeast glyceraldehyde 3-phosphate dehydrogenase (G3PDH or GPD1) gene under a Oleosin promoter and either DGAT1 (Diacylglycerol 0-Acyltransferase 1) or DGAT1S205A under a glycinin promoter.
Figure 11:
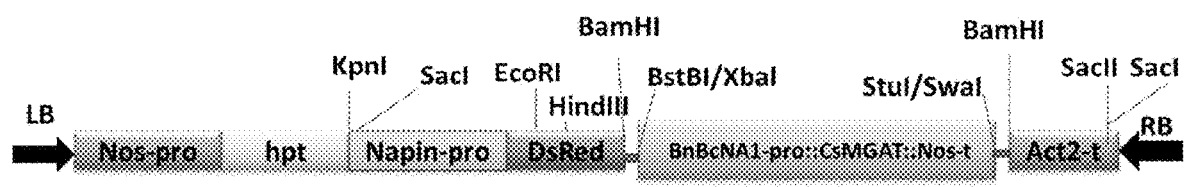
FIG. 11 schematically represents the gene constructs for expression of the MGAT1 gene (upper panel) under the *Brassica compestris* Napin 1 (NA1) promoter and Nos terminator and the PDCT1 gene (bottom panel) under the *Phaseolus vulgaris* phaseolin (Phas) promoter and Nos terminator.
Figure 11:
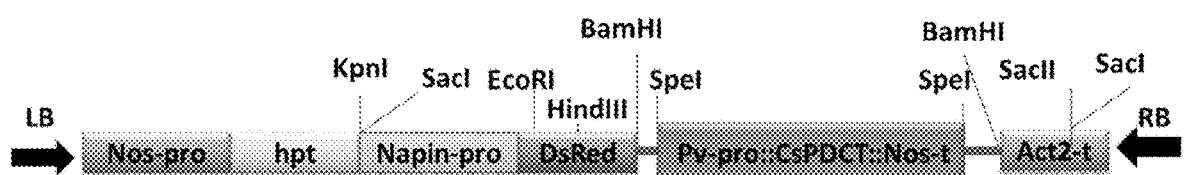

Three constructs were made in pCambia RedSeed (FIG. 2A). One was for overexpression of MGAT1 (FIG. 11, upper construct). Another construct was made for overexpression of PDCT1 (FIG. 11, middle construct). The third construct was for expression of SDP1 RNAi to reduce expression of the SDP1 gene (FIG. 11, bottom construct).

Camelina sativa cv Suneson plants were transformed with one of the three constructs using Agrobacterium-mediated vacuum infiltration flower dip method. Mature T1 seed from Agrobacterium transformed plants were collected and dried on the bench. T1 seeds showing expression for the three gene constructs were grown in soil to obtain the T2 seeds. For each construct, we selected more than 20 independent T1 lines. Seeds of these T2 lines showing 3:1 Mendelian segregation ratio for DsRed fluorescence were selected for growing in soil to obtain T3 homozygous lines.

Figure 12:
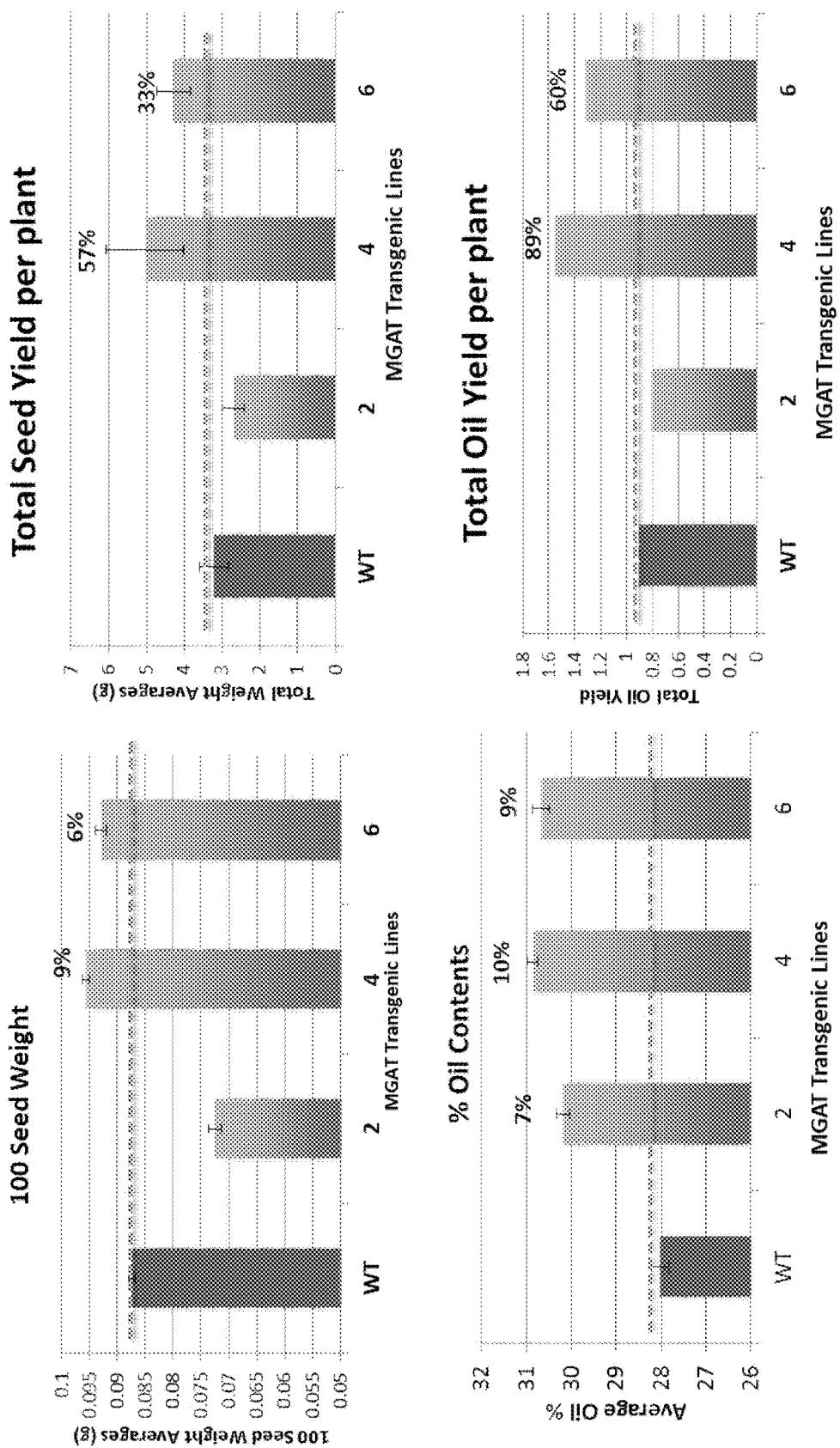
FIG. 12 presents four bar charts showing the analysis of seeds of MGAT1 transgenic T3 homozygous lines for seed size (mass) (shown as weight of 100 seeds)(upper left panel), total seed weight per plant (g per plant) (upper right panel), total % oil in seeds (lower left panel), and total per plant oil yield (g oil per plant) (lower right panel).
Figure 13:
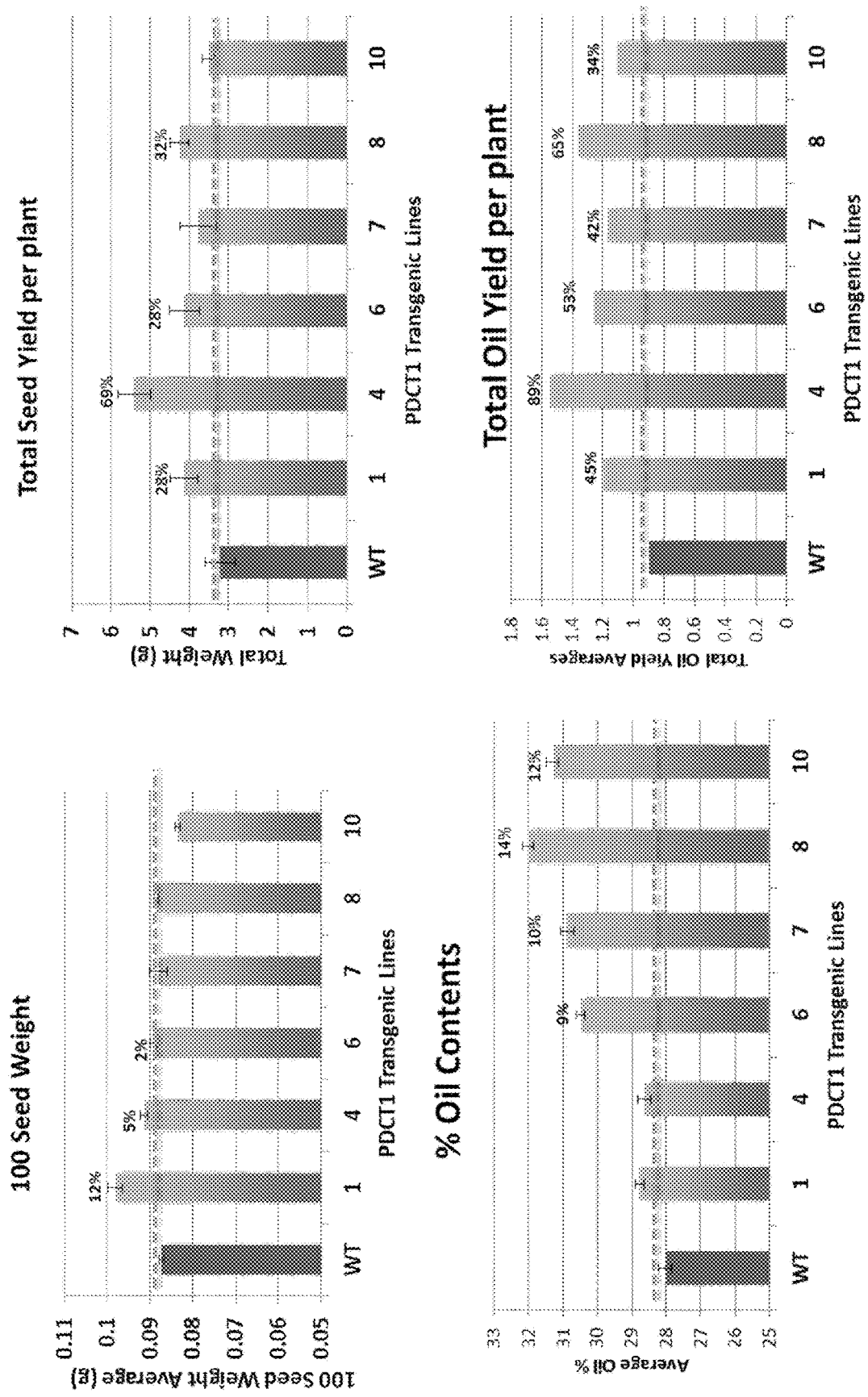
FIG. 13 presents four bar charts showing the analysis of seeds of PDCT1 transgenic T3 homozygous lines for seed size (mass) (shown as weight of 100 seeds)(upper left panel), total seed weight per plant (g per plant) (upper right panel), total % oil in seeds (lower left panel), and total per plant oil yield (g oil per plant) (lower right panel)
Figure 14:
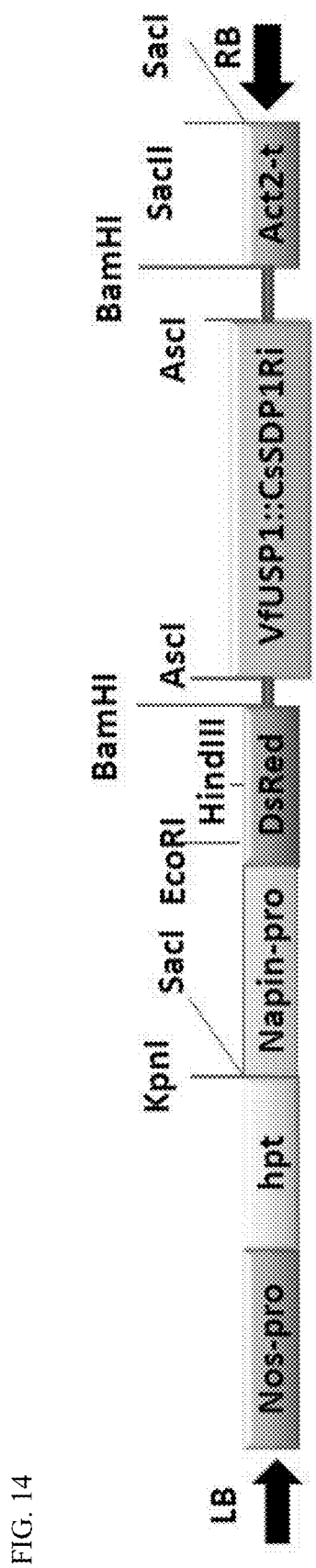
FIG. 14 schematically represents the gene construct for RNAi suppression of camelina (Cs) SDP1 gene in which the CsSDP1 RNAi cassette is expressed under a *Vicia faba* unknown seed specific promoter 1 (VbUSP1).
Figure 15:
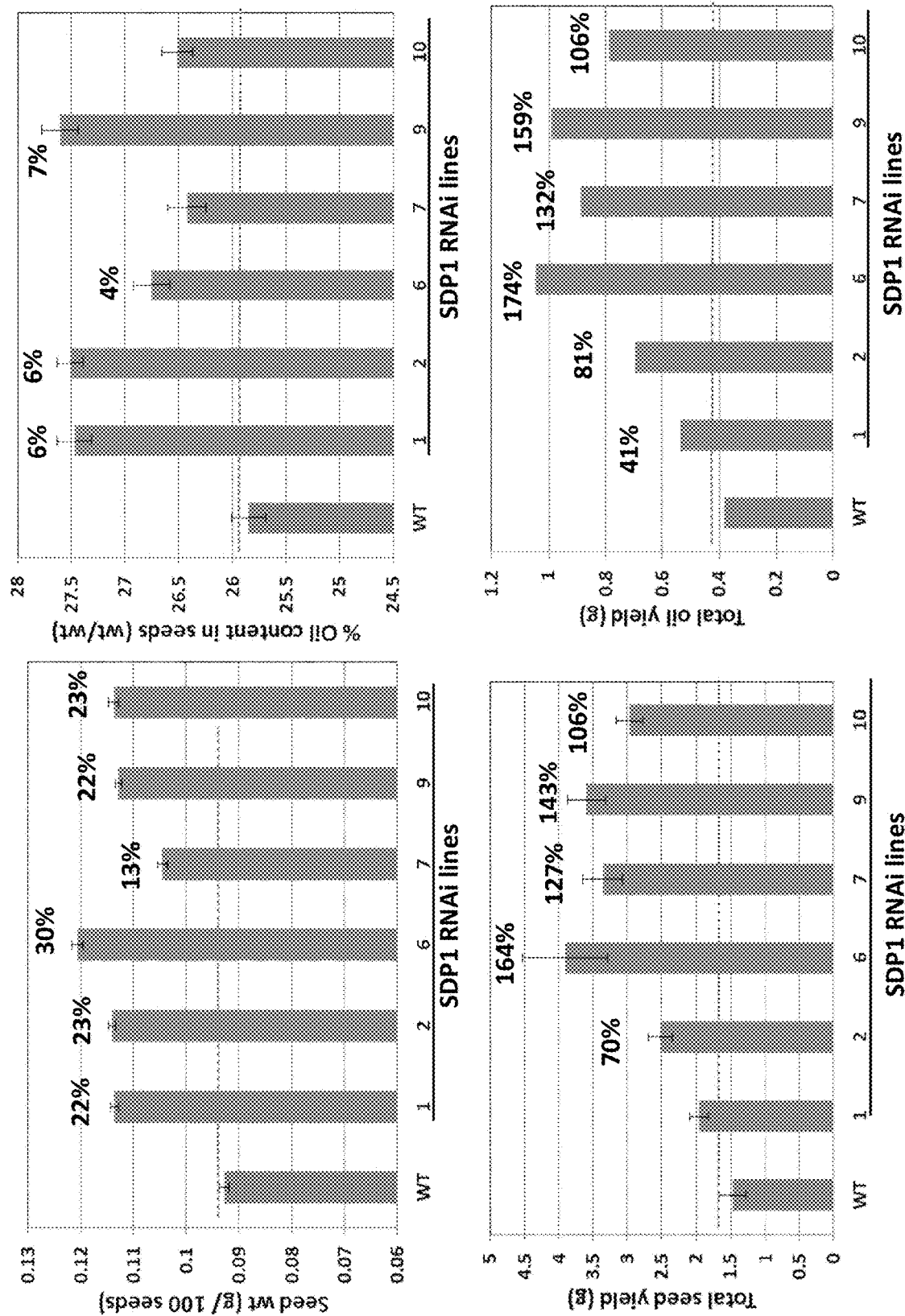
FIG. 15 presents four bar charts showing the analysis of seeds of SDP1 RNAi transgenic T3 homozygous lines seeds for seed size (mass) (shown as weight of 100 seeds)(upper left panel), total seed weight per plant (g per plant) (upper right panel), total % oil in seeds (lower left panel), and total per plant oil yield (g oil per plant) (lower right panel).

T3 seeds were subsequently collected from Camelina lines for each construct and analyzed for seed weight, seed yield per plant, percent oil, and total oil yield per plant. Results of the analysis for T3 seeds overexpressing MGAT1 or PDCT1 are shown in FIG. 12 or 13, respectively, and for T3 seeds having RNAi knockdown of SDP1 gene expression in FIG. 14.

Overexpression of MGAT1 or PDCT1, individually, or RNAi knockdown of the SDP1 gene in Camelina caused more than 30% increase in seed size, 6-15 increase in oil contents, and more than 2-fold increase (double) in total seed yield per plant basis. Therefore, these three new genes identified as significant in regulating oilseed yield produce almost a three-fold increase in total per plants energy yield.

Therefore, these additional genes are ideal to stack in a single line to increase the oil and seed yield in both biofuel crops such as Camelina, Castor, Cuphea, Canola, Crambe, flex etc as well as in food oil crops including soybean, groundnut, canola, palm etc.

Example 3. Transforming Various Other Crops with the Vectors

Agrobacterium-Mediated Transformation of Brassica napus (Canola)

Plant material: Mature seeds are surface sterilized in 10% commercial bleach for 30 min with gentle shaking and washed three times with sterile distilled water.

Culture initiation and transformation: Seeds are plated on germination medium (MS basal medium supplemented with 30 g/l sucrose) and incubated at 24° C. with a 16-h photoperiod at a light intensity of 60-80 μE/m²/s for 4-5 d. For transformation, cotyledons with ~2 mm of the petiole at the base are excised from the resulting seedlings, immersed in Agrobacterium tumefacians strain EHA101 suspension (grown from a single colony in 5 ml of minimal medium supplemented with appropriate antibiotics at 28° C. for 48 h) for 1 s and immediately embedded to a depth of ~2 mm in a co-cultivation medium (MS basal medium with 30 g/l sucrose and 20 μM benzyladenine). The inoculated cotyledons are incubated under the same growth conditions for 48 h.

Plant regeneration and selection: After co-cultivation, cotyledons are transferred on to a regeneration medium comprising MS medium supplemented with 30 g/l sucrose and 20 μM benzyladenine, 300 mg/l timentinin and 20 mg/l kanamycin sulfate. After 2-3 weeks, regenerated shoots are cut and maintained on MS medium for shoot elongation containing 30 g/l sucrose, 300 mg/l timentin, and 20 mg/l kanamycin sulfate. The elongated shoots are transferred to a rooting medium comprising MS basal medium supplemented with 30 g/l sucrose, 2 mg/l indole butyric acid (IBA) and 500 mg/L carbenicillin. After root formation, plants are transferred to soil and grown to seed maturity under growth chamber or greenhouse conditions.

Agrobacterium-Mediated Transformation of Soybean

The vectors are used for Agrobacterium-mediated transformation of soybean following a previously described procedure (Ko et al., 2006, Agrobacterium Protocols Wang K., ed., Vol. 1, pp 397-405, Humana Press).

Plant material: Immature seeds from soybean plants grown under greenhouse or field conditions are used as an explant source. Young pods are harvested and surface sterilized with 70% 2-propanol for 30 sec and 25% Clorox for 20 min followed by three washes with sterile distilled water.

Culture transformation and selection: Under aseptic conditions, immature seeds are removed from the pods and the cotyledons are separated from the seed coat followed by incubation in *A. tumefaciens* culture (grown from a single colony at 28° C., overnight) in co-cultivation medium (MS salts and B5 vitamins) supplemented with 30 g/l sucrose, 40 mg/l 2,4-D and 40 mg/l acetosyringone for 60 min. Infected explants are plated abaxial side up on agar-solidified co-cultivation medium and incubated at 25° C., in the dark for 4 d.

For selection of transformed tissues, cotyledons washed with 500 mg/l cephotaxine are placed abaxial side up on a medium for induction of somatic embryo formation (Gelrite-solidified MS medium medium containing 30 g/l sucrose, 40 mg/l 2,4-D, 500 mg/l cefotaxime, and 10 mg/l hygromycin) and incubated at 25° C., under a 23-h photoperiod (10-20 µE/m2/s) for 2 weeks. After another two weeks of growth under the same conditions in the presence of 25 mg/l hygromycin, the antibiotic-resistant somatic embryos are transferred on MS medium for embryo maturation supplemented with 60 g/l maltose, 500 mg/l cefotaxime, and 10 mg/l hygromycin and grown under the same conditions for 8 weeks with 2-week subculture intervals.

Plant regeneration and selection: The resulting cotyledonary stage embryos are desiccated at 25° C., under a 23-h photoperiod (60-80 µE/m2/s) for 5-7 d followed by culture on MS regeneration medium containing 30 g/l sucrose and 500 mg/l cefotaxime for 4-6 weeks for shoot and root development. When the plants are 5-10 cm tall, they are transferred to soil and grown in a greenhouse after acclimatization for 7 d.

The compositions and methods disclosed herein include (s) at least the following embodiments:

Embodiment 1. A method of increasing total oil content or seed yield in a plant or in a part, cell, or propagation material thereof, comprising: expressing a first transgenic expression cassette and a second transgenic expression cassette in a plant or in a tissue, organ, part, cell or propagation material thereof, wherein the first transgenic expression cassette comprises a nucleic acid sequence encoding a diacylglyerol acyltransferase (DGAT1) operatively linked to a plant-expressible promoter and the second transgenic expression cassette comprises a nucleic acid sequence encoding a glycerol-3-phosphate dehydrogenase (GPD1) operatively linked to a plant-expressible promoter; and selecting the plant or the tissue, organ, part, cell or propagation material thereof in which the total oil content or seed yield of the plant or the total oil content in the tissue, organ, part, cell or propagation material thereof is increased in comparison with a corresponding plant or a tissue organ part, cell or propagation material thereof that is not expressing the first transgenic expression cassette and the second transgenic expression cassette.

Embodiment 2. The method of embodiment 1, further comprising expressing a third transgenic expression cassette in the plant or in the tissue, organ, part, cell or propagation material thereof, wherein the third transgenic expression cassette comprises a nucleic acid sequence encoding a monoacylglycerol O-acyltransferase 1 (MGAT1) operably linked to a plant-expressible promoter, a nucleic acid sequence encoding a phosphatidylcholine diacylglycerol cholinephosphotransferase 1 (PDCT1) operably linked to a plant-expressible promoter, a nucleic acid sequence encoding a suppressor of expression of endogenous Sugar Dependent 1 (SDP1) operably linked to a plant-expressible promoter, or a combination thereof.

Embodiment 3. A method of increasing total oil content or seed yield in a plant or in a tissue, organ, part, cell or propagation material thereof, comprising: expressing a transgenic expression cassette in a plant or in a tissue, organ, part, cell or propagation material thereof, wherein the transgenic expression cassette comprises a nucleic acid sequence encoding a monoacylglycerol O-acyltransferase 1 (MGAT1) operably linked to a plant-expressible promoter, a nucleic acid sequence encoding a phosphatidylcholine diacylglycerol cholinephosphotransferase 1 (PDCT1) operably linked to a plant-expressible promoter, a nucleic acid sequence encoding a suppressor of expression of endogenous Sugar Dependent 1 (SDP1) operably linked to a plant-expressible promoter or a combination thereof and selecting the plant or the tissue, organ, part, cell or propagation material thereof in which the total oil content or seed yield of the plant or the total oil content in the tissue, organ, part, cell or propagation material thereof is increased in comparison with a corresponding plant or a tissue organ part, cell or propagation material thereof that is not expressing the transgenic expression cassette.

Embodiment 4. The method of embodiment 3, further comprising expressing a second transgenic expression cassette and a third transgenic expression cassette in a plant or in a tissue, organ, part, cell or propagation material thereof, wherein the second transgenic expression cassette comprises a nucleic acid sequence encoding a diacylglyerol acyltransferase (DGAT1) operatively linked to a plant-expressible promoter and the third transgenic expression cassette comprises a nucleic acid sequence encoding a glycerol-3-phosphate dehydrogenase (GPD1) operatively linked to a plant-expressible promoter.

Embodiment 5. A method of producing a transgenic plant having increased oil content or seed yield, the method comprises transforming a plant cell with a first transgenic expression cassette and a second transgenic expression cassette, wherein the first transgenic expression cassette comprises a nucleic acid sequence encoding a diacylglyerol acyltransferase (DGAT1) operatively linked to a plant-expressible promoter and the second transgenic expression cassette comprises a nucleic acid sequence encoding a glycerol-3-phosphate dehydrogenase (GPD1) operatively linked to a plant-expressible promoter; growing a plant from the transformed plant cell until the plant produces seed; and selecting a seed from a plant in which the oil content or the seed yield is higher than a plant of the same species not comprising the first and second expression cassettes.

Embodiment 6. The method of embodiment 5, further comprising transforming the plant cell with a third transgenic expression cassette, wherein the third transgenic expression cassette comprises a nucleic acid sequence encoding a monoacylglycerol O-acyltransferase 1 (MGAT1) operably linked to a plant-expressible promoter, a nucleic acid sequence encoding a phosphatidylcholine diacylglycerol cholinephosphotransferase 1 (PDCT1) operably linked to a plant-expressible promoter, a nucleic acid sequence encoding a suppressor of expression of endogenous Sugar Dependent 1 (SDP1) operably linked to a plant-expressible promoter, or a combination thereof.

Embodiment 7. A method of producing a transgenic plant having increased oil content or seed yield, comprising: transforming a plant cell with a transgenic expression cassette, wherein the transgenic expression cassette expresses a monoacylglycerol O-acyltransferase 1 (MGAT1), expresses a phosphatidylcholine diacylglycerol cholinephosphotransferase 1 (PDCT1), inhibits expression of Sugar Dependent 1 (SDP1), or a combination thereof; and growing a plant from the transformed plant cell until the plant produces seed; and selecting seeds from a plant in which the oil content or the seed yield is higher than a plant of the same species not comprising the transgenic expression cassette.

Embodiment 8. The method of embodiment 7, further comprising transforming the plant cell with a second transgenic expression cassette and a third transgenic expression cassette, wherein the second transgenic expression cassette comprises a nucleic acid sequence encoding a diacylglyerol acyltransferase (DGAT1) operatively linked to a plant-expressible promoter and the third transgenic expression cassette comprises a nucleic acid sequence encoding a glycerol-3-phosphate dehydrogenase (GPD1) operatively linked to a plant-expressible promoter.

Embodiment 9 The method of any one of embodiments 1-2, 4-6, and 8, wherein the glycerol-3-phosphate dehydrogenase is from a yeast selected from a genus consisting of *Cryptococcus, Torulopsis, Pityrosporum, Brettanomyces, Candida, Kloeckera, Trigonopsis, Trichosporon, Rhodotorula, Sporobolomyces, Bullera, Saccharomyces, Debaromyces, Lipomyces, Hansenula, Endomycopsis, Pichia* and *Hanseniaspora*.

Embodiment 10. The method of any one of embodiments 1-2, 4-6, and 8, wherein the glycerol-3-phosphate dehydrogenase is from a yeast selected from the species consisting of *Saccharomyces cerevisiae, Pichia pastoris, Hansenula polymorpha, Schizosaccharomyces pombe, Kluyveromyces lactis, Zygosaccharomyces rouxii, Yarrowia lipolitica, Emericella nidulans, Aspergillus nidulans, Debaryomyces hansenii* and *Torulaspora hansenii*.

Embodiment 11. The method of any one of embodiments 1-2, 4-6, and 8 to 10, wherein the diacylglyerol acyltransferase (DGAT1) is from an organism of a genus selected from *Arabidopsis, Tropaeolum, Brassicca, Glycine, Linum, Helianthus, Camelina, Arachis, Ricinus, Cuphea, Crambe,* and *Gossipium*.

Embodiment 12. The method of any one of embodiments 2 to 4, 6-11, wherein the MGAT1 is from a yeast or an organism of a genus selected from *Arabidopsis, Tropaeolum, Brassicca, Glycine, Linum, Helianthus, Camelina, Arachis, Ricinus, Cuphea, Crambe,* and *Gossipium*.

Embodiment 13. The method of any one of embodiments 2 to 4, 6-12, wherein the PDCT1 is from a yeast or an organism of a genus selected from *Arabidopsis, Tropaeolum, Brassicca, Glycine, Linum, Helianthus, Camelina, Arachis, Ricinus, Cuphea, Crambe,* and *Gossipium*.

Embodiment 14. The method of any one of embodiments 2 to 4, 6-13, wherein the SDP1 is from a yeast or an organism of a genus selected from *Arabidopsis, Tropaeolum, Brassicca, Glycine, Linum, Helianthus, Camelina, Arachis, Ricinus, Cuphea, Crambe,* and *Gossipium*.

Embodiment 15. The method of any one of embodiments 1 to 14, wherein the plant is selected from the group consisting of *Arabidopsis thaliana, Borago* spp., *Canola, Ricinus* spp., *Theobroma* spp., *Zea* spp., *Gossypium* spp*, Crambe* spp., *Cuphea* spp., *Linum* spp., *Lesquerella* spp., *Limnanthes* spp., *Linola, Tropaeolum* spp., *Oenothera* spp., *Olea* spp., *Elaeis* spp., *Arachis* spp., rapeseed, *Carthamus* spp., *Glycine* spp., *Soja* spp., *Helianthus* spp., *Nicotiana* spp., *Vernonia* spp., *Triticum* spp., *Hordeum* spp., *Oryza* spp., *Avena* spp., *Sorghum* spp., *Secale* spp., Brassicaceae, and other members of the plant family Gramineae.

Embodiment 16. The method of any one of embodiments 1 to 15, wherein the plant is an oilseed plant or the tissue, organ, part, cell or propagation material thereof.

Embodiment 17. The method of embodiment 16, wherein the oilseed plant is selected from the group consisting of *Borago officinalis, Brassica campestris, Brassica napus, Brassica rapa, Camelina* species, *Cannabis sativa, Carthamus tinctorius, Cocos nucifera, Crambe abyssinica, Cuphea* species, *Elaeis guinensis, Elaeis oleifera, Glycine max, Gossypium hirsutum, Gossypium barbadense, Gossypium herbaceum, Helianthus annuus, Linum usitatissimum, Oenothera biennis, Olea europaea, Oryza sativa, Ricinus communis, Sesamum indicum, Triticum species, Zea mays,* walnut, and almond.

Embodiment 18. The method of any one of embodiments 1 to 17, wherein total oil content of the plant is increased by at least 5%, at least 10%, or at least 15%.

Embodiment 19. The method of any one of embodiments 1 to 18, wherein seed yield, as measured in weight of seed, of the plant is increased by at least 30%, at least 40%, or at least 50%.

Embodiment 20. The method of any one of embodiments 1 to 19, wherein DGAT1 has a sequence comprising SEQ ID NO:1; GPD1 has a sequence comprising SEQ ID NO:2; MGAT1 has a sequence comprising SEQ ID NO:3; PDCT1 has a sequence comprising SEQ ID NO:4; SDP1 has a sequence comprising SEQ ID NO:5; or the suppressor of SDP1 expression has a sequence comprising SEQ ID NO:13.

Embodiment 21. The method of any one of embodiments 1 to 20, wherein the plant-expressible promoter is a glycinin promoter or an oleosin promoter.

Embodiment 22. The method of embodiment 21 wherein the glycinin promoter or the oleosin promoter is from soybean or a Brassica organism.

Embodiment 23. The method of embodiment 21 or 22, wherein the glycinin promoter comprises SEQ ID NO:6 or the oleosin promoter comprises SEQ ID NO:7 or 8.

Embodiment 24. A trangenic plant or a tissue, organ, part, cell, or propagation material thereof made by the method of any one of embodiments 1 to 23.

Embodiment 25. The transgenic plant or the tissue, organ, part, cell, or propagation material thereof of embodiment 24 which is a seed.

Embodiment 26. A transgenic expression cassette comprising a polynucleotide encoding a diacylglyerol acyltransferase (DGAT1) operatively linked to a plant-expressible promoter; a polynucleotide encoding a glycerol-3-phosphate dehydrogenase (GPD1) operatively linked to a plant-expressible promoter; a polynucleotide encoding a monoacylglycerol O-acyltransferase 1 (MGAT1) operatively linked to a plant-expressible promoter; a polynucleotide encoding a phosphatidylcholine diacylglycerol cholinephosphotransferase 1 (PDCT1) operatively linked to a plant-expressible promoter; a polynucleotide encoding a suppressor of expression of Sugar Dependent 1 (SDP1) operatively linked to a plant-expressible promoter; or a combination thereof.

Embodiment 27. The expression cassette of embodiment 26, wherein DGAT1 has a sequence comprising SEQ ID NO:1; GPD1 has a sequence comprising SEQ ID NO:2; MGAT1 has a sequence comprising SEQ ID NO:3; PDCT1 has a sequence comprising SEQ ID NO:4; SDP1 has a sequence comprising SEQ ID NO:5; or the suppressor of SDP1 expression has a sequence comprising SEQ ID NO:13.

Embodiment 28. The expression cassette of embodiment 26 or 27 wherein the plant-expressible promoter is a glycinin promoter or an oleosin promoter.

Embodiment 29. The expression cassette of any one of embodiments 26 to 28, wherein the glycinin promoter or the oleosin promoter is from soybean or a *Brassica* organism.

Embodiment 30. The expression cassette of any one of embodiments 26 to 29, wherein the glycinin promoter comprises SEQ ID NO:6 or the oleosin promoter comprises SEQ ID NO:7 or 8.

Embodiment 31. The expression cassette of any one of embodiments 26 to 29, wherein the polynucleotide encoding a diacylglyerol acyltransferase (DGAT1) operatively linked to a plant-expressible promoter is operatively linked to a transcription terminator; the polynucleotide encoding a glycerol-3-phosphate dehydrogenase (GPD1) operatively linked to a plant-expressible promoter is operatively linked to a transcription terminator; the polynucleotide encoding a monoacylglycerol O-acyltransferase 1 (MGAT1) operatively linked to a plant-expressible promoter is operatively linked to a transcription terminator; the polynucleotide encoding a phosphatidylcholine diacylglycerol cholinephosphotransferase 1 (PDCT1) operatively linked to a plant-expressible promoter is operatively linked to a transcription terminator; or the polynucleotide encoding a suppressor of expression of Sugar Dependent 1 (SDP1) operatively linked to a plant-expressible promoter is operatively linked to a transcription terminator.

Embodiment 32. The expression cassette of embodiment 31 wherein the transcription terminator comprises SEQ ID NO:9.

Embodiment 33. A transgenic plant comprising a polynucleotide encoding a diacylglyerol acyltransferase (DGAT1) operatively linked to a plant-expressible promoter and a polynucleotide encoding a glycerol-3-phosphate dehydrogenase (GPD1) operatively linked to a plant-expressible promoter.

Embodiment 34. The transgenic plant of embodiment 33, further comprising a polynucleotide encoding a monoacylglycerol O-acyltransferase 1 (MGAT1) operatively linked to a plant-expressible promoter; a polynucleotide encoding a phosphatidylcholine diacylglycerol cholinephosphotransferase 1 (PDCT1) operatively linked to a plant-expressible promoter; a polynucleotide encoding a suppressor of expression of Sugar Dependent 1 (SDP1) operatively linked to a plant-expressible promoter; or a combination thereof.

Embodiment 35. A transgenic plant comprising a polynucleotide encoding a monoacylglycerol O-acyltransferase 1 (MGAT1) operatively linked to a plant-expressible promoter; a polynucleotide encoding a phosphatidylcholine diacylglycerol cholinephosphotransferase 1 (PDCT1) operatively linked to a plant-expressible promoter; a polynucleotide encoding a suppressor of expression of Sugar Dependent 1 (SDP1) operatively linked to a plant-expressible promoter; or a combination thereof.

Embodiment 36. The transgenic plant of embodiment 35, further comprising a polynucleotide encoding a diacylglyerol acyltransferase (DGAT1) operatively linked to a plant-expressible promoter and a polynucleotide encoding a glycerol-3-phosphate dehydrogenase (GPD1) operatively linked to a plant-expressible promoter.

Embodiment 37. The transgenic plant of any one of embodiments 33-36, wherein DGAT1 has a sequence comprising SEQ ID NO:1; GPD1 has a sequence comprising SEQ ID NO:2; MGAT1 has a sequence comprising SEQ ID NO:3; PDCT1 has a sequence comprising SEQ ID NO:4; SDP1 has a sequence comprising SEQ ID NO:5; or the suppressor of SDP1 expression has a sequence comprising SEQ ID NO:13.

Embodiment 38. The transgenic plant of any one of embodiments 33 to 37, wherein total oil content of the plant is increased by at least 5%, at least 10%, or at least 15% compared to a plant of the same species not comprising the polynucleotide(s).

Embodiment 39. The transgenic plant of any one of embodiments 33 to 38, wherein seed yield, as measured in weight of seed, of the plant is increased by at least 30%, at least 40%, or at least 50% compared to a plant of the same species not comprising the polynucleotide(s).

Embodiment 40 The transgenic plant of any one of embodiments 33 to 39, wherein the glycerol-3-phosphate dehydrogenase is from a yeast selected from a genus consisting of *Cryptococcus, Torulopsis, Pityrosporum, Brettanomyces, Candida, Kloeckera, Trigonopsis, Trichosporon, Rhodotorula, Sporobolomyces, Bullera, Saccharomyces, Debaromyces, Lipomyces, Hansenula, Endomycopsis, Pichia* and *Hanseniaspora.*

Embodiment 41. The transgenic plant of any one of embodiments 33 to 39, wherein the glycerol-3-phosphate dehydrogenase is from a yeast selected from the species consisting of *Saccharomyces cerevisiae, Pichia pastoris, Hansenula polymorpha, Schizosaccharomyces pombe, Kluyveromyces lactis, Zygosaccharomyces rouxii, Yarrowia lipolitica, Emericella nidulans, Aspergillus nidulans, Debaryomyces hansenii* and *Torulaspora hansenii.*

Embodiment 42. The transgenic plant of any one of embodiments 33 to 41, wherein the diacylglyerol acyltransferase (DGAT1) is from an organism of a genus selected from *Arabidopsis, Tropaeolum, Brassicca, Glycine, Linum, Helianthus, Camelina, Arachis, Ricinus, Cuphea, Crambe*, and *Gossipium.*

Embodiment 43. The transgenic plant of any one of embodiments 33 to 42, wherein the MGAT1 is from a yeast or an organism of a genus selected from *Arabidopsis, Tropaeolum, Brassicca, Glycine, Linum, Helianthus, Camelina, Arachis, Ricinus, Cuphea, Crambe*, and *Gossipium.*

Embodiment 44. The transgenic plant of any one of embodiments 33 to 43, wherein the PDCT1 is from a yeast or an organism of a genus selected from *Arabidopsis, Tropaeolum, Brassicca, Glycine, Linum, Helianthus, Camelina, Arachis, Ricinus, Cuphea, Crambe*, and *Gossipium.*

Embodiment 45. The transgenic plant of any one of embodiments 33 to 44, wherein the SDP1 is from a yeast or an organism of a genus selected from *Arabidopsis, Tropaeolum, Brassicca, Glycine, Linum, Helianthus, Camelina, Arachis, Ricinus, Cuphea, Crambe*, and *Gossipium.*

Embodiment 46. The transgenic plant of any one of embodiments 33 to 45, wherein the plant is selected from the group consisting of *Arabidopsis thaliana, Borago* spp., Canola, *Ricinus* spp., *Theobroma* spp., *Zea* spp., *Gossypium* spp, *Crambe* spp., *Cuphea* spp., *Linum* spp., *Lesquerella* spp., *Limnanthes* spp., *Linola, Tropaeolum* spp., *Oenothera* spp., *Olea* spp., *Elaeis* spp., *Arachis* spp., rapeseed, *Carthamus* spp., *Glycine* spp., *Soja* spp., *Helianthus* spp., *Nicotiana* spp., *Vernonia* spp., *Triticum* spp., *Hordeum* spp., *Oryza* spp., *Avena* spp., *Sorghum* spp., *Secale* spp., Brassicaceae, and other members of the plant family Gramineae.

Embodiment 47. The transgenic plant of any one of embodiments 33 to 46, wherein the plant is an oilseed plant.

Embodiment 48. The transgenic plant of embodiment 47, wherein the oilseed plant is selected from the group consisting of *Borago officinalis, Brassica campestris, Brassica napus, Brassica rapa, Camelina* species, *Cannabis sativa, Carthamus tinctorius, Cocos nucifera, Crambe abyssinica, Cuphea* species, *Elaeis guinensis, Elaeis oleifera, Glycine max, Gossypium hirsutum, Gossypium barbadense, Gossypium herbaceum, Helianthus annuus, Linum usitatissimum, Oenothera biennis, Olea europaea, Oryza sativa, Ricinus communis, Sesamum indicum, Triticum* species, *Zea mays*, walnut and almond.

Embodiment 49. A binary vector comprising SEQ ID NO:19.

Embodiment 50. The binary vector of embodiment 49 comprising SEQ ID NO: 14.

In general, the invention may alternately comprise, consist of, or consist essentially of, any appropriate components herein disclosed. The invention may additionally, or alternatively, be formulated so as to be devoid, or substantially free, of any components, materials, ingredients, adjuvants or species used in the prior art compositions or that are otherwise not necessary to the achievement of the function and/or objectives of the present invention. The endpoints of all ranges directed to the same component or property are inclusive and independently combinable (e.g., ranges of "less than or equal to 25 wt %, or 5 wt % to 20 wt %," is inclusive of the endpoints and all intermediate values of the ranges of "5 wt % to 25 wt %," etc.). Disclosure of a narrower range or more specific group in addition to a broader range is not a disclaimer of the broader range or larger group. "Combination" is inclusive of blends, mixtures, alloys, reaction products, and the like. Furthermore, the terms "first," "second," and the like, herein do not denote any order, quantity, or importance, but rather are used to denote one element from another. The terms "a" and "an" and "the" herein do not denote a limitation of quantity, and are to be construed to cover both the singular and the plural, unless otherwise indicated herein or clearly contradicted by context. "Or" means "and/or." The suffix "(s)" as used herein is intended to include both the singular and the plural of the term that it modifies, thereby including one or more of that term (e.g., the film(s) includes one or more films). Reference throughout the specification to "one embodiment", "another embodiment", "an embodiment", and so forth, means that a particular element (e.g., feature, structure, and/or characteristic) described in connection with the embodiment is included in at least one embodiment described herein, and may or may not be present in other embodiments. In addition, it is to be understood that the described elements may be combined in any suitable manner in the various embodiments.

The modifier "about" used in connection with a quantity is inclusive of the stated value and has the meaning dictated by the context (e.g., includes the degree of error associated with measurement of the particular quantity). The notation "±10%" means that the indicated measurement can be from an amount that is minus 10% to an amount that is plus 10% of the stated value. The terms "front", "back", "bottom", and/or "top" are used herein, unless otherwise noted, merely for convenience of description, and are not limited to any one position or spatial orientation. "Optional" or "optionally" means that the subsequently described event or circumstance can or cannot occur, and that the description includes instances where the event occurs and instances where it does not. Unless defined otherwise, technical and scientific terms used herein have the same meaning as is commonly understood by one of skill in the art to which this invention belongs.

All cited patents, patent applications, and other references are incorporated herein by reference in their entirety. However, if a term in the present application contradicts or conflicts with a term in the incorporated reference, the term from the present application takes precedence over the conflicting term from the incorporated reference.

While particular embodiments have been described, alternatives, modifications, variations, improvements, and substantial equivalents that are or may be presently unforeseen may arise to applicants or others skilled in the art. Accordingly, the appended claims as filed and as they may be amended are intended to embrace all such alternatives, modifications variations, improvements, and substantial equivalents.

The invention claimed is:

1. A transgenic plant transformed with
    (i) a first expression cassette comprising a heterologous plant-expressible seed-specific promoter operably linked to a nucleotide sequence encoding an Arabidopsis diacylglycerol actyltransferase 1 (DGAT1) protein,
    (ii) a second expression cassette comprising a heterologous plant-expressible seed-specific promoter operably linked to a nucleotide sequence encoding a plant or yeast glycerol 3-phosphate dehydrogenase 1 (GPD1) protein, and
    (iii) a third expression cassette comprising a heterologous plant-expressible seed-specific promoter operably linked to the nucleotide sequence set forth in SEQ ID NO: 3 encoding monoacylglycerol O-acyltransferase 1 (MGAT1) protein,
    wherein overexpression of said DGAT1, GPD1, and MGAT1 proteins in said transgenic plant results in increased total seed oil content per transgenic plant and increased seed yield per transgenic plant as compared to a control plant of the same species lacking said first, second, and third expression cassettes and grown under identical growth conditions.

2. The transgenic plant of claim 1, wherein said nucleotide sequence encoding said Arabidopsis diacylglycerol actyltransferase 1 (DGAT1) protein is SEQ ID NO: 1.

3. The transgenic plant of claim 1, wherein said nucleotide sequence encoding said plant or yeast glycerol 3-phosphate dehydrogenase 1 (GPD1) protein is SEQ ID NO: 2.

4. The transgenic plant of claim 1, wherein said transgenic plant is further transformed with a fourth expression cassette comprising
    (i) a heterologous plant-expressible seed-specific promoter operably linked to a nucleotide sequence encoding a plant phosphatidylcholine diacylglycerol cholinephosphotransferase 1 (PDCT1) protein, or
    (ii) an RNA interference (RNAi) suppressor construct comprising a heterologous plant-expressible seed-specific promoter operably linked to a nucleic acid sequence encoding an RNAi suppressor of expression of endogenous plant Sugar Dependent 1 (SDP1) protein in said transgenic plant,
    wherein overexpression of said PDCT1 protein or reduction in the expression of said endogenous plant SDP1 protein in said transgenic plant by said RNAi suppressor results in increased total transgenic seed oil content per transgenic plant and increased seed yield per transgenic plant as compared to a control plant of the same species lacking said fourth expression cassette and grown under identical growth conditions.

5. The transgenic plant of claim 4, wherein said nucleotide sequence encoding said plant phosphatidylcholine diacylglycerol cholinephosphotransferase 1 (PDCT1) protein is SEQ ID NO: 4; or wherein said RNAi suppressor construct has the nucleotide sequence set forth in SEQ ID NO: 13.

6. The transgenic plant of claim 1, wherein said total seed oil content per transgenic plant is increased by at least 15% as compared to said control plant.

7. The transgenic plant of claim 1, wherein said seed yield, as measured in weight of seed, per transgenic plant is increased by at least 50% as compared to said control plant.

8. The transgenic plant of claim 1, wherein said glycerol-3-phosphate dehydrogenase 1 (GPD1) protein is from a yeast genus selected from the group consisting of *Cryptococcus, Torulopsis, Pityrosporum, Brettanomyces, Candida, Kloeckera, Trigonopsis, Trichosporon, Rhodotorula, Sporobolomyces, Bullera, Saccharomyces, Debaromyces, Lipomyces, Hansenula, Endomycopsis, Pichia* and *Hanseniaspora*.

9. The transgenic plant of claim 4, wherein the plant phosphatidylcholine diacylglycerol cholinephosphotransferase 1 (PDCT1) protein is from a plant genus selected from the group consisting of *Arabidopsis, Tropaeolum, Brassica, Glycine, Linum, Helianthus, Camelina, Arachis, Ricinus, Cuphea, Crambe* and *Gossipium*.

10. The transgenic plant of claim 1, wherein said transgenic plant is selected from the group consisting of *Arabidopsis thaliana, Borago* species, *Canola* species, *Ricinus* species, *Theobroma* species, *Zea* species, *Gossypium* species, *Crambe* species, *Cuphea* species, *Linum* species, *Lesquerella* species, *Limnanthes* species, *Linola* species, *Tropaeolum* species, *Oenothera* species, *Olea* species, *Elaeis* species, *Arachis* species, rapeseed species, *Carthamus* species, *Glycine* species, *Soja* species, *Helianthus* species, *Nicotiana* species, *Vermonia* species, *Triticum* species, *Hordeum* species, *Oryza* species, *Avena* species, *Sorghum* species and *Secale* species.

11. The transgenic plant of claim 1, wherein said transgenic plant is selected from the group consisting of *Borago officinalis, Brassica campestris, Brassica napus, Brassica rapa, Camelina* species, *Cannabis sativa, Carthamus tinctorius, Cocos nucifera, Crambe abyssinica, Cuphea species, Elaeis guinensis, Elaeis oleifera, Glycine max, Gossypium hirsutum, Gossypium barbadense, Gossypium herbaceum, Helianthus annuus, Linum usitatissimum, Oenothera biennis, Olea europaea, Oryza sativa, Ricinus communis, Sesamum indicum, Triticum* species, *Zea mays*, walnut species and almond species.

12. A method of making a transgenic plant with increased total seed oil content and increased seed yield, said method comprising:

transforming plant cells with (i) a first expression cassette comprising a heterologous plant-expressible seed-specific promoter operably linked to a nucleotide sequence encoding an Arabidopsis diacylglycerol actyltransferase 1 (DGAT1) protein, (ii) a second expression cassette comprising a heterologous plant-expressible seed-specific promoter operably linked to a plant or yeast glycerol 3-phosphate dehydrogenase 1 (GPD1) protein, and (iii) a third expression cassette comprising a heterologous plant-expressible seed-specific promoter operably linked to the nucleotide sequence as set forth in SEQ ID NO: 3 encoding the monoacylglycerol O-acyltransferase 1 (MGAT1) protein to produce transformed cells;

generating transformed plants from the transformed cells; and selecting a transgenic plant from the transformed plants, wherein the selected transgenic plant overexpresses said DGAT1, GPD1 and MGAT1 proteins and exhibits increased total seed oil content per transgenic plant and increased seed yield per transgenic plant as compared to a control plant of the same species lacking said first, second, and third expression cassettes and grown under identical growth conditions.

13. The method of claim 12, wherein said nucleotide sequence encoding said Arabidopsis diacylglycerol actyltransferase 1 (DGAT1) protein is SEQ ID NO: 1, or wherein said nucleotide sequence encoding said plant or yeast glycerol 3-phosphate dehydrogenase 1 (GPD1) protein has the nucleotide sequence is SEQ ID NO: 2.

14. The method of claim 12, wherein total seed oil content per transgenic plant is increased by at least 15% as compared to said control plant; and wherein seed yield, as measured in weight of seed, per transgenic plant is increased by at least 50% as compared to said control plant.

15. The method of claim 12, wherein said selected transgenic plant is further transformed with a fourth expression cassette comprising (i) a nucleic acid molecule comprising a heterologous plant-expressible seed-specific promoter operably linked to a nucleotide sequence encoding a plant phosphatidylcholine diacylglycerol cholinephosphotransferase 1 (PDCT1) protein, or (ii) an RNA interference (RNAi) suppressor construct comprising a heterologous plant-expressible seed-specific promoter operably linked to a nucleic acid sequence encoding an RNAi suppressor of expression of endogenous plant Sugar Dependent 1 (SDP1) protein in said transgenic plant, wherein overexpression of said PDCT1 protein or reduction in the expression of said endogenous plant SDP1 protein in said transgenic plant by said RNAi suppressor results in increased total seed oil content per transgenic plant and increased seed yield per transgenic plant as compared to a control plant of the same species lacking said fourth expression cassette and grown under identical growth conditions.

16. The method of claim 15, wherein said nucleotide sequence encoding said plant phosphatidylcholine diacylglycerol cholinephosphotransferase 1 (PDCT1) protein is SEQ ID NO: 4, or wherein said RNAi suppressor construct has the nucleotide sequence set forth in SEQ ID NO: 13.

17. The method of claim 12, wherein said glycerol-3-phosphate dehydrogenase 1 (GPD1) protein is from a yeast genus selected from the group consisting of *Cryptococcus, Torulopsis, Pityrosporum, Brettanomyces, Candida, Kloeckera, Trigonopsis, Trichosporon, Rhodotorula, Sporobolomyces, Bullera, Saccharomyces, Debaromyces, Lipomyces, Hansenula, Endomycopsis, Pichia* and *Hanseniaspora*.

18. The method of claim 15, wherein the plant phosphatidylcholine diacylglycerol cholinephosphotransferase 1 (PDCT1) protein is from a plant genus selected from the group consisting of *Arabidopsis, Tropaeolum, Brassica, Glycine, Linum, Helianthus, Camelina, Arachis, Ricinus, Cuphea, Crambe* and *Gossipium*.

19. The method of claim 12, wherein said transgenic plant is selected from the group consisting of *Arabidopsis thaliana, Borago* species, *Canola* species, *Ricinus* species, *Theobroma* species, *Zea* species, *Gossypium* species, *Crambe* species, *Cuphea* species, *Linum* species, *Lesquerella* species, *Limnanthes* species, *Linola* species, *Tropaeolum* species, *Oenothera* species, *Olea* species, *Elaeis* species, *Arachis* species, rapeseed species, *Carthamus* species, *Glycine* species, *Soja* species, *Helianthus* species, *Nicotiana* species, *Vermonia* species, *Triticum* species, *Hordeum* species, *Oryza* species, *Avena* species, *Sorghum* species and *Secale* species.

20. The method of claim 12, wherein said transgenic plant is selected from the group consisting of *Borago officinalis, Brassica campestris, Brassica napus, Brassica rapa, Camelina* species, *Cannabis sativa, Carthamus tinctorius, Cocos nucifera, Crambe abyssinica, Cuphea* species, *Elaeis guinensis, Elaeis oleifera, Glycine max, Gossypium hirsutum, Gossypium barbadense, Gossypium herbaceum, Helianthus annuus, Linum usitatissimum, Oenothera biennis, Olea europaea, Oryza sativa, Ricinus communis, Sesamum indicum, Triticum species, Zea mays*, walnut species and almond species.

\* \* \* \* \*